(12) United States Patent
Amedio et al.

(10) Patent No.: US 8,048,906 B2
(45) Date of Patent: Nov. 1, 2011

(54) OPTICALLY PURE AND ENRICHED ISOMERS OF CHELATING LIGANDS AND CONTRAST AGENTS

(75) Inventors: John C. Amedio, Franklin, MA (US); Peter D. Caravan, Cambridge, MA (US); Vincent Jacques, Andover, MA (US); Kevin L. Zhou, Mansfield, MA (US); Stuart Levy, Somerville, MA (US); Shirley Kalogeropoulos, Lowell, MA (US); Matthew Greenfield, Middleton, MA (US)

(73) Assignee: Catalyst Medical, Belmont, MA (US)

(*) Notice: Subject to any disclaimer, the term of this patent is extended or adjusted under 35 U.S.C. 154(b) by 1246 days.

(21) Appl. No.: 11/542,883

(22) Filed: Oct. 4, 2006

(65) Prior Publication Data

US 2007/0244316 A1 Oct. 18, 2007

Related U.S. Application Data

(63) Continuation of application No. 10/850,134, filed on May 20, 2004, now abandoned.

(60) Provisional application No. 60/473,369, filed on May 23, 2003.

(51) Int. Cl.
*A01N 43/36* (2006.01)
*A61K 31/40* (2006.01)
*C07D 487/22* (2006.01)
*C07B 47/00* (2006.01)

(52) U.S. Cl. .................................. 514/410; 540/145

(58) Field of Classification Search .................. 540/145; 514/410
See application file for complete search history.

(56) References Cited

U.S. PATENT DOCUMENTS

| | | | |
|---|---|---|---|
| 4,880,008 | A | 11/1989 | Lauffer |
| 4,899,755 | A | 2/1990 | Lauffer et al. |
| 6,406,297 | B1 | 6/2002 | Raymond et al. |
| 6,515,113 | B2 | 2/2003 | Raymond et al. |
| 6,549,798 | B2 | 4/2003 | Stefancik et al. |
| 6,652,835 | B1 | 11/2003 | Lauffer et al. |

FOREIGN PATENT DOCUMENTS

| | | | |
|---|---|---|---|
| WO | WO 96/23526 | | 8/1996 |
| WO | WO 01/08712 | | 2/2001 |
| WO | WO 01/09188 | | 2/2001 |
| WO | WO 02/24235 | * | 3/2002 |

OTHER PUBLICATIONS

Woods et al., "Correlation of Water Exchange Rate with Isomeric Composition in Diastereoisomeric Gadolinium Complexes of Tetra(carboxyethyl)dota and Related Macrocyclic Ligands," *J. Am. Chem. Soc.*, 2000, 122:9781-9792.

André et al., "High Relaxivity for Monomeric Gd(DOTA)-Based MRI Contrast Agents, Thanks to Micellar Self-Organization," *Chem. Eur. J.*, 1999, 5(10):2977-2983.

Caravan et al., "Gadolinium(III) Chelates as MRI Contrast Agents: Structure, Dynamics, and Applications," *Chem. Rev.*, 1999, 99:2293-2352.

"2001 Guidelines for Authors," *J. Org. Chem.*, 2001, 66(1):18A-24A.

Jones (ed.), "A Short Guide to Abbreviations and Their Use in Peptide Science," *J. Peptide Sci.*, 1999, 5:465-471.

Mummert et al., "Development of a Peptide Inhibitor of Hyaluronan-mediated Leukocyte Trafficking," *J. Exp. Med.*, 2000, 192(6):769-779.

Nielsen et al., "Identification of a Major Heparin and Cell Binding Site in the LG4 Module of the Laminin α5 Chain," *J. Biol. Chem.*, 2000, 275(19):14517-14523.

Cai et al., "Synthesis of CMI-977, a Potent 5-Lipoxygenase Inhibitor," *Organic Process Research & Development*, 1999, 3:73-76.

Crossland et al., "Sulfonate Leaving Groups, Structure and Reactivity. 2,2,2-Trifluoroethanesulfonate," *J. Am. Chem. Soc.*, 1971, 93(17):4217-4219.

Doolittle and Heath, "(S)-Tetrahydro-5-oxo-2-furancarboxylic Acid: A Chiral Derivatizing Reagent for Asymmetric Alcohols," *J. Org. Chem.*, 1984, 49:5041-5050.

Eisenwiener et al., "A Convenient Synthesis of Novel Bifunctional Prochelators for Coupling to Bioactive Peptides for Radiometal Labelling," *Bioorg. Med. Chem. Lett.*, 2000, 10:2133-2135.

Gringore and Rouessac, "(S)-(+)-γ-Butyrolactone-γ-Carboxylic Acid (2-Furancarboxylic acid, tetrahydro-5-oxo-, (S)-)," *Organic Syntheses*, 1985, 63:121-126.

Hoffmann and Wasielewski, "Synthesis of Depsipeptides, Part XI*, Synthesis of Didepsipeptides of D-α-Hydroxyglutaric Acid," *Roczniki Chem.*, 1975, 49:151-158.

Jacques and Desreux, "Synthesis of MRI Contrast Agents II. Macrocyclic Ligands," *The Chemistry of Contrast Agents in Medical Magnetic Resonance Imaging*, 2001, Meerbach and Tóth (eds.), John Wiley and Sons, New York, NY, pp. 157-191.

Kang et al., "Synthesis, Characterization, and Crystal Structure of the Gadolinium(III) Chelate of (1R,4R,7R)-α,α',αΔ-Trimethyl-1,4,7,10-tetraazacyclododecane-1,4,7-triacetic Acid (DO3MA)," *Inorg. Chem.*, 1993, 32:2912-2918.

Okabe et al., "Synthesis of the Dideoxynucleosides ddC and CNT from Glutamic Acid, Ribonolactone, and Pyrimidine Bases," *J. Org. Chem.*, 1988, 53:4780-4786.

Schmidt et al., "Enantioselective Syntheses of (R)- and (S)-Hexahydropyridazine-3-carboxylic Acid Derivatives," *Synthesis*, 1996, pp. 223-229.

Shin et al., "Synthesis of Optically Active Phthaloyl D-Aminooxy Acids from L-Amino Acids or L-Hydroxy Acids as Building Blocks for the Preparation of Aminooxy Peptides," *J. Org. Chem.*, 2000, 65:7667-7675.

Streitwieser Jr. et al., "Kinetics and Isotope Effects in Solvolyses of Ethyl Trifluoromethanesulfonate," *J. Am. Chem. Soc.*, 1968, 90(6):1598-1601.

(Continued)

*Primary Examiner* — Paul V. Ward
(74) *Attorney, Agent, or Firm* — Fish & Richardson P.C.

(57) ABSTRACT

Organic chelating ligands, organic chelating ligand precursors, and metal chelates are disclosed. Methods for synthesizing the same are also described, including methods for preparing optically-enriched or optically-pure compositions of the same.

33 Claims, 8 Drawing Sheets

OTHER PUBLICATIONS

Vigneron et al., "L'Eldanolide, Phéromone Des Glandes Alaires De La Pyrale De La Canne à Sucre, *Eldana Saccharina* (Wlk.): Structure et Synthèse De Ses Deux Énantioméres," *Tetrahedron*, 1984, 40(18):3521-3529 (includes English language Abstract).

Zamzow and Höcker, "Synthesis of polymers with pendant spiro orthoester groups," *Macromol. Chem. Phys.*, 1994, 195:2381-2400.

* cited by examiner

Scheme A
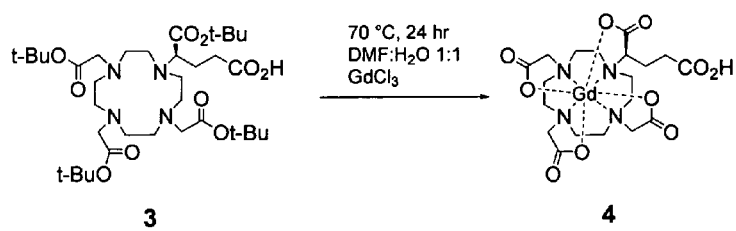
Scheme B
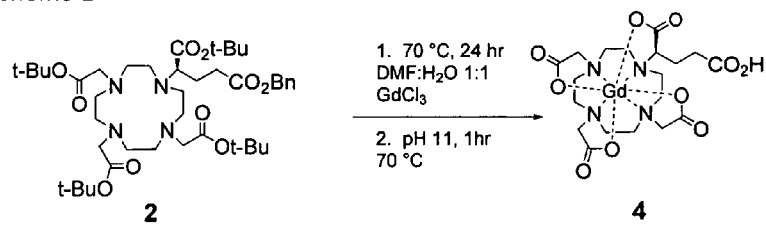
Scheme C
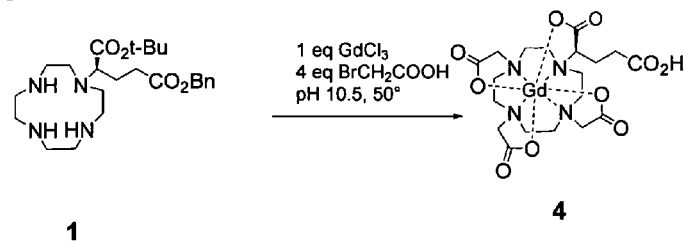
FIG. 6

2-(S)-Isomer Structures
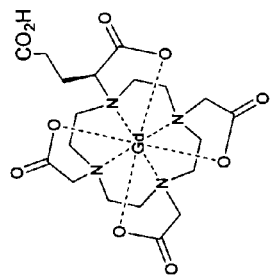
FIG. 7

OPTICALLY PURE AND ENRICHED ISOMERS OF CHELATING LIGANDS AND CONTRAST AGENTS

CROSS-REFERENCE TO RELATED APPLICATIONS

This application is a continuation of U.S. patent application Ser. No. 10/850,134 filed May 5, 2004 now abandoned and claims priority under 35 U.S.C. §119(e) to U.S. Provisional Application Ser. No. 60/473,369, filed on May 23, 2003, both of which are incorporated by reference in their entirety herein.

TECHNICAL FIELD

This invention relates to organic chelating ligands, including organic chelating ligand compositions enriched in a particular optical isomer, that are useful for preparing MRI contrast agents, and methods for synthesizing the same.

BACKGROUND

Complexes between gadolinium or other paramagnetic metal ions and organic chelating ligands are widely used as magnetic resonance (MR) contrast agents. Typically, a gadolinium contrast agent increases MR contrast by increasing the nuclear magnetic relaxation rates of water protons that are accessible to the contrast agent during MRI (Caravan, P., et al., *R. B. Chem. Rev.* 99, 2293 (1999)). The relaxation rate of these protons increases relative to water protons that are not accessible to the contrast agent. This change in relaxation rate leads to improved contrast of the images. In addition, this increase in relaxivity within a specific population of water molecule protons can result in an ability to collect more image data in a given amount of time, resulting in an improved signal to noise ratio.

Because MR contrast agents are treated as drugs by regulatory agencies (e.g., FDA), they undergo extensive clinical testing to assure efficacy and safety. In this regard, certain drugs, e.g., thalidomide, have been shown to have differing safety and/or efficacy profiles depending on whether the drug is an enantiomeric mixture of isomers, or is an optically pure or optically enriched isomer composition (e.g., preferentially the R or S isomer at a particular stereocenter). Thus, it would be useful to have methods to prepare and purify optically enriched or optically pure MRI contrast agent compositions, including those capable of demonstrating increased relaxivity in vitro and in vivo.

SUMMARY

The invention is based on the discovery that organic chelating ligands, including optical isomers of organic chelating ligands, can be synthesized in high yield and in high optical purity using inexpensive processes from readily available starting materials. Certain reaction processes described herein may be prepared in one reaction vessel and/or without purification of intermediates. The resultant organic chelating ligands can be used to prepare optically enriched or optically pure MRI contrast agent compositions, which may exhibit increased relaxivity both in vitro and in vivo. In addition, the organic chelating ligands and MRI contrast agents can be used to prepare targeted MRI contrast agents, e.g., for imaging targeted areas of the body, including thrombi, atherosclerotic lesions, atherosclerotic plaque, the myocardium, and the vasculature.

Accordingly, in one aspect, the invention provides organic chelating ligands, organic chelating ligand precursors, metal chelates, and active esters thereof, and composition comprising the same. An organic chelating ligand can have a formula selected from the group consisting of:

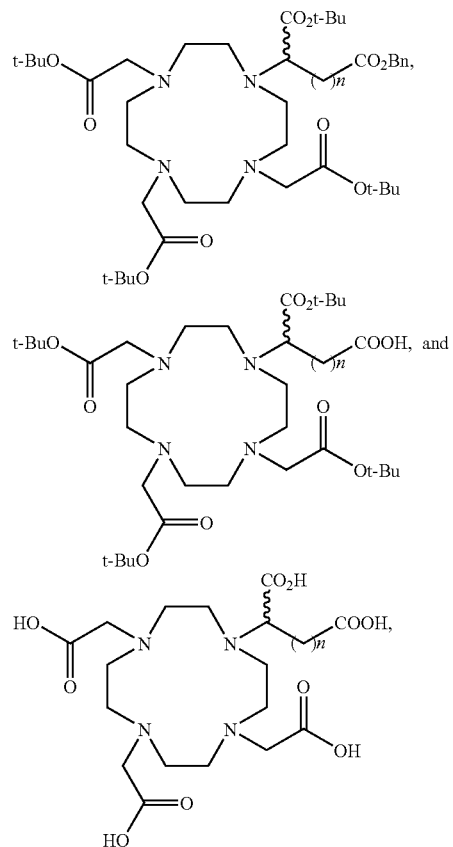

where n can range from 1 to 4, and where the chelating ligand (or composition comprising the same) can have an enantiomeric excess of greater than 50% of an (R) isomer or an (S) isomer at the 2 position of the chelating ligand. In certain cases, n can be 2. The enantiomeric excess of the (R) or the (S) isomer at the 2 position can be greater than 85%, greater than 90%, greater than 95%, or about 97% or greater.

A metal chelate or composition comprising the same can have a structure:

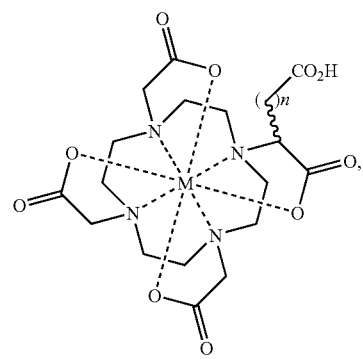

where the metal chelate (or composition comprising the same) can have an enantiomeric excess of greater than 50% of an (R) or (S) isomer at the 2 position. N can range from 1 to 4, and in certain cases is preferably 2. M can be selected from the group consisting of: Gd(III), Fe(III), Mn(II), Mn(III), Cr(III), Cu(II), Dy(III), Ho(III), Er(III), Eu(III), Tb(II), Tb(III), Ce(III), Pr(III), Yb(III), Tm(III), Nd(III), and Tb(IV). In certain cases, M is Gd(III). The enantiomeric excess can be greater than 85%, greater than 90%, greater than 95%, or about 97% or greater.

In another aspect, the invention provides MRI contrast agents and compositions comprising the same. An MRI contrast agent can include a metal chelate, as described above. An MRI contrast agent can optionally include one or more TBMs, Ls, or scaffolds. In certain cases, an MRI contrast agent can include a TBM conjugated through linkers to four metal chelates. The invention also provides chelating ligands and contrast agents useful for MR imaging of clots and other areas where fibrin is associated, and compositions including the same. For example, a composition can include the structure of Compound 26, 28, or 30, where the composition has an enantiomeric excess of greater than 50% (or greater than 85%, greater than 90%, greater than 95%, or about 97% or greater) of an (R) or (S) isomer at the 2 position of each conjugated chelating ligand or metal chelate, as appropriate.

The invention also provides organic chelating ligand precursors. An organic chelating ligand precursor (or composition comprising the same) can have a structure selected from the group consisting of:

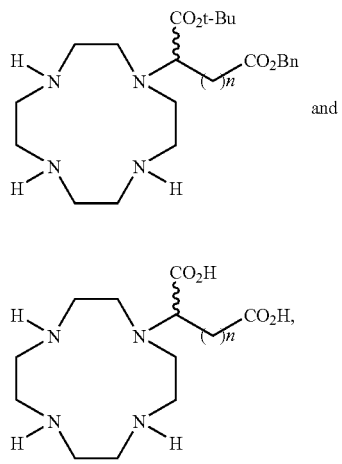

where n can range from 1 to 4, and where the composition has an enantiomeric excess of greater than 50% of an (R) isomer or (S) isomer at the 2 position. N can be preferably 2. In certain cases, the enantiomeric excess can be greater than 85%, greater than 90%, greater than 95%, or about 97% or greater.

In another aspect, the invention provides methods for synthesizing organic chelating ligands, organic chelating ligand precursors, and metal chelates. The method can yield an enantiomeric excess of more than 50%, or more than 85%, or more than 90%, or more than 95%, or about 97% or more, of the (R) or (S) isomer at the 2 position of the organic chelating ligand, the organic chelating ligand precursor, or the metal chelate, respectively.

The method includes:
a) reacting a starting material compound having the structure:

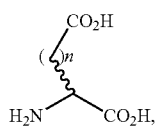

the starting material compound having an L or D stereochemistry at the Cα carbon, where n can range from 1 to 4, to form a lactone;
b) opening the lactone to yield a hydroxy-dioic acid ester;
c) activating the hydroxy group of the hydroxy-dioic acid ester; and
d) reacting the activated hydroxy group with an amine compound under conditions capable of alkylating the amine compound to form an organic chelating ligand precursor.

The lactone can be formed by subjecting the starting material compound to acidic conditions and/or a diazidization reaction. The temperature can be in the range from about −1 to about +20° C. The lactone can be opened using basic conditions, e.g., a pH greater than about 9. In certain cases, the pH can be greater than about 10, greater than about 11, or greater than about 12. The activating group can be a mesylate, tosylate, nosylate, triflate, or halide moiety. The amine compound can include one or more amine moieties, and at least one of the amine moieties of the amine compound is alkylated. The amine compound can be alkylated at 1 to 5 positions, such as 1, 2, 3, 4, or 5 positions. The amine compound can be, without limitation, cyclen, ethylenediamine, or diethylenetriamine. The resultant organic chelating ligand precursor has itself one or more amine moieties.

The method can further include converting the organic chelating ligand precursor to an organic chelating ligand. The conversion can include providing a carboxylic acid ester having a leaving group located at the α-carbon, and reacting the carboxylic acid ester with the organic chelating ligand precursor under conditions in which one or more of the amine moieties are alkylated to result in the organic chelating ligand. In addition, the method can further include chelating a metal ion to the organic chelating ligand to form a metal chelate.

The invention further provides a method for converting an organic chelating ligand that has one or more carboxylic acid esters to a metal chelate. The method includes the steps of:
a) providing the organic chelating ligand;
b) deprotecting one or more of the one or more carboxylic acid esters of the organic chelating ligand to yield one or more carboxylic acid moieties; and
c) chelating a metal ion to result in the metal chelate;
where the deprotection and the chelating steps are performed without purification of intermediates. The method may be performed in one reaction vessel.

The invention further provides a method for converting an organic chelating ligand precursor to a metal chelate comprising:
a) providing the organic chelating ligand precursor, the organic chelating ligand precursor having one or more amines;
b) providing a carboxylic acid ester having a leaving group located at the α-carbon;
c) reacting the carboxylic acid ester with the organic chelating ligand precursor under conditions in which one or more amines of the organic chelating ligand precursor are alkylated to form an organic chelating ligand; and d) chelating a metal ion to the organic chelating ligand to result in a metal chelate; where the reacting and the chelating steps are performed without purification of intermediates. The method may be performed in one reaction vessel.

Activated esters of an organic chelating ligand (and compositions comprising the same) are also provided. An activated ester of an organic chelating ligand can have a structure selected from the group consisting of:

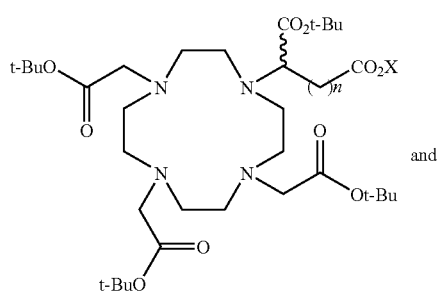

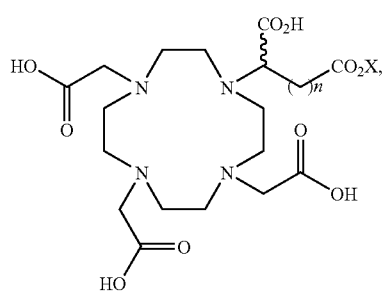

where n can range from 1 to 4. X can be selected from the group consisting of:

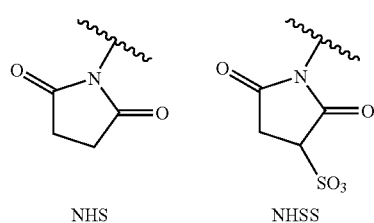

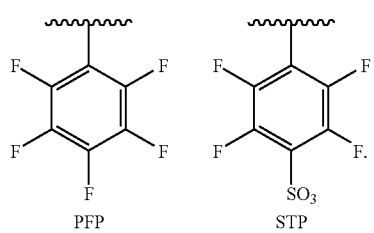

The composition can have an enantiomeric excess of greater than 50%, or greater than 85%, or greater than 90%, or greater than 95%, or about 97% or more of an (R) or (S) isomer at the 2 position of the chelating ligand.

An activated ester of a metal chelate and compositions including the same can have the following general formula:

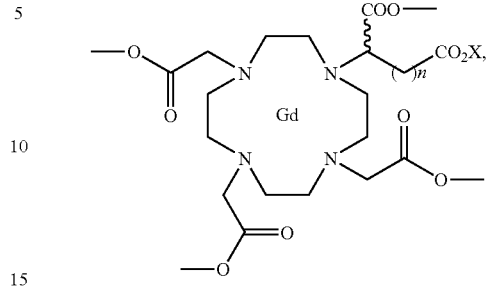

where n can range from 1 to 4 and X can be selected from the group consisting of:

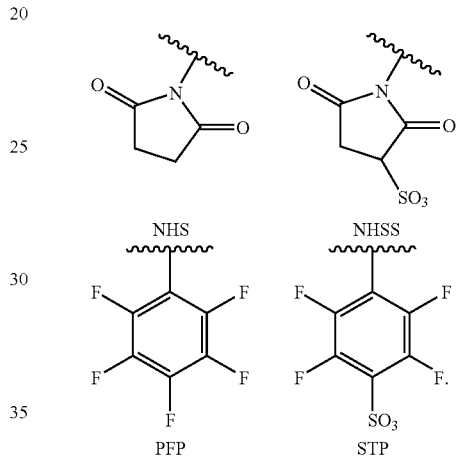

The composition can have an enantiomeric excess of greater than 50% (or greater than 85%, or greater than 90%, or greater than 95%, or about 97% or more) of an (R) or (S) isomer at the 2 position of the activated ester metal chelate. In certain cases, n can be 2.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 6 demonstrates three schemes for converting organic chelating ligands having carboxylic acid esters to metal chelates.

FIG. 7 demonstrates structures of certain embodiments of organic chelating ligands, ligand precursors, and metal chelates in the 2-(S) isomeric form.

DETAILED DESCRIPTION

Definitions

Figure 1A:
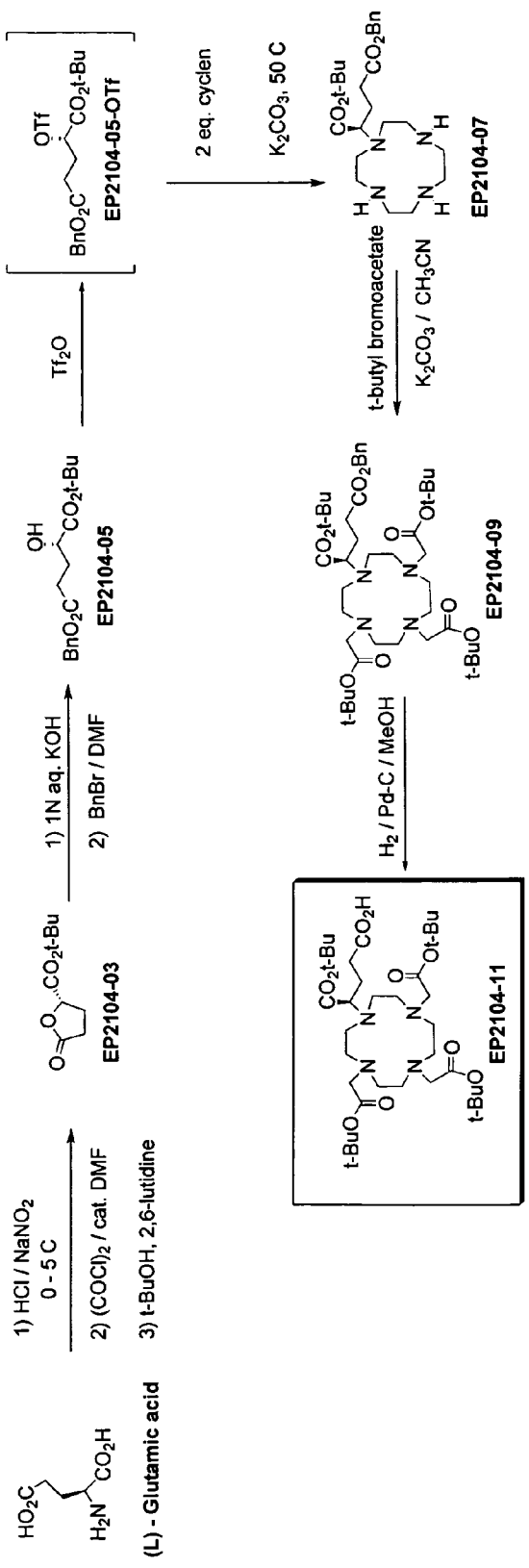
FIG. 1a is a synthetic scheme demonstrating an asymmetric synthesis of (R)-EP-2104-11, an organic chelating ligand, from L-glutamic acid. (S)-EP-2104-11 can be prepared in an analogous fashion with D-glutamic acid as the starting material.

Commonly used chemical abbreviations that are not explicitly defined in this disclosure may be found in The American Chemical Society Style Guide, Second Edition; American Chemical Society, Washington, D.C. (1997), "2001 Guidelines for Authors" *J. Org. Chem.* 66(1), 24A (2001), "A Short Guide to Abbreviations and Their Use in Peptide Science" *J. Peptide Sci.* 5, 465-471 (1999).

The terms "chelating ligand" may be used to refer to any polydentate ligand which is capable of coordinating a metal ion, either directly or after removal of protecting groups, or is a reagent, with or without suitable protecting groups, that is used in the synthesis of a contrast agent and comprises substantially all of the atoms that ultimately will coordinate the metal ion of the final metal complex. The term "chelate" refers to the actual metal-ligand complex, and it is understood that the polydentate ligand will eventually be coordinated to a medically useful metal ion.

The term "optically enriched" as used herein refers to the presence of an enantiomeric excess of either an R or an S isomer at a given stereocenter of a molecule in a composition. "Enantiomeric excess" is defined as |F(R)−F(S)| for a mixture of (R) and (S) enantiomers, with the composition given as the mole or weight fractions F(R) and F(S), where F(R)+F(S)=1. The percent enantiomer excess is given by 100|F(R)−F(S)|). Enantiomeric excess is frequently abbreviated as e.e. "Optically pure" as used herein means that the composition includes only a single isomer at a given stereocenter.

The term "specific binding affinity" as used herein refers to the capacity of a contrast agent to be taken up by, retained by, or bound to a particular biological component to a greater degree than other components. Contrast agents that have this property are said to be "targeted" to the "target" component. Contrast agents that lack this property are said to be "non-specific" or "non-targeted" agents. The specific binding affinity of a binding group for a target is expressed in terms of the equilibrium dissociation constant "Kd."

The term "relaxivity" as used herein refers to the increase in either of the MRI quantities 1/T1 or 1/T2 per millimolar (mM) concentration of paramagnetic ion or contrast agent, which quantities may be different if the contrast agent contains a multiplicity of paramagnetic ions, wherein T1 is the longitudinal or spin-lattice, relaxation time, and T2 is the transverse or spin-spin relaxation time of water protons or other imaging or spectroscopic nuclei, including protons found in molecules other than water. Relaxivity is expressed in units of $mM^{-1}s^{-1}$.

The terms "target binding" and "binding" for purposes herein refer to non-covalent interactions of a contrast agent with a target. These non-covalent interactions are independent from one another and may be, inter alia, hydrophobic, hydrophilic, dipole-dipole, pi-stacking, hydrogen bonding, electrostatic associations, or Lewis acid-base interactions.

As used herein, all references to "Gd," "gado," or "gadolinium" mean the Gd(III) paramagnetic metal ion.

Organic Chelating Ligands

Optically pure organic chelating ligands, metal chelates, and MRI contrast agents, and optically enriched compositions including an enantiomeric excess of a particular stereoisomer of organic chelating ligands, metal chelates, and MRI contrast agents are described herein. Methods are also provided for preparing an enantiomeric excess of either the (R) or the (S) isomer of the described organic chelating ligands. The resultant chelating ligands can be used to prepare non-specific metal chelates. In other cases, chelating ligands or metal chelates may be modified to incorporate one or more target binding moieties (TBMs). Chelating ligands having target binding moieties allow the chelating ligands (and metal chelates) to be targeted to various sites in vivo.

Typically, organic chelating ligand compositions have an enantiomeric excess of an (R) or an (S) isomer at a particular stereocenter. For example, there may be greater than 50%, e.g., greater than 85%, 90%, 95%, 96%, 97%, 98%, or 99% enantiomeric excess of the (R) or (S) isomer at a particular stereocenter. In certain cases, there may be 100% enantiomeric excess of a particular isomer at a particular stereocenter. In other cases, there may be about 97% or more enantiomeric excess of an isomer at a particular stereocenter. In some embodiments, the stereocenter may be located at a carbon bonded to a metal-coordinating N of an organic chelating ligand, e.g., the 2 position relative to the coordinating N.

Organic chelating ligands optically pure as a 2-(R) isomer can have the general formula:

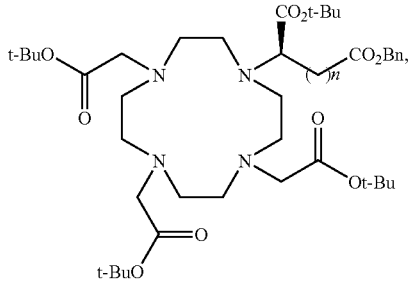

where n can range from 1 to 4. Typically, n can be 2, 3, or 4. In preferred cases, n is 2. One example of such an organic chelating ligand has the following formula:

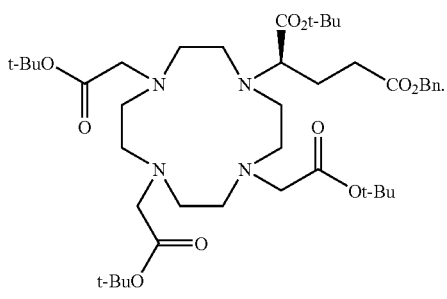

EP2104-09

As one of skill in the art will recognize, organic chelating ligands optically pure as the 2-(S) isomer will have the alternate stereochemistry at the 2 position.

Organic chelating ligands optically pure as a 2-(R) isomer can also have the general formula:

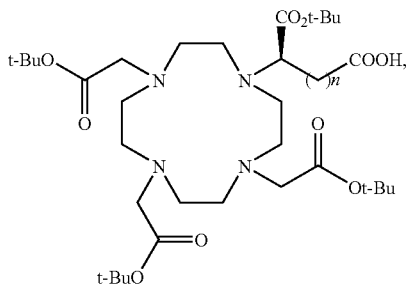

where n can range from 1 to 4 (e.g., 1, 2, 3, or 4). Preferably, n is 2. One example has the following structure:

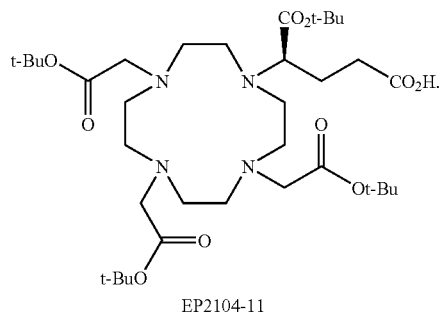

EP2104-11

As with the formula above, organic chelating ligands optically pure as a 2-(S) isomer will have the alternate stereochemistry at the 2 position.

Similarly, organic chelating ligands optically pure as a 2-(R) isomer can have the following general formula:

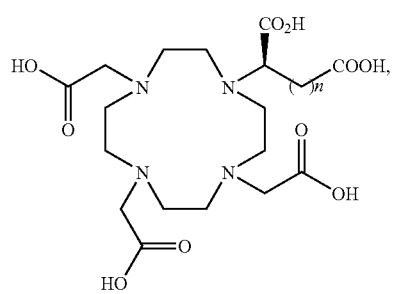

where n can range from 1 to 4, as indicated above. One example has the following formula:

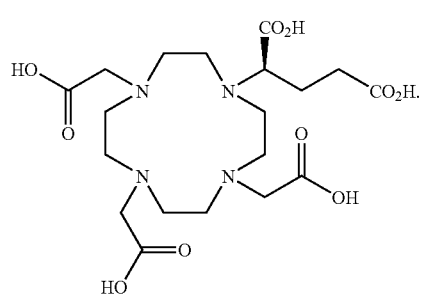

EP2104-14

As before, the 2-(S) isomers will have the alternate stereochemistry at the 2 position. As one of skill in the art will recognize from the above structures, organic chelating ligands may be protected or not at any of the carboxylic acid moieties, whether the moiety coordinates a metal ion or not. In addition, as one of skill in the art will recognize, organic chelating ligands can be protonated or unprotonated at one or more carboxylic acid moieties depending on the pH of the solution. All such structures, whether protected or not, protonated or not, and in any combination of protected and unprotected acids and protonated or unprotonated acids, are contemplated by the present invention. As described herein, pharmaceutically acceptable salts of all such structures are also contemplated by the present invention. For example, sodium salts, N-methyl glucamine salts, calcium salts, or mixtures thereof can be used.

Optically pure organic chelating ligand precursors and optically enriched organic ligand precursor compositions are also described. Organic chelating ligand precursors may lack one or more of the metal coordinating groups of the final organic chelating ligand but are capable of being chemically modified to result in an organic chelating ligand; see, e.g., the methods below. As with the organic chelating ligand compositions, the organic chelating ligand precursor compositions can have an enantiomeric excess of an (R) or an (S) isomer at a particular stereocenter. For example, there may be greater than 50% (e.g., greater than 85%, 90%, 95%, 96%, 97%, 98%, or 99%) enantiomeric excess of the (R) or (S) isomer at a particular stereocenter. In certain cases, there may be 100% enantiomeric excess of an isomer at a particular stereocenter. In other cases, there may be about 97% or more enantiomeric excess of an isomer at a particular stereocenter. The stereocenter may be located at a carbon bonded to a metal coordinating N of an organic chelating ligand precursor, e.g., the 2-position to the coordinating N.

Organic chelating ligand precursors optically pure as the 2-(R) isomer can have the following general formula:

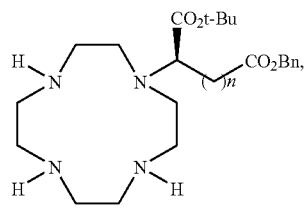

where n can range from 1 to 4, as described previously. The 2-(S) isomers will have the alternate stereochemistry at the 2 position. As one of skill in the art will recognize, either of the carboxylic acid moieties may be protected or not, and any combination of such protected and unprotected structures is contemplated by the present invention, including those shown by the general formula for the 2-(R) isomer below:

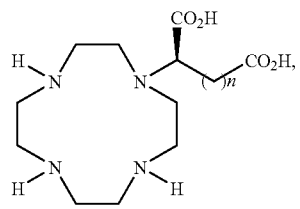

where n can range from 1 to 4, as indicated previously. The 2-(S) isomers will have the alternate stereochemistry at the 2 position.

Figure 2:
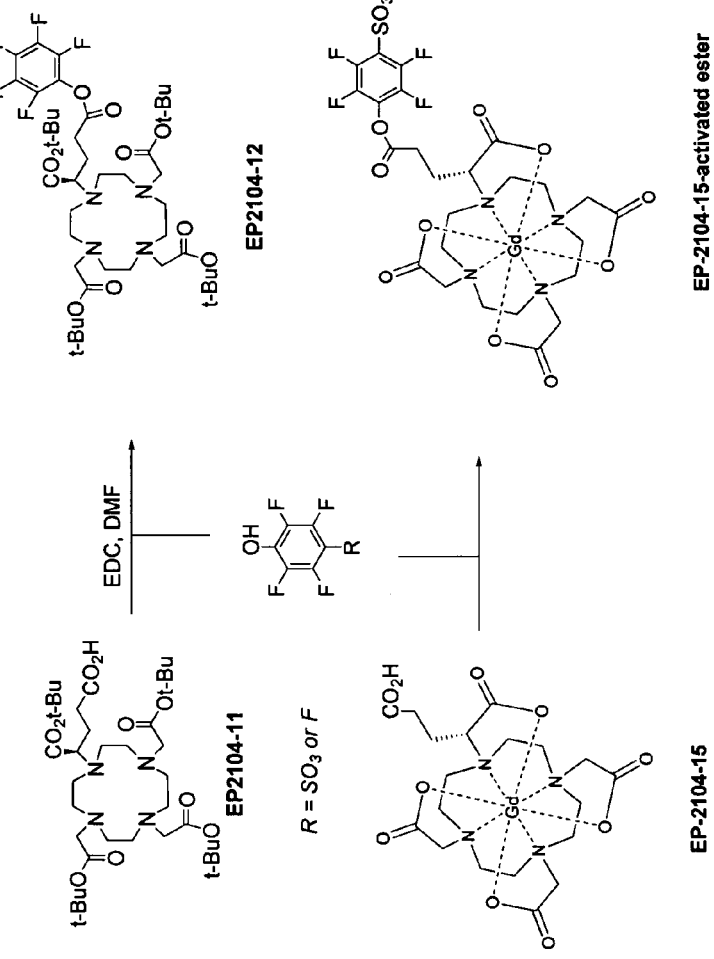
FIG. 2 is a synthetic scheme demonstrating an asymmetric synthesis of (R) or (S) activated esters of EP-2104-11 and EP-2104-15. Activated esters may be used in subsequent conjugation of the organic chelating ligand or metal chelate to other moieties, including target binding moieties and linking groups.
Figure 3:
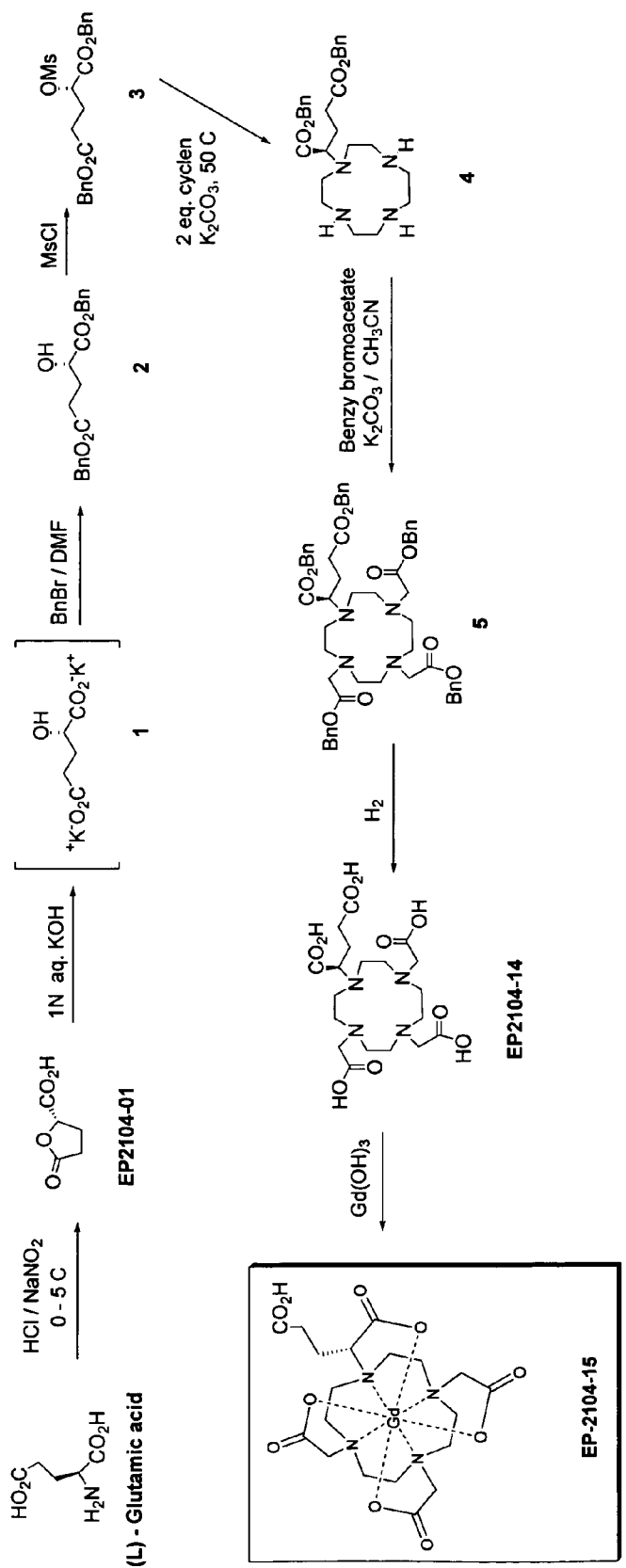
FIG. 3 is an alternative asymmetric synthetic scheme for preparing (R) or (S) EP-2104-14 (an organic chelating ligand) and (R) or (S) EP-2104-15 (a Gd(III) metal chelate). The (R) isomers employ L-glutamic acid as the starting material, while the (S) isomers employ D-glutamic acid as the starting material.
Figure 4:
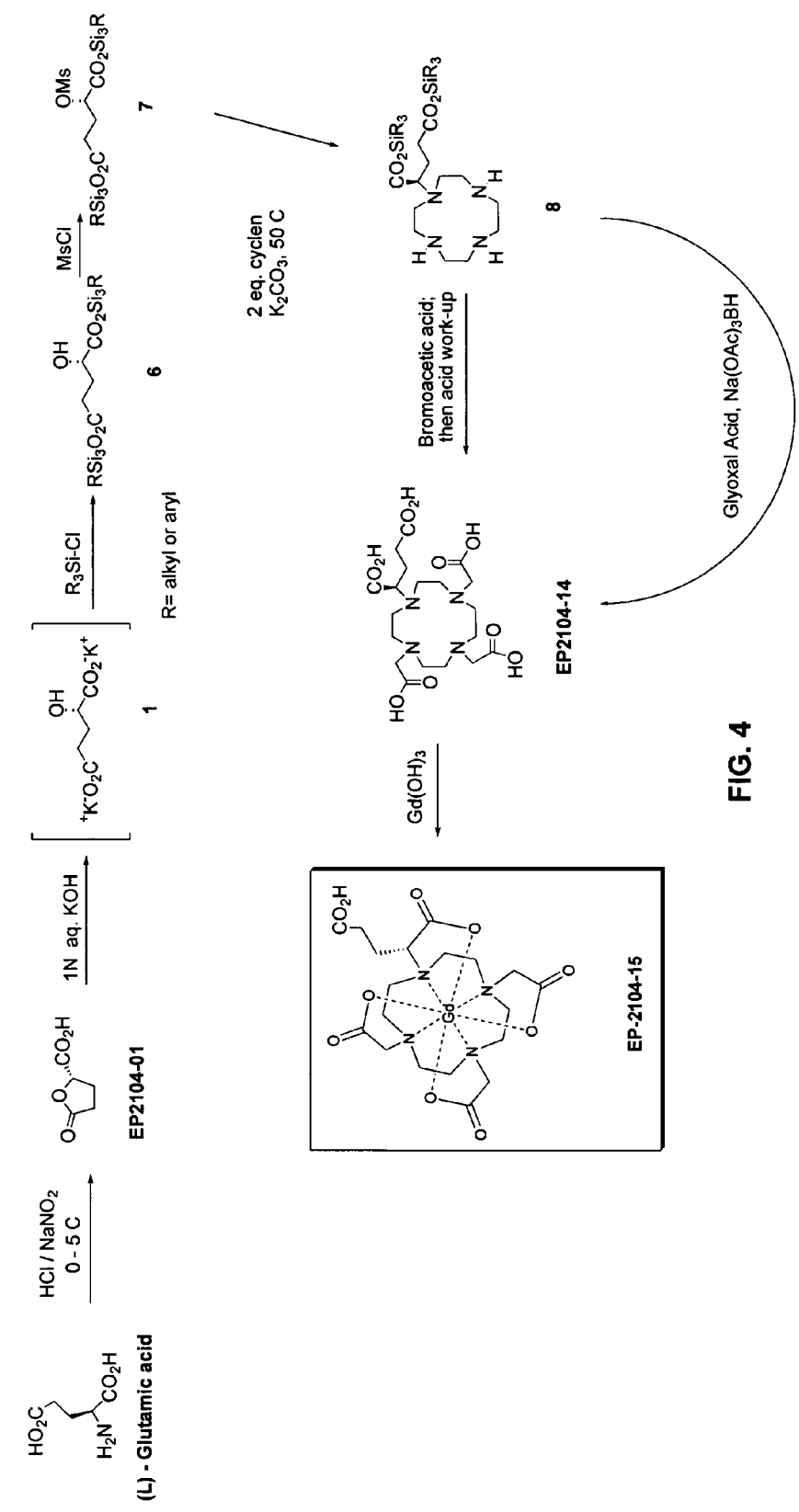
FIG. 4 is an alternative asymmetric synthetic scheme for preparing (R) or (S) EP-2104-14 (an organic chelating ligand) and (R) or (S) EP-2104-15 (a Gd(III) metal chelate). The (R) isomers employ L-glutamic acid as the starting material, while the (S) isomers employ D-glutamic acid as the starting material.
Figure 5:
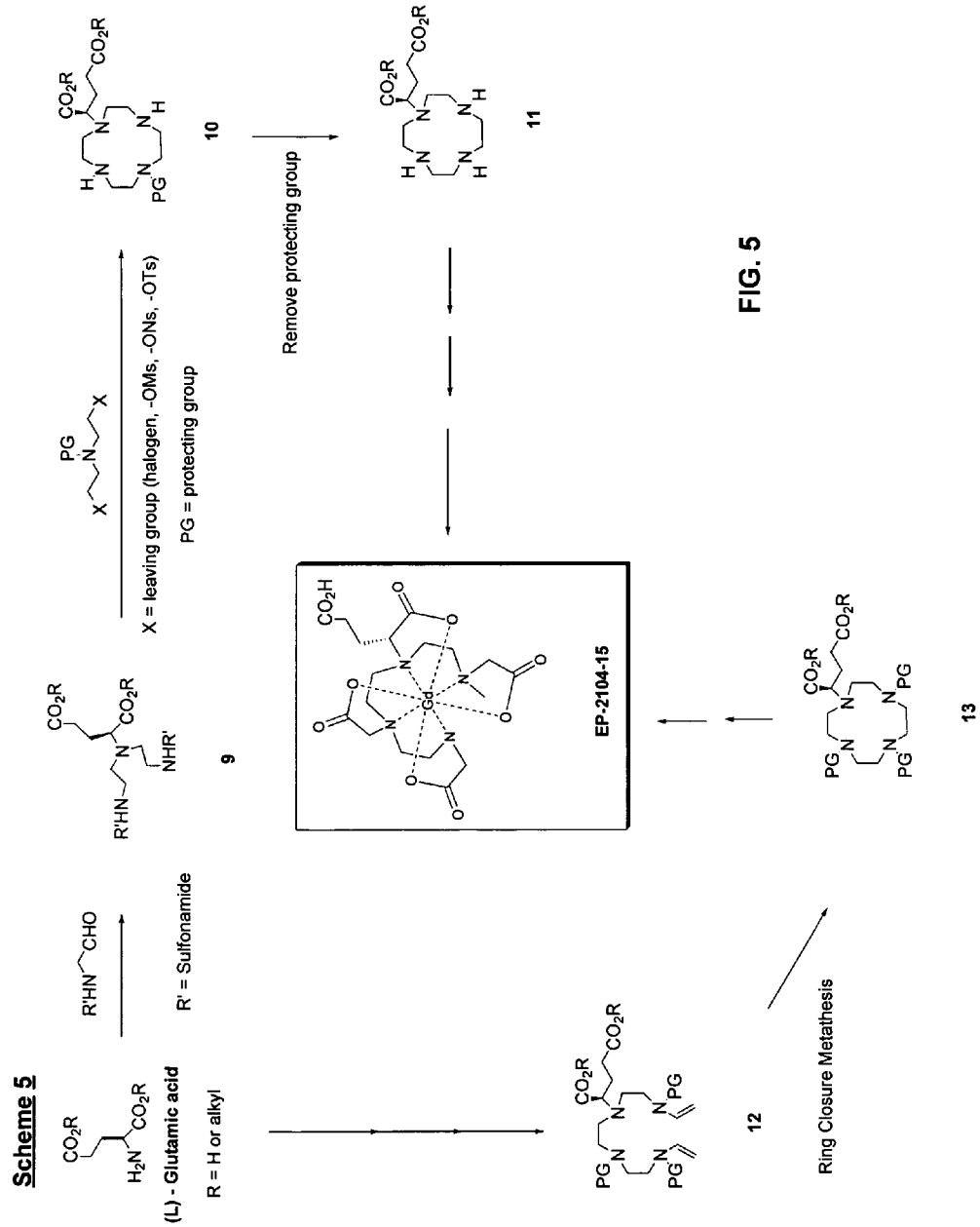
FIG. 5 is an alternative asymmetric synthetic scheme for preparing (R) or (S) EP-2104-15 (a Gd(III) metal chelate). The (R) isomers employ L-glutamic acid as the starting material, while the (S) isomers employ D-glutamic acid as the starting material.

Organic chelating ligands and organic chelating ligand precursors may be optionally derivatized with or conjugated to, e.g., functional moieties such as target binding moieties, linking groups, and scaffolds, as described more fully below. For example, any of the acetate chelating arms of an organic chelating ligand may be conjugated to Ls, TBMs, or scaffolds by methods known in the art. In certain cases, the organic chelating ligands and organic chelating ligand precursors may need to be modified to facilitate subsequent conjugation to TBMs, Ls, and scaffolds. Thus, carboxylic acid moieties may be esterified to active ester form, e.g., for subsequent conjugation or reaction with groups such as amines or alcohols on a TBM, L, or scaffold, to form amide and ester conjugations, respectively. In other cases, conjugation can occur through alkylation, e.g., through reductive amination reactions. Particular examples of activated ester forms of organic chelating ligands and metal chelates are set forth in FIG. 2.

An activated ester of an organic chelating ligand optically pure as the 2-(R) isomer can have a structure selected from the following general formulas:

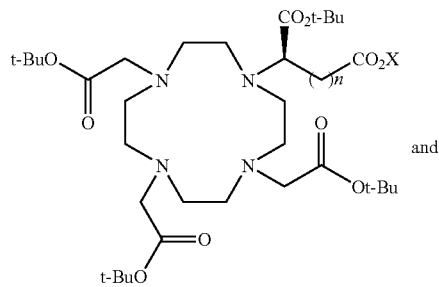

and

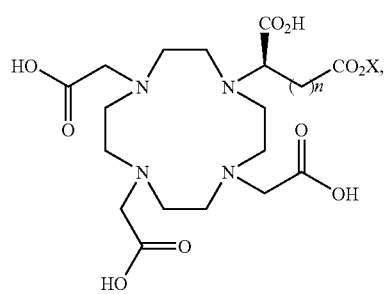

where n can range from 1 to 4, and X can be selected from the group consisting of:

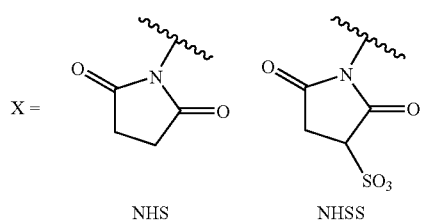

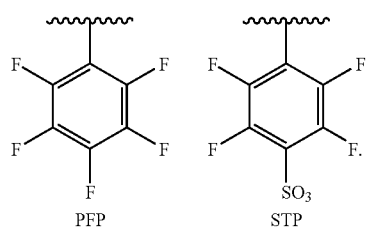

For example, one activated ester of an organic chelating ligand according to the present invention has the following formula:

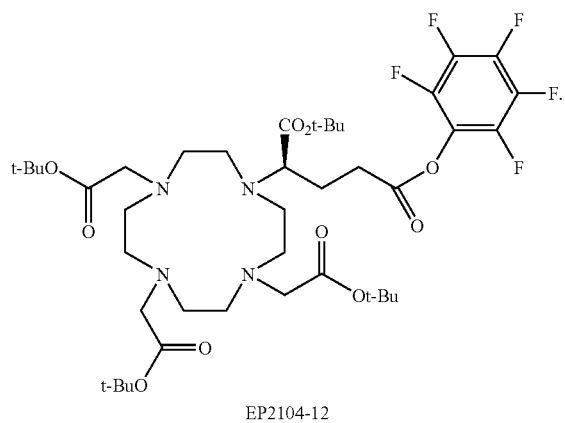

EP2104-12

The 2-(S) isomers will have the alternate stereochemistry at the 2 position. As one of skill in the art will recognize from the above structures, activated esters of organic chelating ligands may be protected or not at any of the carboxylic acid moieties, whether the moiety coordinates a metal or not. In addition, as one of skill in the art will recognize, activated ester organic chelating ligands can be protonated or unprotonated at one or more carboxylic acid moieties depending on the pH of the solution. All such structures, whether protected or not, protonated or not, and in any combination of protected and unprotected acids and protonated or unprotonated acids, are contemplated by the present invention. As described herein, pharmaceutically acceptable salts of all such structures are also contemplated by the present invention. For example, sodium salts, N-methyl glucamine salts, calcium salts, or mixtures thereof can be used.

Methods of Asymmetric Synthesis

Methods for preparing optically pure organic chelating ligand precursors, organic chelating ligands, and metal chelates are described, as well as methods for preparing optically enriched compositions comprising the same. The methods can yield an enantiomeric excess of greater than 50% (e.g., greater than 85%, 90%, 95%, 96%, 97%, 98%, or 99%) of a particular stereoisomer at a particular stereocenter. In certain cases, there may be 100% enantiomeric excess at a particular stereocenter; in other cases, there may be about 97% or more enantiomeric excess of an isomer at a particular stereocenter.

The method generally involves forming a lactone ring from a di-carboxylic acid starting material having a particular stereochemistry at a stereocenter, opening the lactone ring to yield a hydroxy-dioic acid ester, activating the hydroxy group, and reacting the activated hydroxy group with an amine compound under conditions in which the amine is alkylated at one or more amine moieties to form an organic chelating ligand precursor. The di-carboxylic acid can have a halide, alcohol, or amine moiety at an α position.

Typically, the stereochemistry of the starting material compound influences the final stereochemistry of the organic chelating ligand, precursor, or metal chelate. A di-carboxylic acid starting material compound for use in the invention can have the formula:

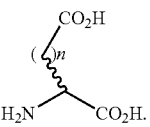

The compound can have an L-stereochemistry at a Cα carbon, or a D stereochemistry at the same. N can range from 1 to 4. As indicated previously, n can be 1, 2, 3, or 4, and in certain cases n can be 2. As can be seen, because the starting material compound can vary in side chain length, the size of the resultant lactone ring will vary. In certain embodiments, L- or D-glutamic acid can be used as the starting material compound. For example, if L-glutamic acid is used, an organic chelating ligand, precursor, or metal chelate having an R-stereochemistry at the 2 position (the position adjacent to the amine N to which the dioic-acid ester moiety is conjugated) can result. Alternatively, if D-glutamic acid is used, the S-stereoisomer can result.

Methods for forming a lactone ring are known in the art; see also FIGS. 1a and 1b and Examples, below. Typically, a di-carboxylic acid having or treated to have an appropriate leaving group (e.g., halide, activated alcohol, activated amine) at the α carbon can, under appropriate conditions (e.g., acidic conditions), form the lactone. For example, a diazidization reaction to form the lactone can occur if an amine is located in the α position, as shown above. Appropriate reaction conditions include treatment with $NaNO_2$ under acidic conditions. The temperature of the lactone ring-forming step can affect the yield, quality, and enantiomeric excess (ee) of the product. Typically, the temperature is maintained in a range from about −10 to about +20° C., or from about −5 to about +5° C., or from about 0 to 5° C.

Figure 1B:
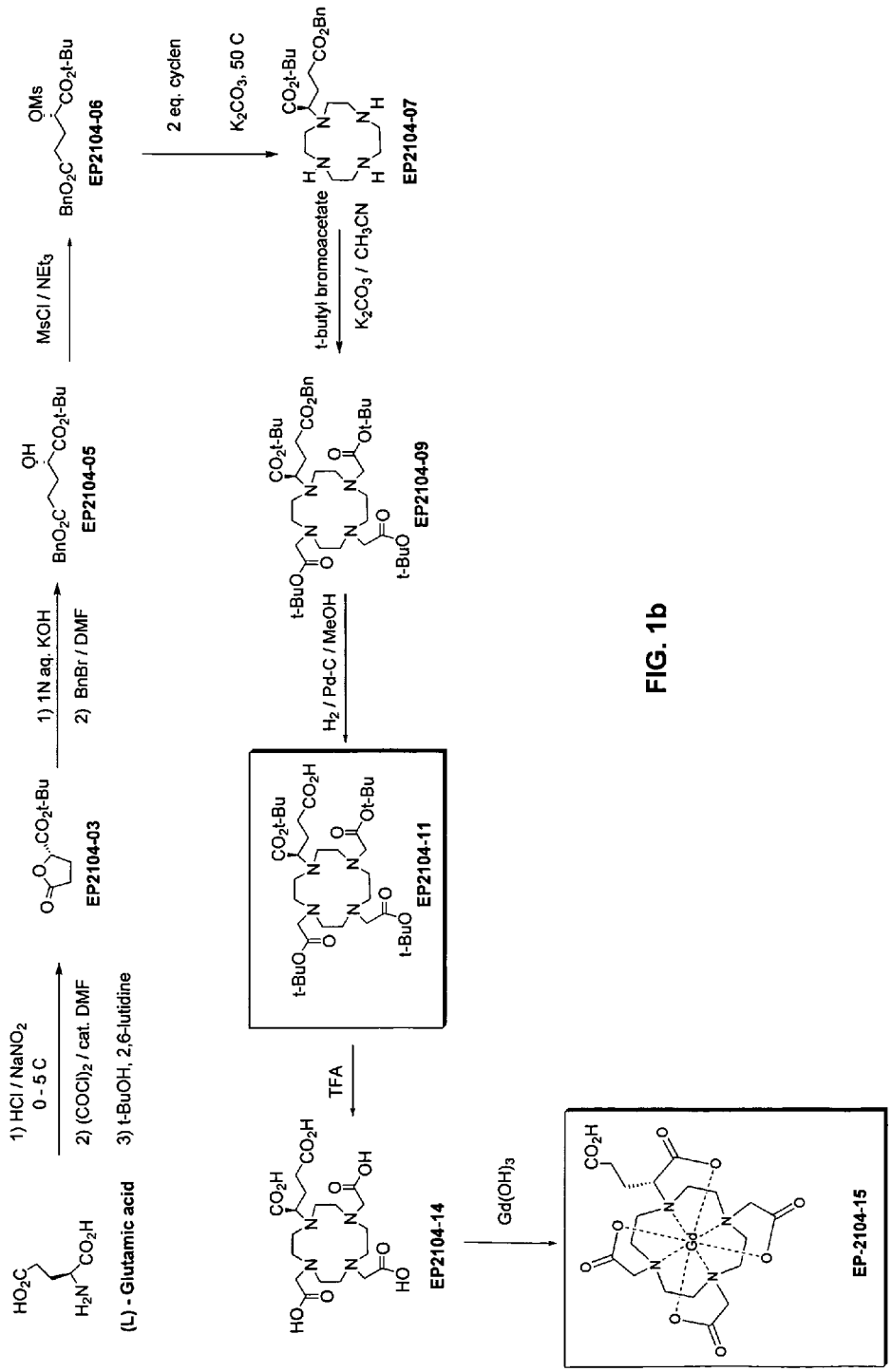
FIG. 1b is an alternative asymmetric synthetic scheme for preparing, among other things, (R) or (S) EP-2104-11 (an organic chelating ligand) and (R) or (S) EP-2104-15 (a Gd(III) metal chelate). The synthesis of the (R) isomers is shown with L-glutamic acid as the starting material. The (S) isomers can be prepared in an analogous fashion with D-glutamic acid as the starting material.

The lactone ring is then opened, e.g., with methods as set forth in FIGS. 1a and 1b and the Examples or as known to those of skill in the art, to form a hydroxy-dioic acid ester. The lactone can be opened using basic conditions, e.g., a pH greater than about 9. In certain cases, the pH can be greater than about 10, greater than about 11, or greater than about 12. The hydroxy group is activated, e.g., by reaction with an activating group. The activating group can be any of those known to those of skill in the art. Examples of activating groups include mesylate, tosylate, nosylate, triflate, and halide moieties. In certain cases, triflate or mesylate is preferably used. In other cases, bromide is used. The activated hydroxy compound is reacted with an amine compound under conditions in which the amine compound is alkylated at one or more amine moieties to yield the organic chelating ligand precursor. The conditions can be basic conditions, e.g., $K_2CO_3$. The temperature can range from about 30 to about 70° C.; in some cases the temperature is about 50° C. The resultant organic chelating ligand precursor can itself include one or more amine moieties, e.g., 1, 2, 3, 4, 5, 6, or 7 amine moieties.

Generally, the amine compound is a polyamine, and can be a linear or cyclic polyamine compound, e.g., cyclen, ethylenediamine, diethylenetriamine, triethylenetetramine, tetraethylenepentamine, and derivatives thereof. In certain cases, cyclen is preferred. In other cases, diethylenetriamine is preferred. Other polyamine compounds suitable for inclusion in the method are generally known to those of skill in the art. Conditions for alkylating amines are also generally well known to those of skill in the art; see, e.g., FIGS. 1a, 1b, 2-6, and Examples. Typically the amine compound is alkylated at 1 to 5 positions, e.g., 1, 2, 3, 4, or 5 positions. In certain cases, the amine compound is alkylated at 1 position.

The reaction sequence of activating the hydroxy group and reacting the activated hydroxy group with an amine compound may be performed either step-wise with purification of intermediates or step-wise with no purification of intermediates. The reaction sequence may be performed in one reaction vessel.

The precursor can then be converted to an organic chelating ligand, e.g, by reacting it with a carboxylic acid ester having a leaving group (e.g., halide) located at the α-carbon under conditions in which one or more amines of the precursor are alkylated (e.g., 1, 2, 3, 4, 5, 6, or 7 of the amines are alkylated). The conditions may include conditions to activate the one or more amines, such as basic conditions (e.g., $K_2CO_3$). Typically 2, 3, or 4 amines are alkylated. Finally, organic chelating ligands can be converted to metal chelates by chelating a metal ion, e.g., by methods described below. In certain embodiments, an organic chelating ligand precursor can be converted directly to the metal chelate, see below, without purification of intermediates. Such a reaction can be performed in one reaction vessel.

Typically, the methods yields an enantiomeric excess of more than 50% (e.g., more than 85%, 90%, 95%, 96%, 97%, 98%, or 99%) of an (R) or (S)-isomer at the 2 position, or in some cases, about 97% or more e.e. of the (R)-isomer or (S)-isomer at the 2 position of the organic chelating ligand precursor, organic chelating ligand, or metal chelate, respectively. See, e.g., FIGS. 1a, 1b, 2-5 and Examples, below.

Preparation of Metal Chelates and Properties of Metal Chelates

Organic chelating ligands are capable of binding one or more metal ions to result in a metal chelate. Metal chelates can be prepared by methods well known in the art; see WO 96/23526, U.S. Pat. Nos. 6,406,297 and 6,515,113. Metal chelates can include lanthanide metal ions such as Gd(III), Fe(III), Mn(II), Mn(III), Cr(III), Cu(II), Dy(III), Ho(III), Er(III), Eu(III), Tb(II), Tb(III), Ce(III), Pr(III), Yb(III), Tm(III), Nd(III), and Tb(IV). For MR applications, the metal ion can be Gd(III). The metal ion can be paramagnetic. Typically, because of the chemical nature of the chelating ligands, the metal ion is tightly bound by the chelating ligand, and physiologically compatible metal chelates can be made. The formation constant, $K_f$, of a chelating ligand for a metal ion is an indicator of binding affinity, and is typically discussed with reference to a log $K_f$ scale. Physiologically compatible metal chelates can have a log $K_f$ ranging from 15 to about 25 $M^{-1}$. Methods for measuring $K_f$ are well known in the art; see, e.g., Martell, A. E., Motekaitis, R. J., *Determination and Use of Stability Constants*, 2d Ed., VCH Publishers, New York (1992).

Metal chelates and metal chelate compositions are also provided. A metal chelate or metal chelate composition can demonstrate an enantiomeric excess of more than 50% (e.g., more than 85%, 90%, 95%, 96%, 97%, 98%, or 99%) of an (R) or (S)-isomer at the 2 position, or in some cases, about 97% or more e.e. of the (R)-isomer or (S)-isomer at the 2 position.

For example, metal chelates optically pure as the (R)-isomer at the 2 position can have the following general formula:

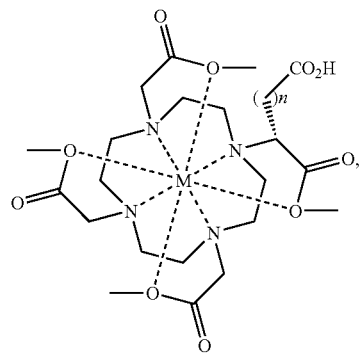

where n can be from 1 to 4, as described above, and where M can be any of the metals set forth previously. In certain cases, n can be 2. The S-isomers will have the alternate stereochemistry at the 2-position. As one of skill in the art will recognize, the carboxylic group stereospecifically attached to the chelating acetate group at the 2-position may or may not be protonated depending on the solution pH.

For example, one Gd(III) metal chelate optically pure as the (R)-isomer can have the formula:

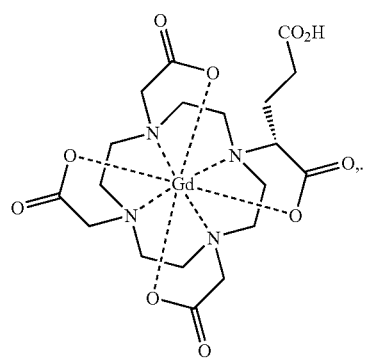

EP-2104-15

As with the organic chelating ligands and organic chelating ligand precursors, metal chelates may be optionally derivatized with or conjugated to, e.g., functional moieties such as target binding moieties, linking groups, and scaffolds. For example, any of the acetate chelating arms of a metal chelate may be conjugated to an L, TBM, or scaffold by methods known in the art. In certain cases, the metal chelate may need to be modified to facilitate subsequent conjugation to a TBMs, L, or scaffold. Thus, carboxylic acid moieties may be esterified to active ester form, e.g., for subsequent conjugation or reaction with groups such as one or more amines or alcohols on a TBM, L, or scaffold(to form amide and ester conjugations, respectively. In other cases, conjugation can occur through alkylization, e.g., through reductive amination reactions.

As with the organic chelating ligands set forth previously, the metal chelates can also be converted to an activated ester form. Activated esters of chelates and compositions including the same can demonstrate an enantiomeric excess of more than 50% (e.g., more than 85%, 90%, 95%, 96%, 97%, 98%, or 99%) of an (R) or (S)-isomer at the 2 position, or in some cases, about 97% or more e.e. of the (R)-isomer or (S)-isomer at the 2 position.

Activated ester metal chelates optically pure as the (R) isomer can have a structure having the following general formula:

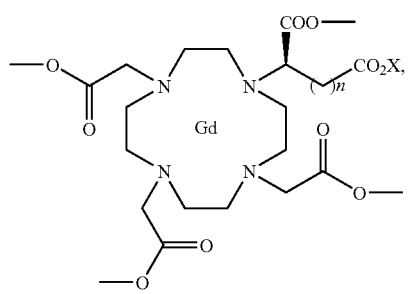

where n can range from 1 to 4 and X can be selected from the group consisting of:

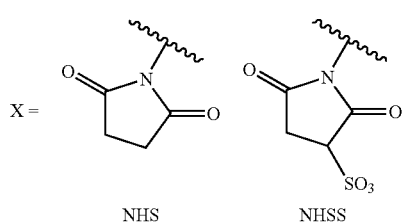

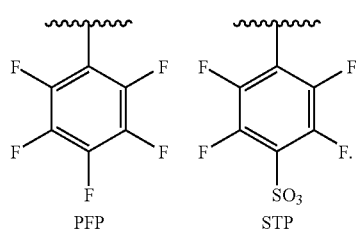

The (S) isomer will have the alternate stereochemistry at the 2 position. Two examples of activated ester metal chelates optically pure as the (R) isomer have the following formulas:

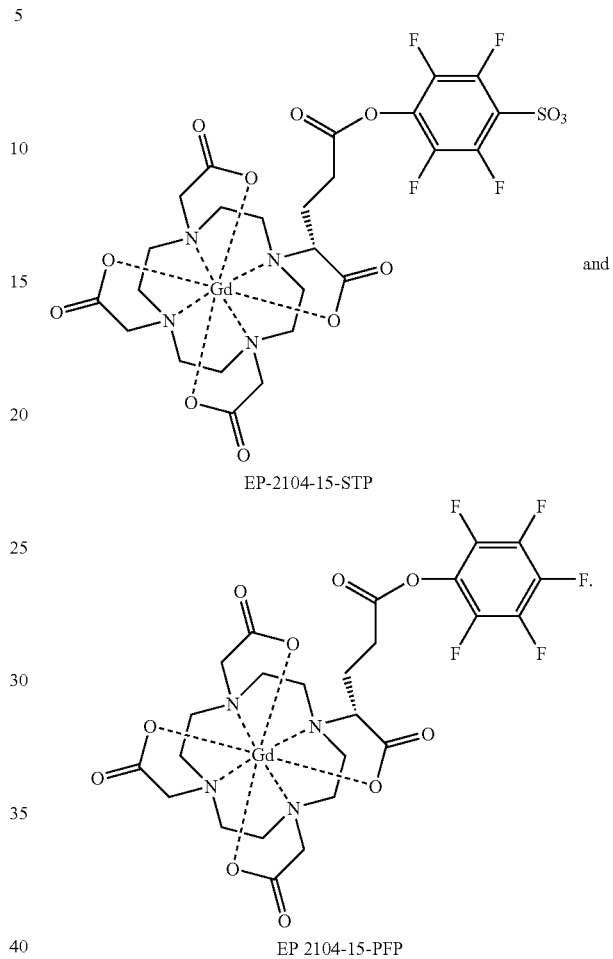

In certain cases, one or more activated ester metal chelates can be conjugated to a target binding moiety (TBM) through a linker. For example, an activated ester metal chelate can be reacted with a linker having one or more free amine moieties under conditions to yield one or more metal chelates bound to the linker on the TBM through an amide moiety. See Example 10, below.

As one of skill in the art will recognize from the above structures, metal chelates and activated ester metal chelates may be protected or not at one or more of the carboxylic acid moieties, provided that the resultant chelate is physiologically compatible. In addition, they can be protonated or unprotonated at one or more carboxylic acid moieties. All such structures, whether protected or not, protonated or not, and in any combination of protected and unprotected acids and protonated or unprotonated acids, are contemplated by the present invention. As described herein, pharmaceutically acceptable salts of all such structures are also contemplated by the present invention. For example, sodium salts, N-methyl glucamine salts, calcium salts, or mixtures thereof can be used.

The relaxivity values of any of the metal chelates described above can be assessed to determine, for example, usefulness as MRI contrast agents. If the metal chelate incorporates a TBM, the relaxivity can be measured in the presence and absence of the target molecule. Methods for measuring relaxivity are well known in the art; see WO 96/23526 and Example 6A, below.

Metal chelates can also be evaluated for the mean residence time of water molecule(s) in the first (or higher) coordination sphere(s). The mean residence time of water molecules is the inverse of the water exchange rate and is dependent on temperature. The mean residence time of water in the coordination sphere of the metal chelates is preferably between 1 and 100 ns, or between 3 and 30 ns. $^{17}$O NMR can be used to evaluate the mean residence time of water molecules.

Luminescence lifetime measurements can be used to evaluate the number of water molecules bound to a metal chelate. Methods for measuring luminescence lifetimes are known in the art, and typically include monitoring emissive transitions of the chelate at particular wavelengths for lifetime determination, following by fitting of luminescence decay data.

Conversion of Protected Carboxylic Acid Ester Chelating Ligands and Protected Carboxylic Acid Ester Chelating Ligand Precursors to Metal Chelates As described above, metal chelate complexes are often synthesized by first synthesizing an organic chelating ligand containing one or more carboxylate (carboxylic acid) chelating moieties. The organic chelating ligand can also contain one or more carboxylic acid moieties that do not chelate the metal, e.g., as substituents on the ligand for conjugating the ligand to other moieties, such as target binding moieties or linking groups. See, e.g., structures of EP-2104-09, -11, -14, and -15. During synthesis, it is often necessary to protect one or more of these carboxylic acids as carboxylic acid esters (e.g., see FIGS. 1-6 above, and Examples below). Before the metal chelate complex can be prepared, certain of the esters must be deprotected: e.g., hydrolyzed by acid or base, or in the case of benzyl esters, hydrogenated. After deprotection, the organic chelating ligand is then typically reacted with the metal ion to form the metal chelate complex. Accordingly, another aspect of the invention is the finding that it is possible to deprotect carboxylic acid groups and chelate the metal simultaneously (e.g., without intermediate purification), rather than step-wise with intermediate purification. This eliminates one synthetic operation and also can eliminate the harsh acid or basic conditions accompanying ester hydrolysis. In addition, one can also similarly convert organic chelating ligand precursors having protected ester substituents to the metal chelate (see Example 7, Scheme C below).

In the method, an organic chelating ligand having one or more carboxylic acid esters is deprotected at one or more of the carboxylic acid ester moieties, and a metal ion is chelated to the deprotected organic chelating ligand to result in the metal chelate. The deprotection and chelating steps can be performed in one reaction vessel and with no purification of intermediates. Methods for deprotecting carboxylic acid esters and chelating a metal ion are set forth in FIG. 6 and the Examples, below.

Similarly, an organic chelating ligand precursor can be converted to a metal chelate in a single reaction vessel and with no purification of intermediates. An organic chelating ligand precursor having one or more amines is reacted with a carboxylic acid ester having a leaving group located at the α-carbon. The reaction is performed under conditions in which one or more of the amines are alkylated to yield the organic chelating ligand. A metal ion is chelated to the organic chelating ligand to result in a metal chelate. The reacting and chelating steps are performed in one reaction vessel and with no purification of intermediates, as set forth in FIG. 6 and the Examples, below.

Targeting Groups

Chelating ligands and metal chelates may be modified to incorporate one or more Target Binding Moieties (TBM). TBMs can include peptides, nucleic acids, or small organic molecules. TBMs allow chelating ligands and metal chelates to be bound to targets in vivo. Typically, a TBM has an affinity for a target. For example, the TBM can bind its target with a dissociation constant of less than 10 μM, or less than 5 μM, or less than 1 μM, or less than 100 nM. In some embodiments, the TBM has a specific binding affinity for a specific target relative to other physiologic targets.

TBMs can be synthesized and conjugated to the chelating ligands and metal chelates described herein by methods well known in the art, including standard peptide and nucleic acid synthesis methods; see, e.g., WO 01/09188, WO 01/08712, and U.S. Pat. Nos. 6,406,297 and 6,515,113. Typically, a TBM is covalently bound to the chelating ligand or metal chelate, and can be covalently bound through an optional Linker (L). A TBM may be located anywhere on a chelating ligand or metal chelate. For example, a TBM may be conjugated to the chelating ligand or metal chelate at a position that had been converted to an activated ester at a carboxylic acid moiety, see supra. Alternatively, the TBM may be conjugated at an acetate chelating moiety of a chelating ligand or metal chelate, e.g., at the methylene group of the acetate moiety; or at an ethylene carbon in the backbone of the chelating ligand or metal chelate (e.g., the ethylene carbons on DTPA or DOTA). Methods for conjugating chelating ligands and metal chelates with TBMs, including peptide TBMs, are described in U.S. patent application Ser. No. 10/209,183, entitled PEPTIDE-BASED MULTIMERIC TARGETED CONTRAST AGENTS, filed Jul. 30, 2002; see also U.S. Pat. No. 6,652,835.

Any ratio of TBMs to conjugated chelating ligand or metal chelate can be used. For example, a TBM can have 1, 2, 3, 4, 5, 6, 7, or 8 chelating ligands or metal chelates, which may be the same or different, conjugated thereto, optionally through the use of one or more linkers. In certain cases, a TBM can have 4 chelating ligands or metal chelates conjugated thereto (optionally through one or more linkers); see, for example, Compounds 26, 28, or 30 below. Alternatively, a chelating ligand or metal chelate can have 0, 1, 2, 3, 4, 5, 6, 7, or 8 TBMs, which may be the same or different, conjugated thereto. In other cases, a scaffold can be employed, as described in U.S. Pat. No. 6,652,835, to which 2 or more TBMs and 2 or more of the chelating ligands or metal chelates described herein can be conjugated, optionally through one or more linkers.

Chelating ligands having a TBM can be assayed for relaxivity values (as the metal chelate) in the presence or absence of the target, e.g., when bound or unbound to the target, respectively. Typically, a metal chelate having a TBM will exhibit a higher relaxivity when bound to a target because of the RIME effect (see, e.g., U.S. Pat. Nos. 4,899,755 and 4,880,008).

Typical targets include human serum albumin (HSA), fibrin, an extracellular component of myocardium (e.g., collagen, elastin, and decorin), or an extracellular component of a lesion (e.g., hyaluronic acid, heparin, chondroitin sulfate, dermatan sulfate, heparan sulfate, keratan sulfate, versican, and biglycan). TBMs for binding to HSA are well known in the art, and can include a variety of hydrophobic or amphiphilic moieties. For example, a TBM for binding HSA can have one of the following formulas:

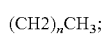

$(CH_2)_n CH_3$;

$(CH_2)_n Ph$;

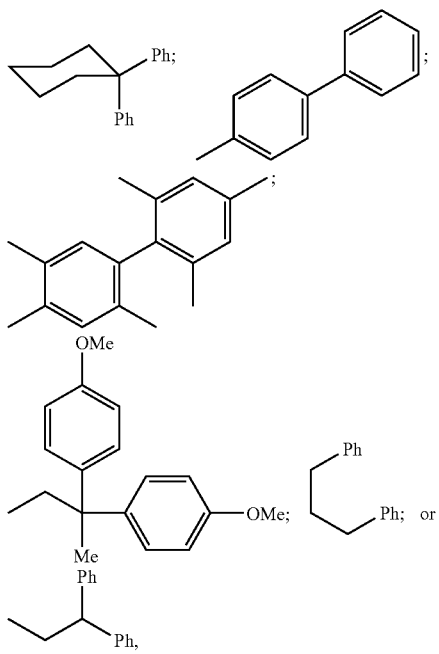

where n is 2 to 20 and Ph is phenyl. See, for example, WO 96/23526.

Useful TBMs for binding fibrin are described in U.S. patent application Ser. No. 10/209,183, entitled PEPTIDE-BASED MULTIMERIC TARGETED CONTRAST AGENTS, filed Jul. 30, 2002, published as U.S. Publication US-2003-0216320-A1, and incorporated herein by reference. For example, the following sequences can be used: W-dE-C-P(4-OH)-Y(3-Cl)-G-L-C-W-I-Q (SEQ ID NO:14), Y-dE-C-P(4-OH)-Y(3-Cl)-G-L-C-Y-I-Q (SEQ ID NO:15), Y-dE-C-P(4-OH)-Y(3-Cl)-G-L-C-W-I-Q (SEQ ID NO:16), W-dE-C-P(4-OH)-Y(3-Cl)-G-L-C-Y-I-Q (SEQ ID NO:17), W-dE-C-P(4-OH)-Y(3-Cl)-D-L-C-W-I-Q (SEQ ID NO:18), Y-dE-C-P(4-OH)-Y(3-Cl)-D-L-C-Y-I-Q (SEQ ID NO:19), Y-dE-C-P(4-OH)-Y(3-Cl)-D-L-C-W-I-Q (SEQ ID NO:20), W-dE-C-P(4-OH)-Y(3-Cl)-D-L-C-Y-I-Q (SEQ ID NO:21), F(4-OMe)-H-C-P(4-OH)-Y(3-Cl)-D-L-C-H-I-L (SEQ ID NO:22), Y-H-C-P(4-OH)-Y(3-Cl)-G-L-C-W-I-Q (SEQ ID NO:23), W-dE-C-P-Y(3-Cl)-G-L-C-W-I-Q (SEQ ID NO:24), W-dE-C-P(4-OH)-Y-G-L-C-W-I-Q (SEQ ID NO:25), and F-H-C-P-(4-OH)-Y(3-Cl)-D-L-C-H-I-L (SEQ ID NO:26).

TBMs for binding an extracellular component of a lesion include peptides having affinity for Hyaluronic Acid (HA). Peptides that have affinity for HA are known. For example, peptides that bind to HA from a random 12-mer phage peptide library have been isolated. See Mummert, M., Mohamedzadeh, M., Mummert, D., Mizumoto, N., and Takashima, A. J. Exp. Med. (2000) 769-779. One of these peptides, GAHWQFNALTVR (SEQ ID. NO:1), binds to HA with Kd~1 μM. As described herein, all peptides are written from their N to their C terminus. Other HA binding peptides include TSYGRPALLPAA (SEQ ID NO:2), MDHLAPTRFRPAI (SEQ ID NO:3), TLRAIWPMWMSS (SEQ ID NO:4), and IPLTANYQGDFT (SEQ ID NO:5).

In addition, peptides having affinity for HA can include a consensus binding motif found in many HA-binding peptides, including RHAMM, CD44, and the link protein. The consensus motif can be $B(X)_7$, where B is a basic residue (e.g., Lys, His or Arg) and X is a non acidic residue.

In other embodiments, a lesion-targeting peptide can have affinity for heparin, and can include a heparin-binding motif found in heparin-binding proteins. Heparin-binding motifs for inclusion in the peptides include XBBXBX or XBBBXXBX, where B is a basic residue (e.g., Lys, His, or Arg) and X is a non-acidic residue. For example, the heparin-binding peptide ACQWHRVSVRWG (SEQ ID NO:6) conforms to the XBBXXXBX sequence (Nielsen, P. K., Gho, Y. S., Hoffman, M. P., Watanabe, H., Makino, M., Nomizu, M., and Yamada, Y. J. Biol. Chem. (2000) 275, 14517-14523). Finally, the heparin sulfate/heparin interacting protein sequence (HIP) motif can also be included in a peptide. One example of such a motif is

CRPKAKAKAKAKDQTK. (SEQ ID NO: 7)

Useful TBMs for targeting an extracellular component of myocardium include peptides derived from the propolypeptide of von Willebrand factor, which is known to bind collagen. As used herein, all peptides are written from the N to C terminus. Additionally, peptides containing two or more cysteine residues can form disulfide bonds under non-reducing conditions. A peptide for targeting collagen can include the following general formula: $X_1-X_2-X_3-X_4-X_5-X_6-X_7-X_8-X_9-X_{10}$ (SEQ ID NO:8) where $X_1$ can be W, C, or A; $X_2$ can be R, C, or A; $X_3$ can be E, C, A, K, or T; $X_4$ can be P, C, or A; $X_5$ can be D, G, S, C, or A; $X_6$ can be F, R, C, or A; $X_7$ can be C, M, or A; $X_8$ can be A, E, or C; $X_9$ can be L, M, R, C, or A; and $X_{10}$ can be S, N, G, L, C, or A; where no more than 3 of $X_1-X_{10}$ are C or A, independently, and where the total number of C and A residues in $X_1-X_{10}$ is a maximum of 4. For example, a peptide can have the following sequences: WREPSFCALS (SEQ ID NO:9); WREPSFMALS (SEQ ID NO:10); and WREPGFCALS (SEQ ID NO:11).

Another example of a peptide that binds collagen has the following general formula: $X_1-X_2-X_3-X_4-X_5-X_6-X_7-X_8-X_9-X_{10}-X_{11}-X_{12}-X_{13}$ (SEQ ID NO:12) where $X_1$ can be W, C, or A; $X_2$ can be R, C, or A; $X_3$ can be E, C, A, K, or T; $X_4$ can be P, C, or A; $X_5$ can be D, G, S, C, or A; $X_6$ can be F, R, C, or A; $X_7$ can be C, M, or A; $X_8$ can be A, E, or C; $X_9$ can be L, M, R, C, or A; $X_{10}$ can be S, N, G, L, C, or A; $X_{11}$ can be C, M, or A; $X_{12}$ can be P, A, or C; and where $X_{13}$ can be K, Q, P, H, G, C, or A; where no more than 4 of $X_1-X_{13}$ are C or A, independently, and where the total number of C and A residues in $X_1-X_{13}$ is a maximum of 5.

A peptide for binding collagen can also have the following general formula: $X_1-X_2-X_3-X_4-X_5-X_6-X_7-X_8-X_9-X_{10}-X_{11}-X_{12}-X_{13}-X_{14}-X_{15}$ (SEQ ID NO:13) where $X_1$ can be V, I, C, or A; $X_2$ can be A, G, R, D, or C; $X_3$ can be W, C, or A; $X_4$ can be R, C, or A; $X_5$ can be E, C, A, K, or T; $X_6$ can be P, C, or A; $X_7$ can be D, G, S, C, or A; $X_8$ can be F, R, C, or A; $X_9$ can be C, M, or A; $X_{10}$ can be E, A, or C; $X_{11}$ can be L, C, A, M, or R; $X_{12}$ can be S, C, A, N, G, or L; $X_{13}$ can be C, M, or A; $X_{14}$ can be P, A, or C; and $X_{15}$ can be K, Q, P, H, G, C, or A; where no more than 4 of $X_1-X_{15}$ are C or A, independently, and where the total number of C and A residues in $X_1-X_{15}$ is a maximum of 6.

Other peptides for targeting collagen can be identified by modifying (e.g., mutating, truncating, lengthening) the peptides described above.

Linkers

In some embodiments, the TBM is covalently bound to the chelating ligand or metal chelate through a linker (L). The L can include, for example, a linear, branched or cyclic peptide sequence. In one embodiment, a L can include the linear dipeptide sequence G-G (glycine-glycine). In embodiments where the TBM includes a peptide, the L can cap the N-terminus of the TBM peptide, the C-terminus, or both N- and C-termini, as an amide moiety. Other exemplary capping moieties include sulfonamides, ureas, thioureas and carbamates. Ls can also include linear, branched, or cyclic alkanes, alkenes, or alkynes, and phosphodiester moieties. The L may be substituted with one or more functional groups, including ketone, ester, amide, ether, carbonate, sulfonamide, or carbamate functionalities. Specific Ls contemplated include NH—CO—NH—; —CO—$(CH_2)_n$—NH—, where n=1 to 10; dpr; dab; —NH-Ph-; —NH—$(CH_2)_n$—, where n=1 to 10; —CO—NH—; —$(CH_2)_n$—NH—, where n=1 to 10; —CO—$(CH_2)_n$—NH—, where n=1 to 10;

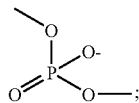

and —CS—NH—. Additional examples of Ls and synthetic methodologies for incorporating them into chelating ligands, particularly chelating ligands comprising peptides, are set forth in WO 01/09188, WO 01/08712, and U.S. patent application Ser. No. 10/209,183, entitled "Peptide-Based Multimeric Targeted Contrast Agents," filed Jul. 30, 2002.

Use of Chelating Ligands and Metal Chelates

Chelating ligands can be used to prepare metal chelates, as described above, for diagnostic purposes. For example, metal chelates prepared with Gd(III) can be useful as contrast agents in MR imaging. Contrast agents incorporating a TBM can bind a target and therefore can be particularly useful in targeted MR applications, e.g., to image blood flow, clots, lesions, or the myocardium. Particular examples of contrast agents that include one or more TBMs that bind to fibrin and that also include one or more of the chelating ligands or metal chelates described herein are Compounds 26, 28, and 30 set forth in the Examples below.

Preferably at least 10% (e.g., at least 50%, 80%, 90%, 92%, 94%, or 96%) of the contrast agent can be bound to the desired target at physiologically relevant concentrations of contrast agent and target. The extent of binding of a contrast agent to a target can be assessed by a variety of equilibrium binding methods, e.g., ultrafiltration methods; equilibrium dialysis; affinity chromatography; or competitive binding inhibition or displacement of probe compounds.

Contrast agents of the invention can exhibit high relaxivity as a result of target binding, which can lead to better MR image resolution. The increase in relaxivity upon binding is typically 1.5-fold or more (e.g., at least a 2, 3, 4, 5, 6, 7, 8, 9, or 10 fold increase in relaxivity). Targeted contrast agents having 7-8 fold, 9-10 fold, or even greater than 10 fold increases in relaxivity are particularly useful. The preferred relaxivity of an MRI contrast agent at 20 MHz and 37° C. is at least 10 mM-1s-1 per paramagnetic metal ion (e.g., at least 15, 20, 25, 30, 35, 40, or 60 mM-1s-1 per paramagnetic metal ion).

Metal chelates of lanthanides can also be useful as luminescent probes. Luminescent metal chelate probes can be useful in a variety of assays, e.g., to detect, separate, and/or quantify chemical and biological analytes in research and diagnostic applications, including high-throughput, real-time, and multiplex applications. For example, probes incorporating a TBM can bind to a target analyte of interest, and can have long luminescent lifetimes (e.g., greater than 0.1 µs, or 100 µs, or 1 ms), thereby improving sensitivity and applicability of various assay formats. See, generally, U.S. Pat. Nos. 6,406,297 and 6,515,113, for a description of assays suitable for inclusion of luminescent metal chelate probes. Luminescent metal chelate probes are particularly useful in immunoassays and real-time PCR detection assays.

Use of MRI Contrast Agents of the Invention

MRI contrast agents may be used in the same manner as conventional MRI contrast agents. Typically, the contrast agent is administered to a patient (e.g., an animal, such as a human) and an MR image of the patient is acquired. In embodiments having a TBM, a contrast-enhancing imaging sequence that preferentially increases a contrast ratio of a magnetic resonance signal of the target having a contrast agent bound thereto relative to the magnetic resonance signal of background blood or tissue can be used. These techniques include, but are not limited to, black blood angiography sequences that seek to make blood dark, such as fast spin echo sequences; flow-spoiled gradient echo sequences; and out-of-volume suppression techniques to suppress in-flowing blood. These methods also include flow independent techniques that enhance the difference in contrast due to the T1 difference between contrast-enhanced target and blood and tissue, such as inversion-recovery prepared or saturation-recovery prepared sequences that will increase the contrast between the target and background tissues. Methods of preparation for T2 techniques may also prove useful. Finally, preparations for magnetization transfer techniques may also improve contrast with contrast agents of the invention.

Methods may be used that involve the acquisition and/or comparison of contrast-enhanced and non-contrast images and/or the use of one or more additional contrast agents. The additional contrast agents can exhibit affinity for a target. Methods as set forth in U.S. patent application Ser. No. 09/778,585, entitled MAGNETIC RESONANCE ANGIOGRAPHY DATA, filed Feb. 7, 2001 and U.S. patent application Ser. No. 10/209,416, entitled SYSTEMS AND METHODS FOR TARGETED MAGNETIC RESONANCE IMAGING OF THE VASCULAR SYSTEM, filed Jul. 30, 2002 may also be used.

Contrast agents of the invention can be formulated as a pharmaceutical compositions in accordance with routine procedures. As used herein, the contrast agents of the invention can include pharmaceutically acceptable derivatives thereof. "Pharmaceutically acceptable" means that the agent can be administered to an animal without unacceptable adverse effects. A "pharmaceutically acceptable derivative" means any pharmaceutically acceptable salt, ester, salt of an ester, or other derivative of a contrast agent or compositions of this invention that, upon administration to a recipient, is capable of providing (directly or indirectly) a contrast agent of this invention or an active metabolite or residue thereof. Other derivatives are those that increase the bioavailability when administered to a mammal (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the contrast agents of this invention include counter ions derived from pharmaceutically acceptable inorganic and organic acids and bases known in the art.

Pharmaceutical compositions of the invention can be administered by any route, including both oral and parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, contrast agents of the invention can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions of this invention comprise the contrast agents of the present invention and pharmaceutically acceptable salts thereof, with any pharmaceutically acceptable ingredient, excipient, carrier, adjuvant or vehicle.

A contrast agent is preferably administered to the patient in the form of an injectable composition. The method of administering a contrast agent is preferably parenterally, meaning intravenously, intra-arterially, intrathecally, interstitially or intracavitarily. Pharmaceutical compositions of this invention can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass. The optimal dose will be determined empirically following the disclosure herein.

The invention will be further described in the following examples, which do not limit the scope of the invention described in the claims.

EXAMPLES

Example 1

Synthesis of 2-(R)-2-(4,7,10-Tris-t-butylcarboxymethyl-1,4,7,10-tetraazacyclododec-1-yl)-pentanedioic acid, 1-t-butyl ester (EP2104-11)

An overall synthetic scheme, with yields, for preparing the above compound is set forth below.

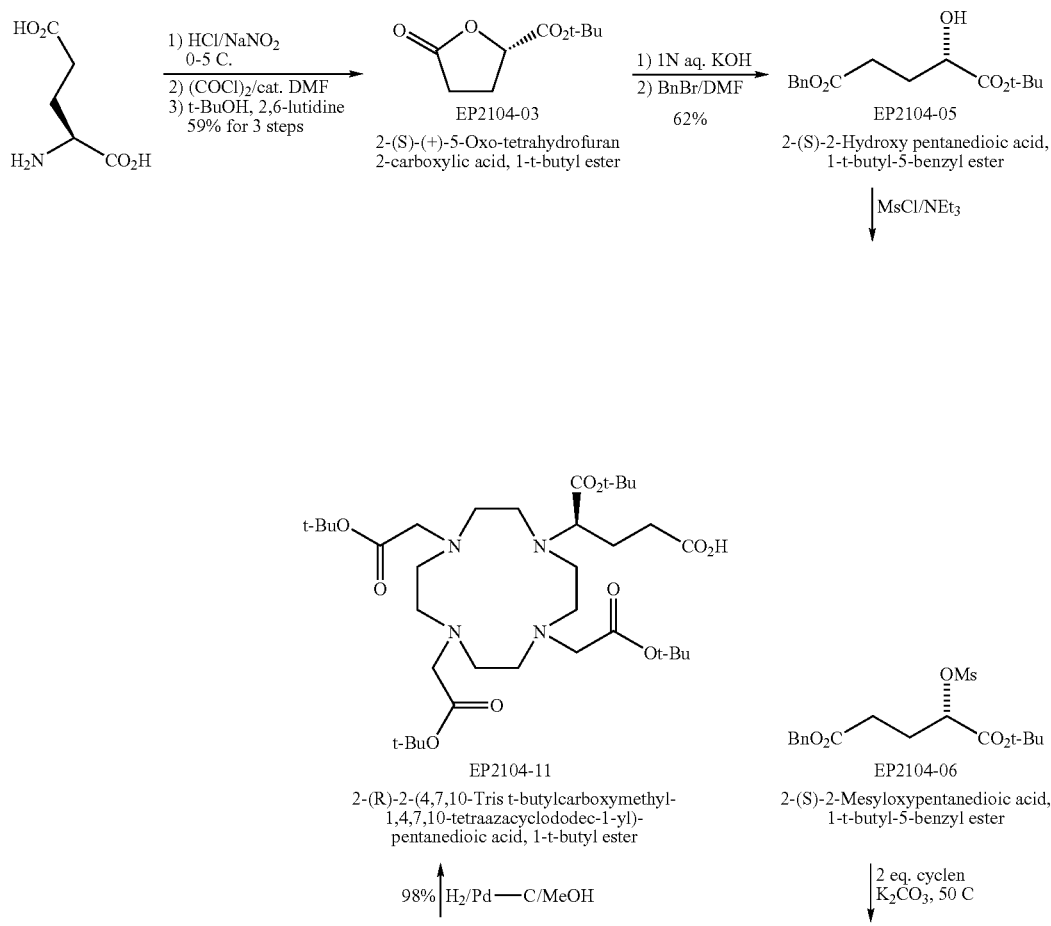

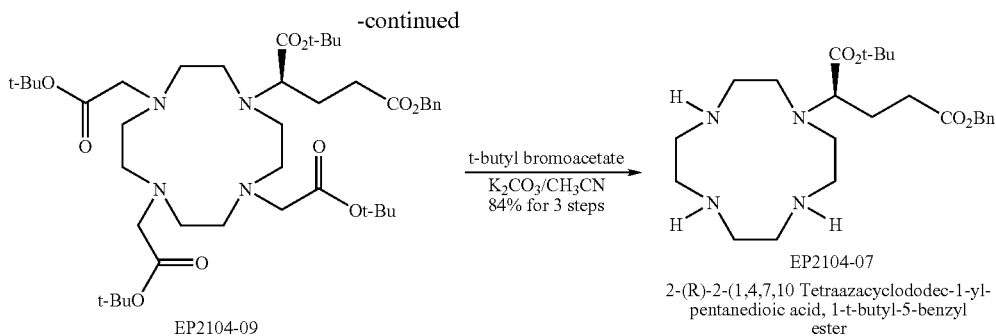

EP2104-09 t-butyl bromoacetate
K₂CO₃/CH₃CN
84% for 3 steps

EP2104-07
2-(R)-2-(1,4,7,10 Tetraazacyclododec-1-yl-pentanedioic acid, 1-t-butyl-5-benzyl ester

A. Preparation of (S)-(+)-5-Oxo tetrahydrofuran-2-carboxylic acid, t-butyl ester (EP2104-03)

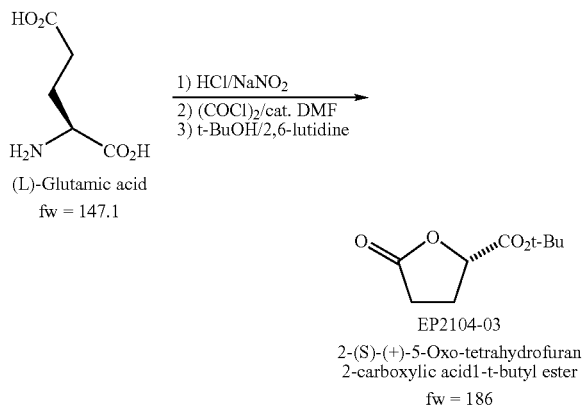

(L)-Glutamic acid
fw = 147.1

1) HCl/NaNO₂
2) (COCl)₂/cat. DMF
3) t-BuOH/2,6-lutidine

EP2104-03
2-(S)-(+)-5-Oxo-tetrahydrofuran 2-carboxylic acid 1-t-butyl ester
fw = 186

A solution of sodium nitrite (140 g, 2.03 mol) in water (320 mL) was added over 4 h to a mixture of L-glutamic acid (200 g, 1.36 mol), dioxane (150 mL) and HCl (280 mL) in water (530 mL) and maintained at an internal temperature of 0-5° C. Some evolution of nitric oxide (brown gas) was observed. HPLC monitoring indicated that the reaction was complete once the addition of a stoichiometric amount of aqueous sodium nitrite was added (e.g., after approx. 30 min. for a reagent addition step requiring 45 minutes to complete). Further investigation using an in situ ReactIR probe indicated that the reaction required 2 h reaction time after the addition of the aqueous sodium nitrite solution.

On completion of the addition, the mixture was warmed to r.t. and stirred 2 h, then solvents were removed in vacuo at 50-55° C. The residue was coevaporated with toluene (2×500 mL) to remove additional water, then ethyl acetate (1 L) was added, followed by sodium sulfate (100 g), and the mixture was stirred 0.5 h. The ethyl acetate solution was decanted and filtered, and the solids were washed and stirred with additional ethyl acetate (1 L). The combined filtrates were concentrated in vacuo, and the resulting residue was further dried under high vacuum (1 torr). The mass of crude residue containing EP2104-01 was 184 g, exceeding the mass of the theoretical yield by 7 g, attributable to solvent trapped by the viscous, syrupy residue. A sample of this residue was subjected to chiral GC analysis, which indicated the optical purity of this material to be 93.5% e.e.

Oxalyl chloride (297 mL, 432 g, 3.40 mol) was added to a solution of crude EP2104-01 (assumed ~177 g, 1.36 mol) and DMF (2.00 mL) in dry dichloromethane (800 mL) and cooled to 0-5° C. in an ice bath. The mixture was warmed to r.t. after the addition was complete and stirred 2 h, then concentrated in vacuo. The residue was co-evaporated with dichloromethane (1 L), and the residue was transferred under inert atmosphere to a 500 mL distillation flask and subjected to vacuum distillation (short path still head/condenser). The acid chloride distilled at 86-96° C. at 1 torr. The mass of distillate obtained was 184 g, which was determined to be ≧90% pure by proton NMR (≧82% yield).

The acid chloride (184 g, 0.989 mol) in dichloromethane (300 mL) was added over a period of 1.5 h to a stirred solution of t-butanol (189 mL, 148 g, 1.98 mol) and 2,6-lutidine (138 mL, 127 g, 1.19 mol) in dichloromethane (600 mL) cooled to 0° C. On completion of the addition the mixture was warmed to r.t. and stirred overnight. The mixture was then poured into an addition funnel and washed with water (2×800 mL), 10% aq. citric acid (2×800 mL), saturated sodium bicarbonate (2×800 mL) and brine (2×800 mL), then dried, decanted and concentrated to a dark brown residue, which crystallized on standing. The crude residue was dissolved in EtOAc (150 mL), and applied to a plug composed of a wetted bed of Celite (bottom layer, 150 g), flash silica (middle layer, 150 g) and activated carbon (top layer, Darco, −100 mesh, 150 g). The loaded plug was eluted with EtOAc (3 L), and the filtrate was concentrated to a residue, which was crystallized by adding EtOAc (200 mL) followed by hexanes (600 mL), to give 124 g of EP2104-03 (49%). A second crop of crystals (29 g, 12%) was obtained by concentrating to a residue and precipitating with hexanes (300 mL), giving a yield of 61% EP2104-03. This material was determined to have e.e. ≧99% by chiral GC. ¹H NMR (CDCl₃): δ=4.8 (dd, 1H), 2.8-2.2 (m, 4H), 1.5 (s, 1H) ppm.

B. Preparation of 2-(S)-2-Hydroxy pentanedioic acid, 1-t-butyl-5-benzyl ester (EP2104-05)

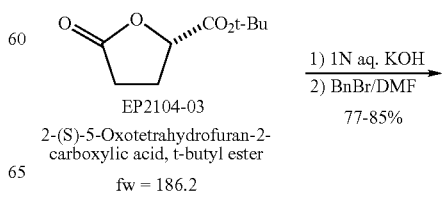

EP2104-03
2-(S)-5-Oxotetrahydrofuran-2-carboxylic acid, t-butyl ester
fw = 186.2

1) 1N aq. KOH
2) BnBr/DMF
77-85%

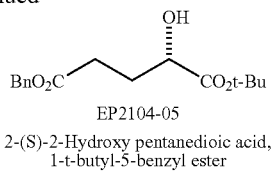

EP2104-05
2-(S)-2-Hydroxy pentanedioic acid,
1-t-butyl-5-benzyl ester fw = 294.3

A solution of 1 N KOH (357 mL, 0.357 mol) was added in a single portion to a stirred solution of EP2104-03 (66.4 g, 0.357 mol) in THF (250 mL). The internal temperature rose to 37° C. The mixture was heated and stirred at 40° C. for 2 h (as determined by IR), then concentrated to a solid in vacuo, and dried on high vacuum overnight. Endpointing by IR monitoring was performed using real-time monitoring with a probe (ReactIR). It was determined by this method that the reaction reached completion after 1 h at 40° C.

The solid residue was suspended and stirred in DMF (650 mL), and benzyl bromide (44.6 mL, 64.2 g, 0.375 mol) was added. After stirring overnight, the mixture was poured into ice water (1.5 L), then extracted with ethyl acetate (2×500 mL), dried (Na$_2$SO$_4$) and concentrated in vacuo. It was subsequently determined (by HPLC) that this reaction (EP2104-04 to EP2104-05) was complete within 8 h. The weight of the crude residue after removing ethyl acetate was 150 g, indicating the presence of approximately 45 g of DMF left to be removed. The remainder of DMF was removed in vacuo using rotary evaporation with a high vacuum pump, leaving 101 g of crude EP2104-05. This material was applied to a plug of flash silica (8×25 cm) and eluted with hexanes (1 L), 25% EtOAc/hexanes (1 L) and 50% EtOAc/hexanes (2 L). Fractions containing the product were pooled and concentrated to give 79.7 g (76%) of EP2104-05 as a light yellow tinted oil. Proton NMR (CDCl$_3$): δ=7.35 (m, 5H), 5.13 (s, 2H), 4.1 (m, 1H), 2.88 (d, 1H), 2.59-2.46 (m, 2H), 2.2-2.1 (two m, 2H), 1.48 (s, 9H) ppm.

C. Preparation of (2)-(R)-2-(1,4,7,10 Tetraazacyclododec-1-yl-pentanedioic acid, 1-t-butyl-5-benzyl ester (EP2104-07)

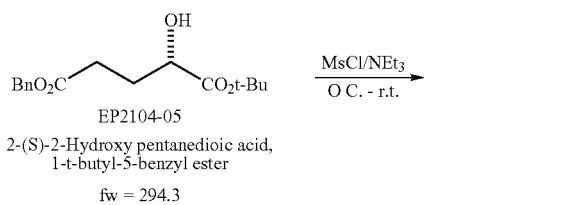

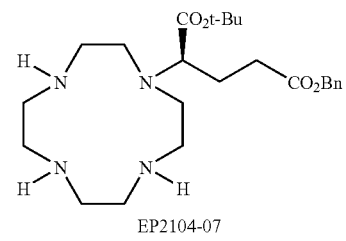

EP2104-07
2-(R)-2-(1,4,7,10 Tetraazacyclododec-1-yl-pentanedioic acid, 1-t-butyl-5-benzyl ester fw = 448.6

Methanesulfonyl chloride (25.6 mL, 37.7 g, 0.329 mol) was added to a stirred mixture of EP2104-05 (87.8 g, 0.299 mol) and NEt$_3$ (46.0 mL, 33.3 g, 0.329 mol) in CH$_2$Cl$_2$ (500 mL) and cooled to 0-5° C. in an ice bath. After the addition was complete, the mixture was warmed to r.t., stirred 0.5 h, and checked by HPLC for completeness. Water (300 mL) was added, the organic phase was separated and washed with brine (300 mL) then dried (Na$_2$SO$_4$), decanted and concentrated in vacuo to give 110.4 g (91%) of EP2104-06, sufficiently pure to be used in the next step. Proton NMR (CDCl$_3$): δ=7.35 (m, 5H), 5.13 (s, 2H), 4.97 (dd, 1H), 3.11 (s, 3H), 2.57-2.14 (m, 4H), 1.48 (s, 9H) ppm.

The mesylate EP2104-06 (102 g, 0.270 mol) as a solution in CH$_3$CN (500 mL) was added to a stirred mixture of cyclen (95.6 g, 0.555 mol) and potassium carbonate (38.3 g, 0.270 mol) in CH$_3$CN (1.50 L, preheated to 50° C.) over a period of 45 min, and the reaction was monitored by HPLC for completeness. After 19 h, the reaction mixture was cooled to rt. After cooling, the reaction mixture was filtered to remove potassium salts and cyclen mesylate, and the filter cake was washed with additional CH$_3$CN (2×100 mL). The filtrate was concentrated to a red oil in vacuo, and then re-dissolved in EtOAc (3.00 L). The organic solution was washed with water (300 mL) and brine (100 mL), separated and dried (Na$_2$SO$_4$), then decanted and concentrated in vacuo to give 114 g of crude product (92% pure by HPLC area integration). After these washes, no residual cyclen (M/z=173, MH$^+$) was detected by LC/MS. In certain embodiments, if cyclen were detected at this point, the organic phase would be subjected to the washes until the LC/MS indicated that cyclen was no longer present.

Note that this reaction sequence has been performed in one pot (using CH$_3$CN for both the mesylate formation and the alkylation reaction, with no stripping of solvent in between) on a 10 g scale. The CH$_3$CN solution of EP2104-06 was added to a mixture of cyclen and potassium carbonate in CH$_3$CN preheated to 50° C. over a period of 10 minutes. No difference in the HPLC reaction and impurity profile were observed when running the one-pot reaction sequence, as opposed to the stepwise sequence.

D. Preparation of 2-(R)-2-(4,7,10-Tris t-butylcarboxymethyl-1,4,7,10-tetraazacyclododec-1-yl)-pentanedioic acid-1-t-butyl-5-benzyl ester (EP2104-09)

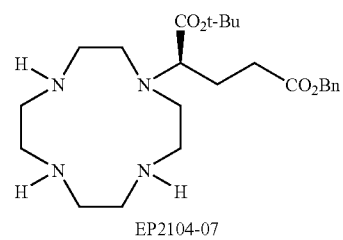

EP2104-07
2-(R)-2-(1,4,7,10 Tetraazacyclododec-1-yl-pentanedioic acid, 1-t-butyl-5-benzyl ester
fw = 448.6 t-butyl bromoacetate
K₂CO₃/CH₃CN
42% for three steps from EP2104-05

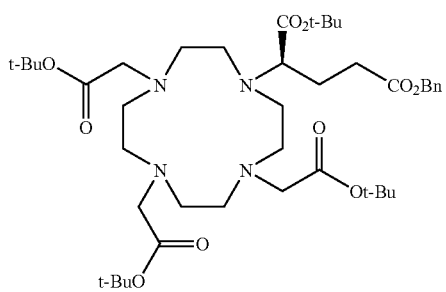

EP2104-09
2-(R)-2-(4,7,10-Tris t-butylcarboxymethyl-1,4,7,10-tetraazacyclododec-1-yl)-pentanedioic acid 1-t-butyl-5-benzyl ester
fw = 791.0

Crude EP2104-07 (90.0 g, 0.180 mol) and potassium carbonate (203 g, 1.47 mol) were dissolved/suspended in dry CH₃CN (1.00 L), then a solution of t-butyl bromoacetate (80.0 mL, 0.540 mol) in CH₃CN (200 mL) was added over a period of 1 h. HPLC monitoring indicated that the reaction was incomplete. An additional portion of t-butylbromoacetate (10 mL, 13.21 g, 67.7 mmol) was then added. The mixture was filtered, and the filtrate was concentrated in vacuo and dissolved in EtOAc (1.40 L), washed with water (1 L), saturated sodium bicarbonate (1 L) and brine (1 L). After drying (Na₂SO₄), the solution was decanted and concentrated to a volume of 350-500 mL in vacuo, at which point a fine white precipitate formed. The precipitate was isolated by vacuum filtration, and the filter cake was washed with ethyl acetate (3×150 mL), then further dried under high vacuum (<5 torr) to remove traces of ethyl acetate to give 119 g (84.0% for three steps, formation of EP2104-06, EP2104-07 and EP2104-09) of fully alkylated cyclen EP2104-09. ¹H NMR (CDCl₃): δ=7.34 (m, 5H), 5.08 (d, 2H), 3.39-2.00 (m, 27H), 1.43 (four s, 36H) ppm.

E. Preparation of 2-(R)-2-(4,7,10-Tris-t-butylcarboxymethyl-1-4-7-10-tetraazacyclododec-1-yl)-pentanedioic acid, 1-t-butyl ester (EP2104-11)

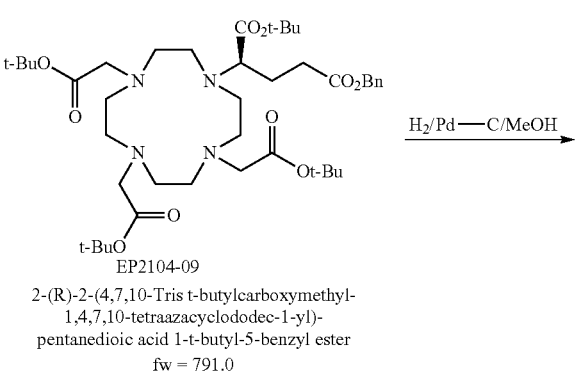

EP2104-09
2-(R)-2-(4,7,10-Tris t-butylcarboxymethyl-1,4,7,10-tetraazacyclododec-1-yl)-pentanedioic acid 1-t-butyl-5-benzyl ester
fw = 791.0

H₂/Pd—C/MeOH

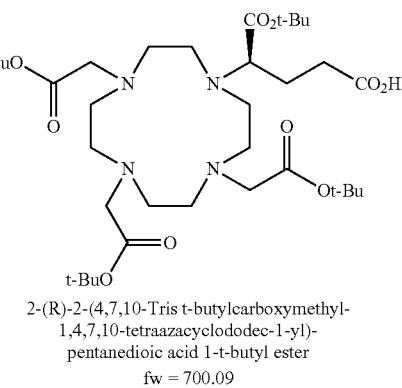

2-(R)-2-(4,7,10-Tris t-butylcarboxymethyl-1,4,7,10-tetraazacyclododec-1-yl)-pentanedioic acid 1-t-butyl ester
fw = 700.09

Palladium on carbon (dry, 2.3 g, ≈10% by mass) was added as a slurry in water (20 mL) to a MeOH solution of EP2104-09 (18.0 g, 22.7 mmol, in 100 mL MeOH) in a Parr pressure shaker bottle. In certain embodiments, Pd—C containing 50% water (10% Pd—C, wet, Degussa type) can be used. The mixture was subjected to two cycles of vacuum and hydrogen purge, then pressurized to 50 psi hydrogen and shaken for 18 h. HPLC indicated that the only major species present was the desired product. It was found in subsequent experiments that this reaction reached completion within an hour at a hydrogen pressure of 20 psi. After evacuating the system to remove hydrogen, the bottle was opened and Celite (5.00 g) was added. The slurry was filtered through a MeOH-wet bed of Celite (5 g), and the filtrate was concentrated to a light yellow syrup in vacuo. The syrup was coevaporated with acetonitrile (2×150 mL) in order to azeotrope out residual water and to remove any remaining methanol (this can be confirmed by proton NMR), giving 15.6 g (98%) of an amorphous off-white solid after drying under high vacuum. In some embodiments, isolation of EP2104-11 by precipitation, rather than by evaporation to a solid residue, may be more amenable to scale up and production. HPLC: 95% pure by area integration. Proton NMR (CDCl$_3$): δ=3.61-2.0 (6 m, 26H), 1.45 (3 lines, 36 H) ppm.

Example 2

Preparation of Activated Ester, 2-(R)-2-(4,7,10-Tris-t-butylcarboxymethyl-1-4-7-10-tetraazacyclododec-1-yl)-pentanedioic acid, 1-t-butyl ester-5-pentafluorophenyl ester (EP2104-12)

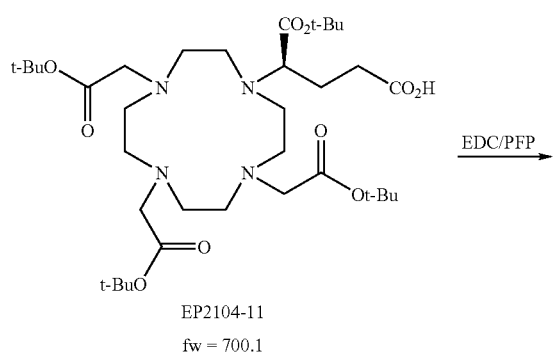

EP2104-11
fw = 700.1

↓ EDC/PFP

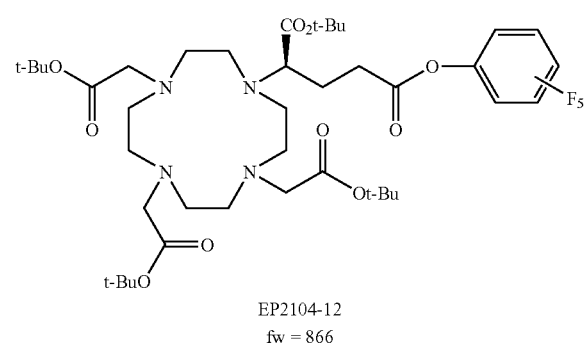

EP2104-12
fw = 866

EP2104-11 (1.50 g, 2.14 mmol), pentafluorophenol (473 mg, 2.57 mmol) and polystyrene carbodiimide (1.28 mmol/g, 2.51 g, 3.21 mmol) were combined in CH$_2$Cl$_2$ (150 mL) in a fritted shaker bottle. The mixture was shaken and sampled at 15-30 min intervals to determine the endpoint of the reaction. HPLC indicated the reaction reached completion within 2 h. The mixture was filtered through the reactor frit, and the resin and the reactor were washed with additional CH$_2$Cl$_2$ (150 mL). The combined filtrates were concentrated in vacuo and dried under high vacuum. The weight of the crude residue (glassy foam) was 1.75 g, determined to be 63% pure (59% yield) by HPLC. The only detectable impurity in this crude active ester was pentafluorophenol, and the material has been routinely carried through to the next synthetic step without purification after HPLC assay.

Alternative Preparation of EP-2104-12

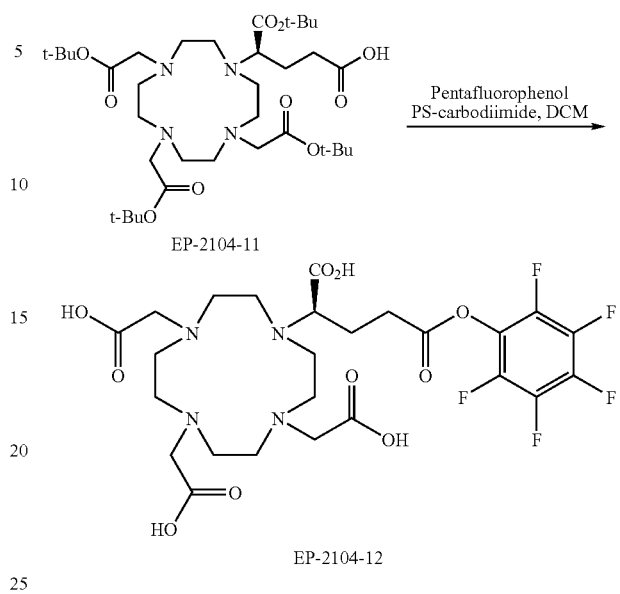

A Nalgen bottle was charged with EP-2104-11 (43.3 g) and methylene chloride (600 mL). To this mixture was added PS-carbodiimide (58.0 g, 1.2 equivalents; 1.28 mmole/g loading capacity; Supplier: Argonaut) over a period of 3-5 minutes while maintaining an internal temperature of 22-25° C. The bottle was placed onto an orbital shaker for 6.0 hours. Excess pentafluorophenol remaining in the unpurified EP-2104-12 did not impede the next reaction.

The reaction mixture was vacuum filtered through a glass-fritted funnel and the resin was washed with methylene chloride (150 mL). The filtrate was subjected to distillation conditions on a Rotovap (15-20 mm Hg, 35-40 C water bath) until all the solvent was removed. The glassy solids were dried under vacuum (15-20 mm Hg) until a constant weight to provide EP-2104-12 (43.18 g).

Example 3

Derivatization of EP2104-11 for Determination of Optical Purity

A. Preparation of 2-(R)-2-(4,7,10-Tris-t-butylcarboxymethyl-1-4-7-10-tetraazacyclododec-1-yl)-pentanedioic acid, 1-t-butyl ester, (R)-(+)-α-methylbenzylamide (EP2104-13)

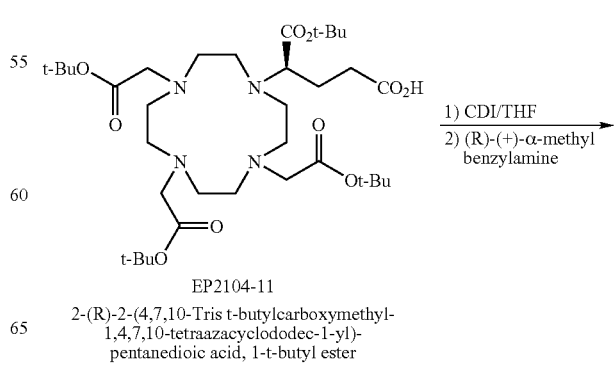

EP2104-11
2-(R)-2-(4,7,10-Tris t-butylcarboxymethyl-1,4,7,10-tetraazacyclododec-1-yl)-pentanedioic acid, 1-t-butyl ester

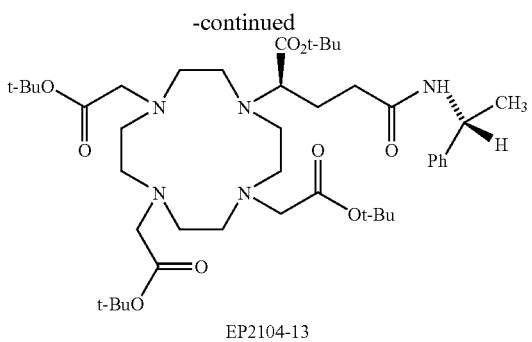

EP2104-13

2-(R)-2-(4,7,10-Tris t-butylcarboxymethyl-
1,4,7,10-tetraazacyclododec-1-yl)-
pentanedioic acid, 1-t-butyl ester,
5-(R)-(+)α-methylbenzylamide Carbonyl-1,1'-diimidazole (30.0 mg, 0.185 mol) was added to a stirred solution of EP2104-11 (100 mg, 0.143 mmol) in THF (2 mL), and the mixture was stirred 2 h. (R)-(+)-α-methylbenzylamine (0.020 mL, 18.3 mg 0.150 mmol) was added, followed by N,N-diisopropylethylamine (0.0350 mL, 26.0 mg, 0.200 mmol), and the mixture was stirred 5 h. The mixture was then concentrated, and the residual oil was dissolved in ethyl acetate (3 mL) and washed with water (3 mL). The organic phase was separated, dried, decanted and concentrated, then the residue was dried under high vacuum. A sample of this residual oil was removed for proton NMR analysis. $^1$H NMR (CDCl$_3$): δ=8.00 (br d, 1H) ppm. A single doublet was observed. It had been previously shown that two such doublets were present in the proton NMR spectrum of the diastereomeric amides independently prepared racemic EP2104-11. δ=5.00 (q, 1H) ppm. A single set of signals was observed for the methine proton on the amine chiral center, also indicating that to the limits of detection (5%), a single diastereomeric amide was present.

B. Alternative Preparation of 2-(R)-2-(4,7,10-Tris-t-butylcarboxymethyl-1-4-7-10-tetraazacyclododec-1-yl)-pentanedioic acid, 1-t-butyl ester, (R)-(+)-α-methylbenzylamide (EP2104-13)

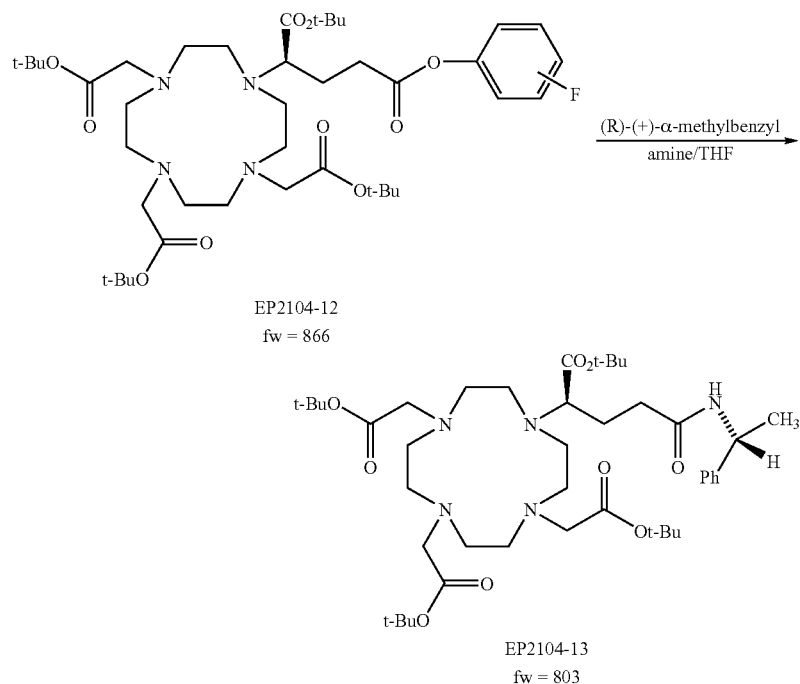

EP2104-12
fw = 866

EP2104-13
fw = 803

The conversion of EP2104-11 to EP2104-13 was also done via the activated pentafluorophenyl ester, EP2104-12. R-(+) alpha methylbenzylamine (18.0 uL, 17.0 mg, 0.140 mmol) was added to a stirred solution of EP2104-12 (110 mg, 0.130 mmol) in THF (3 mL). After 0.5 h, HPLC indicated that the reaction was complete, and the mixture was concentrated to a residue in vacuo. A proton NMR spectrum was taken of this material, and the data obtained was essentially identical to the NMR data obtained from EP2104-13 prepared via CDI coupling of EP2104-11 with alpha methylbenzylamine.

Example 4

Preparation of a Targeted Chelating Ligand—Conversion of Compound 24 to Compound 28

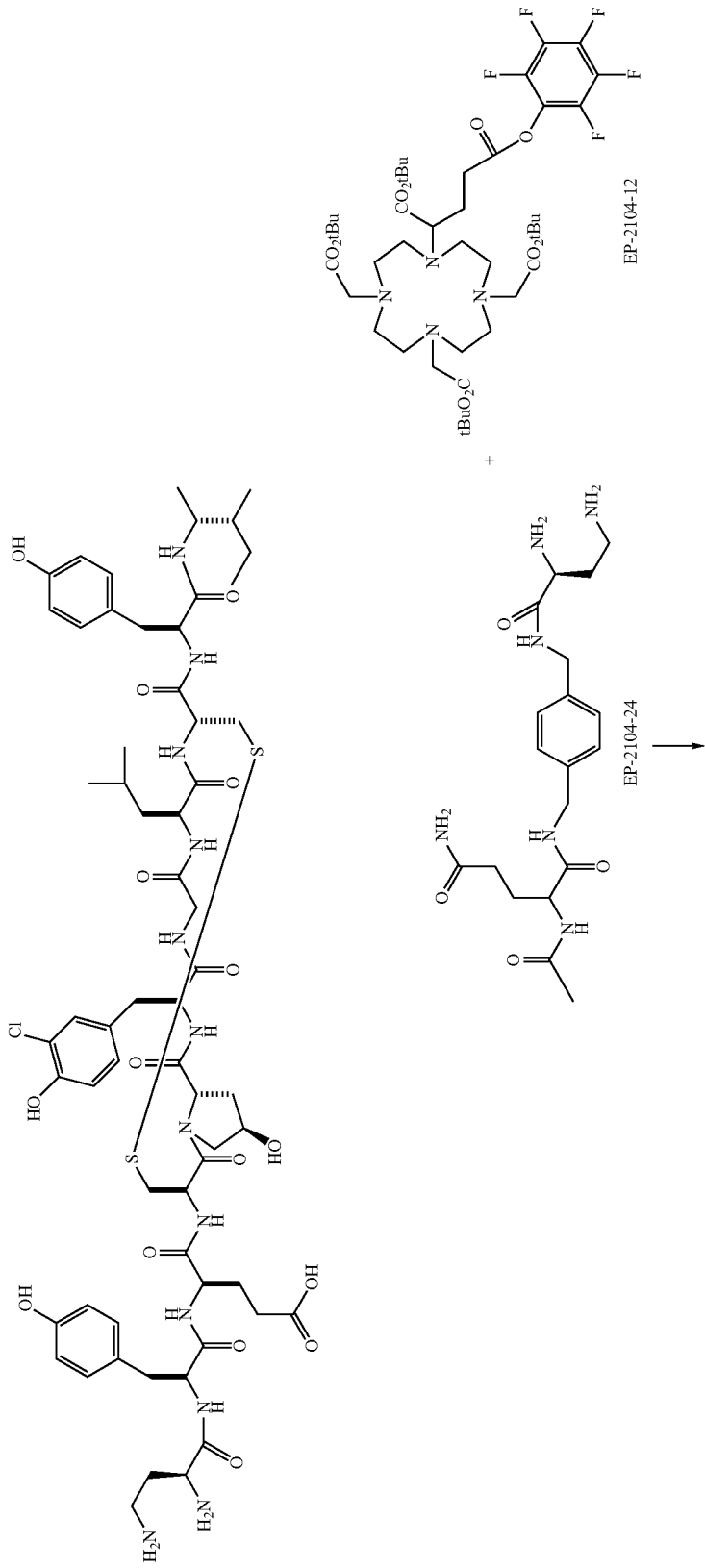

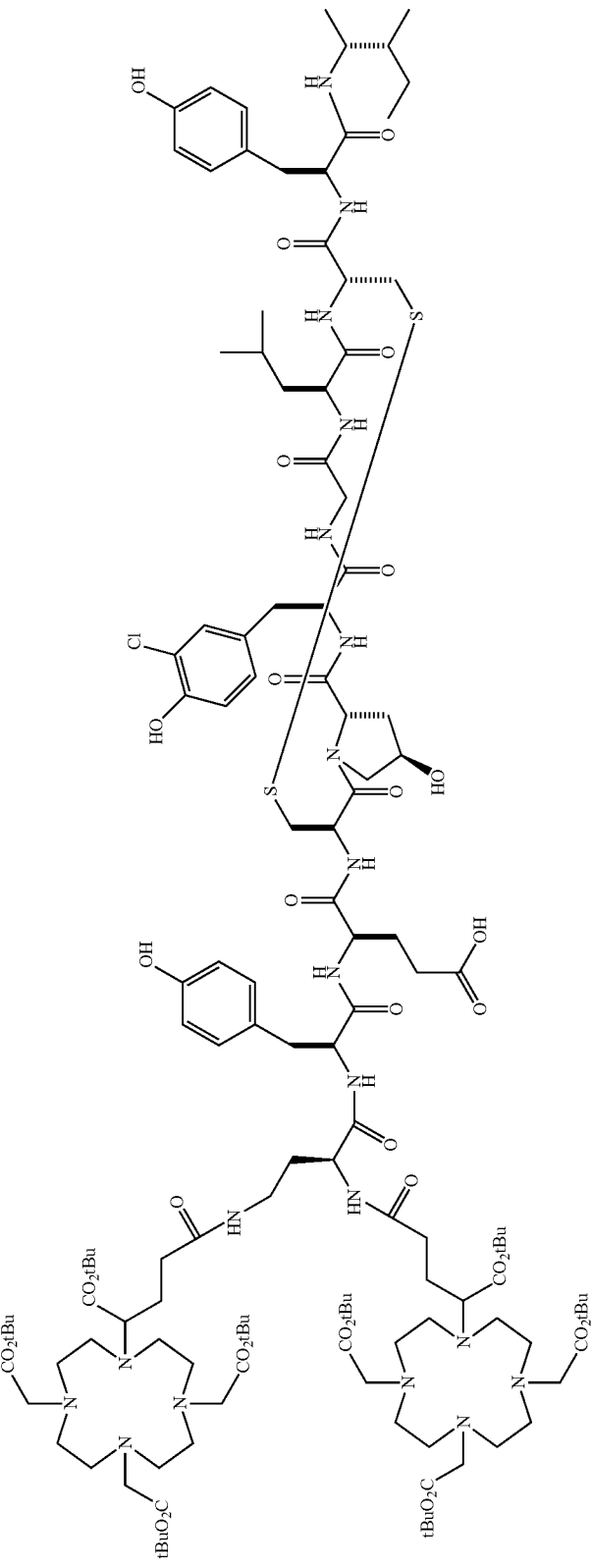

-continued
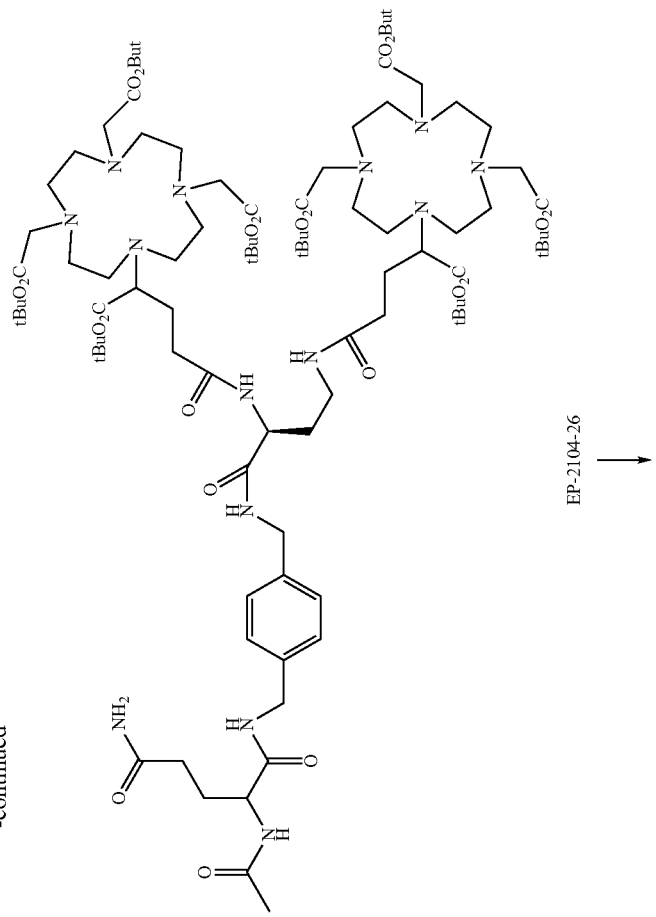
EP-2104-26

-continued
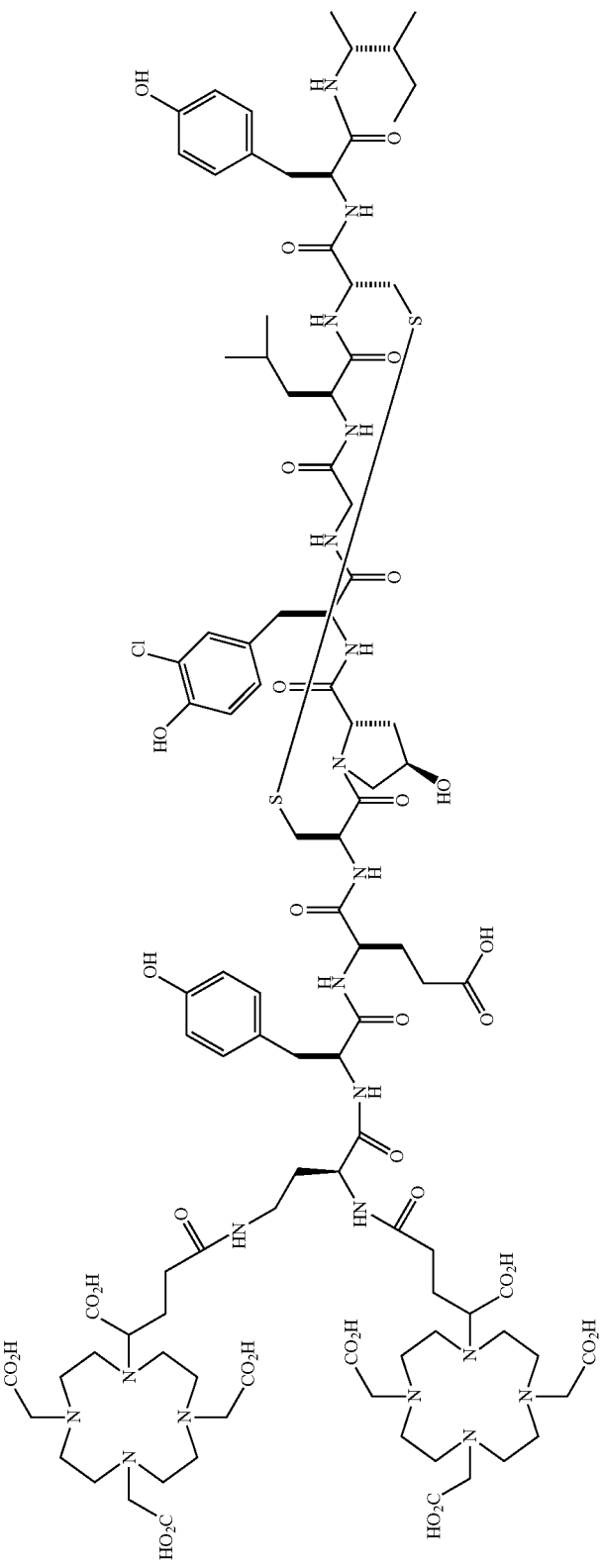

-continued
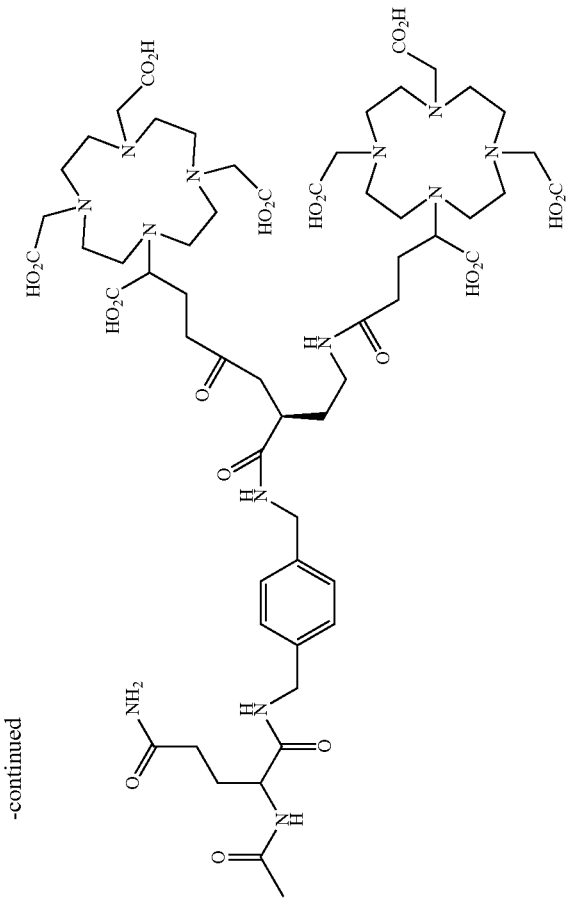
EP-2104-28 (Ligand)

A suitable reaction flask was charged with DMF (300 mL) and Compound 24 (16.9 g, 2.82 mmol based on 28.7% potency, 50.7% HPLC by area). Compound 24 utilized in this reaction was prepared from a two-step sequence starting with Compound 2080 peptide. In some embodiments, Compound 24 may be prepared on a solid support; see Examples below. In a separate flask, EP-2104-12 (25.6 g, ~65% potency, 19.1 mmole, 1.6 equivalents per amino group) was dissolved into DMF (100 mL) and added to the Compound 24/DMF mixture over a period of 3-5 minutes while maintaining an internal temperature of 22-25° C. Diisopropylethylamine (8.0 mL, 45.0 mmol) was added to the reaction mixture in 2.0 mL portions over 25-30 minutes while maintaining an internal temperature of 22-25° C. At this point the reaction mixture had a pH~6. A "dry" pH stick was treated with water and subjected to an aliquot of reaction mixture. The reaction mixture was allowed to stir at 22-25° C. for 11 hours. To the reaction mixture was added additional EP-2104-12 (2.5 g) and the reaction was allowed to stir for 4.0 hours while maintaining an internal temperature of 22-25° C. Saturated sodium chloride (1.5 L) was added over a period of 25-30 minutes while maintaining an internal temperature of 22-25° C. The slurry was allowed to stir for 30 minutes. The solids formed were collected by vacuum filtration and allowed to dry under vacuum (15-20 mm Hg, 22-25° C.) until a constant weight (~3 days) to provide Compound 26 as an off-white solid (45.0 g of a wet cake; 37.0% HPLC by area; 15.5% potency; 4.0% water by Karl-Fischer. Actual Compound 26: 6.96 g, 2.46 mmole, 87% yield). The course of the reaction was monitored by LC/MS, and the results are given in Table 1 below.

TABLE 1

| Reaction Time | Monomer | Dimer | Trimer | Compound 26 | Pentamer |
|---|---|---|---|---|---|
| 0.75 hours | 15% | 65% | 20% | — | — |
| 2.0 hours | — | — | 50% | 50% | — |
| 11 hours | — | — | 30% | 70% | — |
| 24 hours | — | — | 5% | 90% | 5% |

A mixture consisting of trifluoromethanesulfonic acid:methanesulfonic acid:1-Dodecanethiol:Water (88:4:4:4, 805.0 mL) was added to Compound 26 (45.0 g) in 3 equal portions over a period of 10.0 minutes while maintaining an internal temperature of 22-25° C. The deprotection cocktail was added slowly in order to dissolve all the solids uniformly. The reaction mixture was allowed to stir for 45 minutes. A separate flask was charged with isopropyl ether (1.0 L) and cooled to 0-5° C. The reaction mixture was filtered into the flask containing the isopropyl ether over a period of 40.0 minutes while maintaining an internal temperature of 0-5° C. The slurry was allowed to warm to 22-25° C. over a period of 30.0 minutes. The solids were collected by vacuum filtration, washed with isopropyl ether and dried under vacuum (15-20 mm Hg, 22-25° C.) until a constant weight to provide Compound 28 as an off-white solid (52.0 g, 36.1% HPLC by area, 10.8% potency, 0.54 mmol/g chelatable: 5.6 g, 1.58 mmole, 56% from Compound 24).

Example 5

Conversion of Compound 28 Chelating Ligand to Compound 30 Gd(III) Metal Chelate

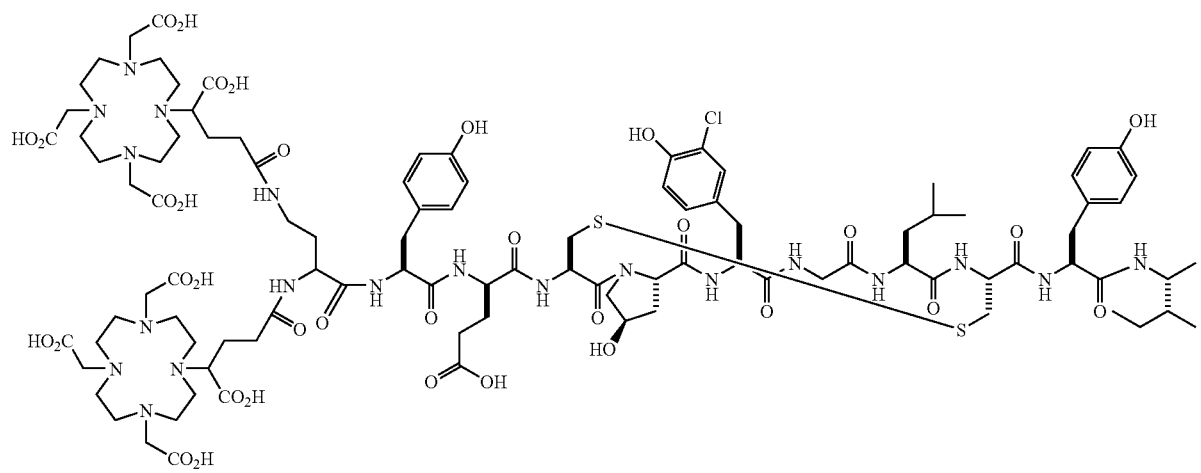

-continued
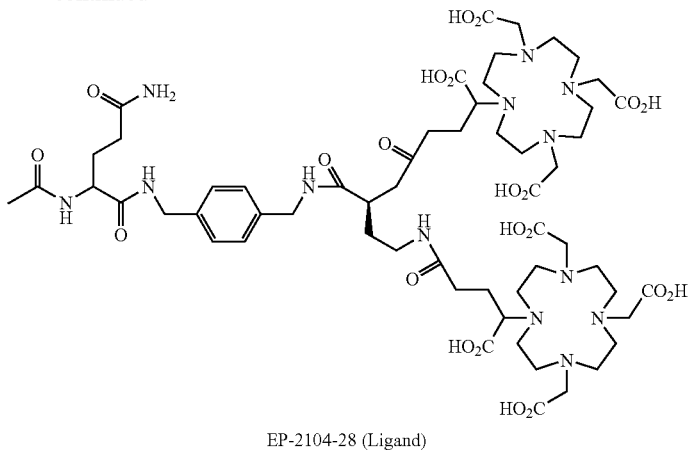
EP-2104-28 (Ligand)
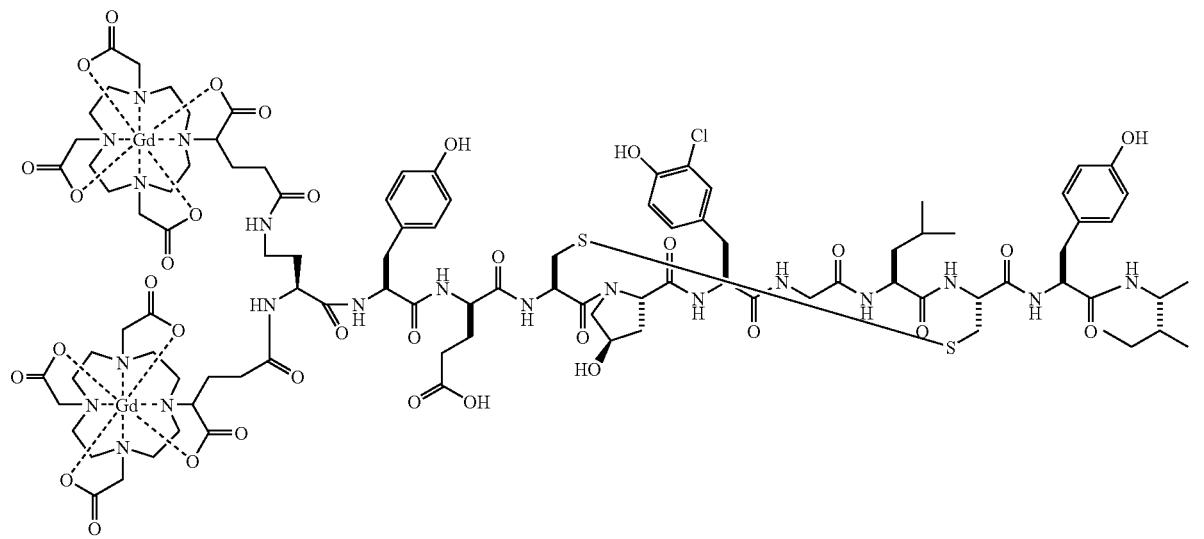
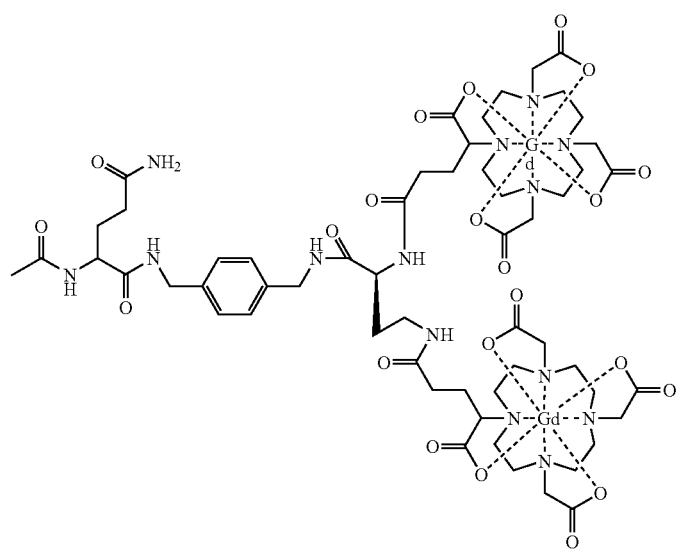
EP-2105-30

A suitable reaction flask was charged with Compound 28 (52.0 g) and water (400.0 mL). The mixture was allowed to stir at 22-25° C. and 1N aqueous sodium hydroxide (600.0 mL) was added until a pH of ~7 was achieved while maintaining an internal temperature of 22-25° C. The concentration of chelatable equivalents (ligand available for chelation) was determined by photometric titration as follows:

Into a 1.5 mL quartz cuvette was placed 10 µL of Compound 28 reaction solution and 1.0 mL of Arsenazo (III) solution (10 µM Arsenazo III in 0.15 M NH4OAc buffer pH 7). The cuvette was placed into an UV/Vis spectrophotometer and zeroed at 656 nm. Six (6) aliquots of an Pb(NO3)2 solution (4.85 mM solution available from Aldrich), 10 µL each (a total of 60 µL), was titrated into the cuvette. A positive absorbance was observed (0.0946), which represents the end point of the titration. To this mixture was added $GdCl_3$ (12.14 g, 32.4 mmoles) over a period of 5.0 minutes while maintaining an internal temperature of 22-25° C. Additional 1N aqueous sodium hydroxide (~145.5 mL) was added over the course of the $GdCl_3$ addition in order to maintain reaction pH~7. The reaction mixture was allowed to stir for 1.0 hour at 22-25° C. EDTA was added in order to complex remaining free gadolinium in the reaction mixture. The reaction mixture was monitored by LC/MS. Ethylenediamine-tetraacetic acid (EDTA) (24.0 mL of a 0.1 M solution, 2.4 mmoles) was added and the reaction mixture was allowed to stir for 1.5 hours at 22-25° C. The reaction mixture was transferred to a graduate cylinder and shown to have a volume of 1.25 L (pH~7). The concentration of the ligand was calculated according to the following equation:

4.85 mM $Pb(NO_3)_2 \times 6.0$ equivalents of Pb (or 60 µL) to titrate solution=29.1 mM ligand solution. The total volume of the pH~7 ligand solution used for the calculation was 1.02 L. The concentration calculated from Equation 1 was multiplied by the total volume of reaction solution to give the amount of chelatable ligand:

29.1 mM×1.02 L=29.7 mmoles of chelatable ligand.

The total amount of gadolinium required (mmoles) was determined from the concentration of chelatable equivalents multiplied by the total volume of the ligand solution:

29.7 mmoles×371.7 g/mole of $GdCl_3.6H_2O \times$ 110%=12.14 g of $GdCl_3.6H_2O$.

The purification was carried out using Reverse Phase Chromatography (C-18). Typical yields range from 50-70%.

Example 6

Preparation of Compound 24 on a Peptide Synthesis Resin

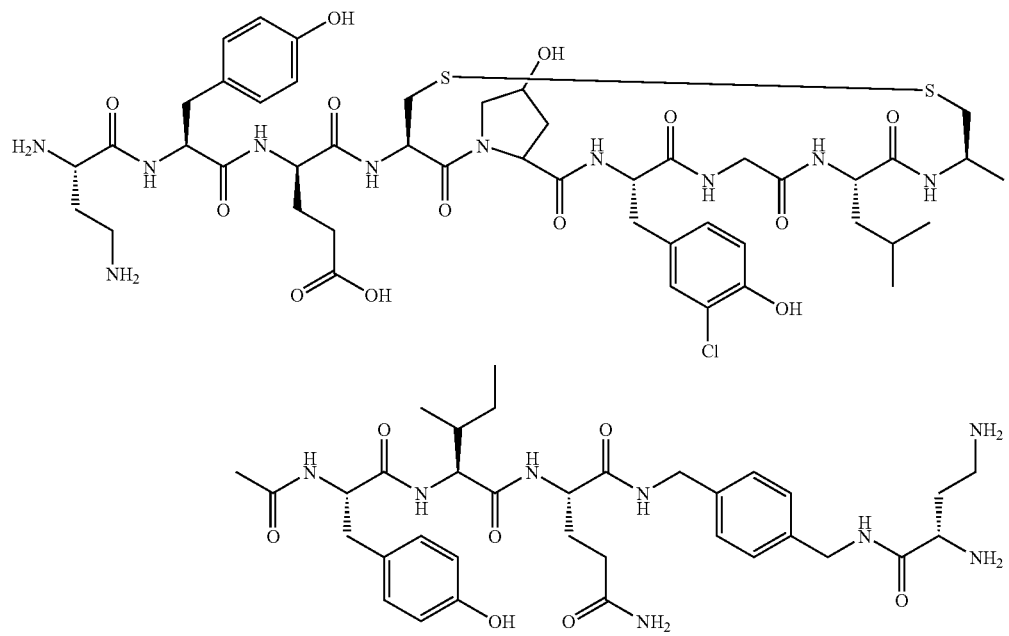

Compound 24

A 15 mmol synthesis of Compound 24 was completed using Rink Amide MBHA resin (substitution 0.66 mmol/g, Novabiochem cat #01-64-0037). The linear peptide was assembled on the resin with the aid of a C-terminal "pseudotripeptide" unit. This pseudotripeptide unit was synthesized in solution and consists of Fmoc-Glutamic acid, p-xylylenediamine, and Boc-Dab(Boc)-OH. The pseudotripeptide was then attached to the resin via the acid side chain of the Glutamic acid. Normal Fmoc peptide chemistry was then used to assemble the remainder of the peptide. The linear peptide was cleaved from the resin. Compound 24 was generated from the linear peptide via DMSO oxidation. The entire synthesis of Compound 24 is described in more detail below.

A. Elongation of the Peptide on the Resin

Each amino acid was added to the peptide sequence using standard Fmoc deprotection and coupling conditions. 22.7 g of Rink Amide MBHA resin was added to a 500 mL peptide reaction vessel. Each amino acid was added to the peptide-resin using the following steps:

1. Wash with 20% piperidine in DMF (250 mL×3 min)
2. Deprotect with 20% piperidine in DMF (250 mL×1 hour).
3. Wash with DMF (2×250 mL), DCM (2×250 mL), DMF (2×250 mL).

4. Dissolve amino acid (4 eq.) and 1-hydroxybenzotriazole (4 eq.) in DMF (250 mL).
5. Add amino acid solution to resin, and then add 1,3-diisopropylcarbodiimide (4 eq.).
6. Shake resin with activated amino acid for 18 hours at 250 rpm on an orbital shaker, unless otherwise indicated.
7. Wash the resin with DMF (1×250 mL), DCM (2×250 mL), DMF (3×250 mL).
8. Check coupling using the quantitative ninhydrin test shown below.
9. Cleave a small amount of the peptide from the resin with 90% trifluoroacetic acid 5% triisopropylsilane, and 5% water. Check purity of peptide by analytical HPLC.

The following is a list of the amino acids used in the synthesis:

| Amino Acid | Amount | Company | Catalog # |
|---|---|---|---|
| 1. Pseudotripeptide* †** | 47.2 g | in house synthesis | |
| 2. Fmoc-L-Ile-OH | 21.2 g | Novabiochem | 04-12-1024 |
| 3. Fmoc-L-Tyr(tBu)-OH | 27.6 g | Novabiochem | 04-12-1037 |
| 4. Fmoc-L-Cys(Trt)-OH | 35.1 g | Novabiochem | 04-12-1018 |
| 5. Fmoc-L-Leu-OH | 21.2 g | Novabiochem | 04-12-1025 |
| 6. Fmoc-L-Gly-OH | 17.8 g | Novabiochem | 04-12-1001 |
| 7. Fmoc-L-Tyr(3-Cl)—OH†† | 26.3 g | in house synthesis | |
| 8. Fmoc-L-Hyp(tBu)-OH | 24.6 g | Novabiochem | 04-12-1078 |
| 9. Fmoc-L-Cys(Trt)-OH | 35.1 g | Novabiochem | 04-12-1018 |
| 10. Fmoc-D-Glu-OH | 25.5 g | Novabiochem | 04-13-1051 |
| 11. Fmoc-L-Tyr(tBu)-OH | 27.6 g | Novabiochem | 04-12-1037 |
| 12. Boc-L-Dab(Boc)-OH•DCHA | 30.0 g | Bachem | A-3480 |

*The pseudotripeptide was synthesized in house using the procedure shown below.
†The pseudotripeptide was allowed to couple over the weekend for three days. (Previous experience with the synthesis of EP2080 peptide has shown that this longer coupling time was required for the attachment of the first amino acid to the resin).
**Typically the resin is capped with a solution of 5% acetic anhydride and 6% diisopropylethylamine in DMF after the first coupling. After the coupling of the amino acids is complete, the resin is washed with DMF (3 × 250 mL) and the capping solution (250 mL). The resin is shaken with the capping solution (250 mL) for 1 hour.
††Fmoc-Tyr(3-Cl)—OH was synthesized in house using the procedure shown below.

B. Synthesis of Pseudotripeptide

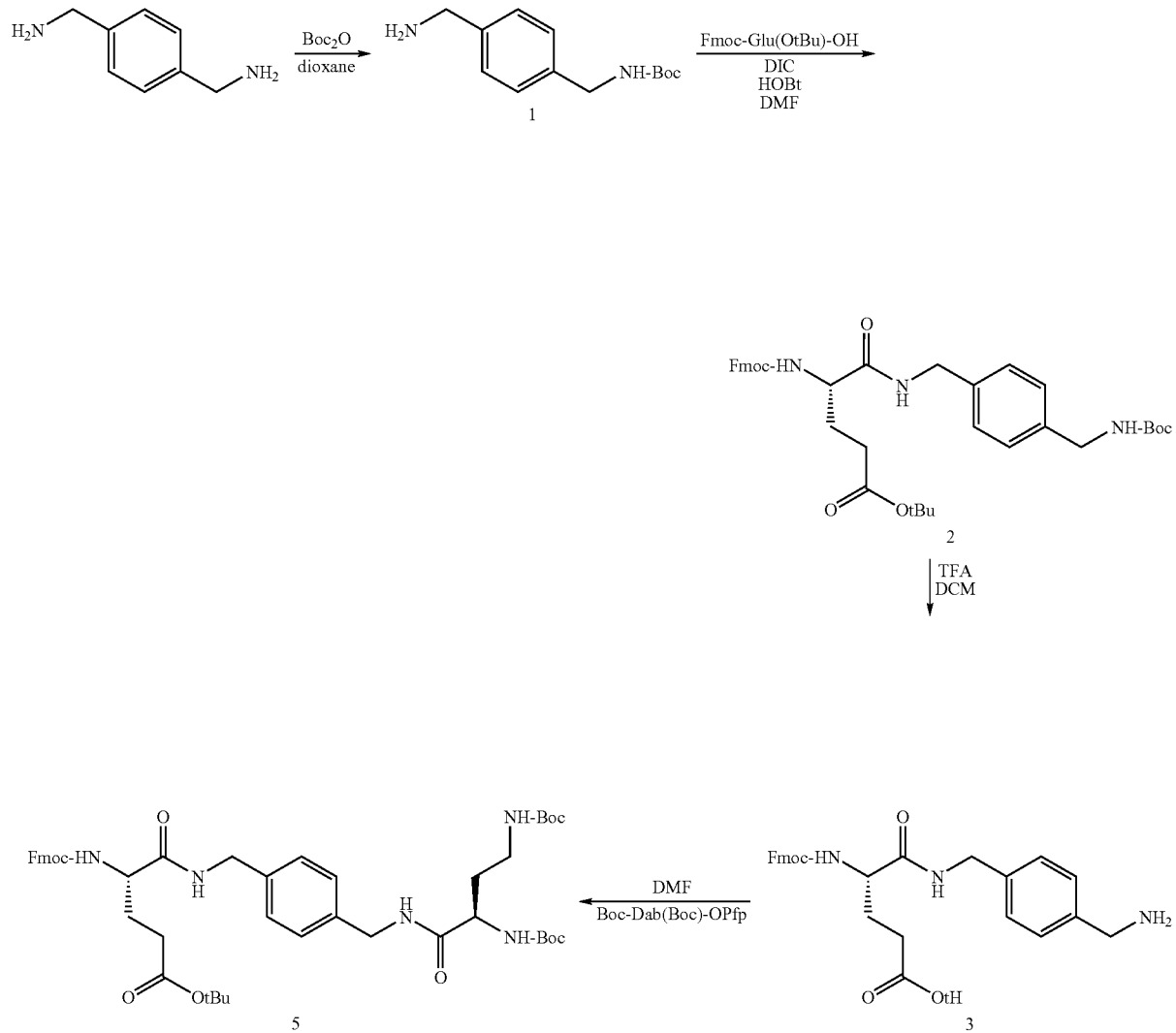

C. Synthesis of Mono-boc-p-xylylenediamine

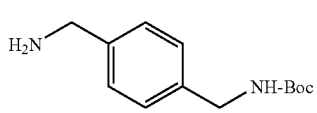

1 p-xylylenediamine (Aldrich 27,963-3) (50.0 g, 367 mmol) was transferred to a 3-neck round bottom flask equipped with a mechanical stirrer and addition funnel. The p-xylylenediamine was dissolved in dioxane (900 mL) at 22-25° C. Di-t-butyldicarbonate (Aldrich 20,524-9) (40.0 g, 367 mmol) was dissolved in dioxane (500 mL), and added to the addition funnel, and the solution was added dropwise to the stirring solution slowly over 5 hours at 22-25° C. Any precipitate was filtered and then washed with dioxane (200 mL). The filtrate was concentrated until a volume of 300 mL was achieved (under reduced pressure). The concentrated solution was poured into water (700 mL) over 5 minutes to precipitate the di-boc side product. The precipitate was filtered and washed with water (300 mL). The precipitate was discarded. The filtrate was extracted with ethyl acetate (3×500 mL). The extracts were combined and the organic layer washed with water (1×500 mL), saturated aqueous NaCl (1×500 mL) and dried over sodium sulfate. The organics were concentrated under vacuum to a constant weight (at room temperature) to obtain 1 as a pale beige solid. (22.30 g, 99% purity by area).

D. Preparation of Fmoc-Glu(tBu)-diamine(Boc)

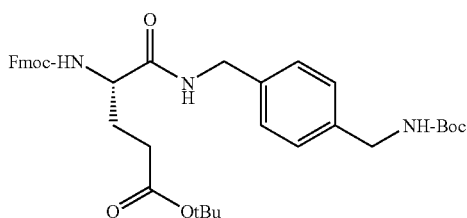

2

In a reaction flask, mono-boc-p-xylylenediamine 1 (22.3 g, 93 mmol) was dissolved in dimethylformamide (200 mL). In a separate flask Fmoc-Glu(tBu)-OH (Novabiochem, 04-12-1020) (37.6 g, 88.3 mmol), EDC (Advanced Chemtech, RC8102) (16.8 g, 88.3 mmol), and 1-hydroxybenzotriazole (Aldrich 15,726-0) (11.9 g, 88.3 mmol) were dissolved in acetonitrile (1 L). The solution was stirred for 15 mins at 22-25° C., and then added to the amine 1 solution over 5 minutes at 22-25° C. The reaction was stirred for 1.5 hours at 22-25° C. The reaction mixture was concentrated until a volume of 400 mL was achieved (under reduced pressure). The concentrated reaction solution was poured into water (1.6 L) to form a precipitate. The precipitate was filtered and washed with water (500 mL), and dried to a constant weight under vacuum (at room temperature) to give 2. (79.02 g, 96% purity by area)

E. Preparation of Fmoc-Glu-diamine

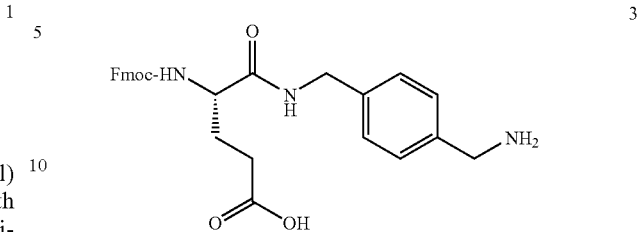

3

Fmoc-Glu(tBu)-diamine(Boc) ("88.3 mmol") from above, was dissolved into the following cocktail:

47.5% Trifluoroacetic acid (475 mL)
50% Dichloromethane (500 mL)
1.25% Triisopropylsilane (12.5 mL)
1.25% Water (12.5 mL).

The reaction was stirred for 2 hours at room temp. The reaction mixture was concentrated to a volume of 400 mL (under reduced pressure). The concentrated reaction solution was poured into cold (0° C.) ether* (800 mL) over 5 minutes. The precipitate was filtered and washed with ether* (600 mL). The precipitate was dried to a constant weight under vacuum (at room temperature) to give 3. (65.61 g, 98.3% purity by area).

*Isopropyl ether can also be used in place of diethyl ether during the preparation of 3.

F. Preparation of Boc-Dab(Boc)-OPfp

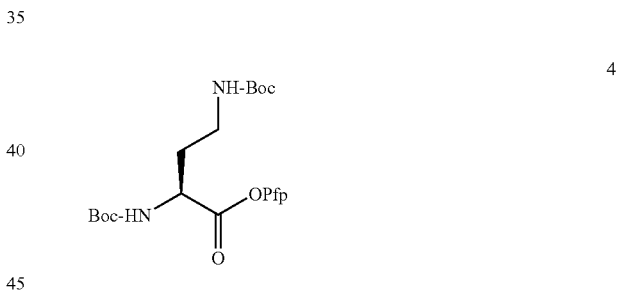

4

Boc-Dab(Boc)-OH.DCHA (Bachem A-3480)(20 g, 41.3 mmol) was dissolved in dichloromethane (200 mL) and 0.1 N potassium hydrogen sulfate (500 mL) at 22-25° C. for 1 hour. The layers were separated, and the aqueous layer extracted with dichloromethane (200 mL). The organic layers were combined, dried over sodium sulfate, and concentrated until a volume of 300 mL was achieved (under reduced pressure). Solid pentafluorophenol (Aldrich 10,379-9)(8.80 g, 48 mmol) was added, and then solid EDC (Advanced Chemtech RC8102)(9.2 g, 48 mmol) to the solution at 22-25° C. The reaction was stirred for 2 hours at 22-25° C. Water (300 mL) was added over 5 minutes, and the mixture stirred for 10 minutes at 22-25° C. The organic layer was separated, and washed with 0.1N KHSO₄ (400 mL). The aqueous layer was reextracted with DCM (250 mL). The organic extracts were combined, dried over sodium sulfate and concentrated to a constant weight under vacuum (at room temperature) to give 4 as a pale beige solid. (19.4 g, 95% purity by area)

G. Preparation of Pseudotripeptide

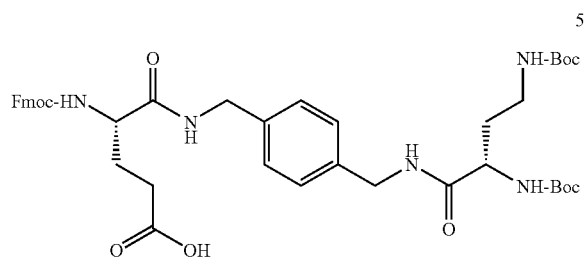

Fmoc-Glu-diamine 3 (60 g, 99.7 mmol) was dissolved in dimethylformamide (1 L) at 22-25° C. The pH of the solution was adjusted to ~7 with diisopropylethylamine (22 mL, 126 mmol). Boc-Dab(Boc)-OPfp 4 (112.4 g, 126 mmol) was added at 22-25° C. The pH was readjusted to 7 with diisopropylethylamine (22 mL, 126 mmol). The reaction was stirred for 2 hours at 22-25° C. The reaction was considered complete when less than 5% of compound 3 remained, and less than 1% of compound 4 remained as determined by Analytical Method 1. The reaction solution was added to water (3500 mL) over 20 minutes to form a precipitate. The precipitate was filtered, washed with water (1 L), and dried under vacuum at 60° C. to a constant weight to give 5. (67.7 g, 93% purity by area)

H. Synthesis of Fmoc-Tyr(3-Cl)-OH 3-chlorotyrosine* (Aldrich 51,244-3)(113.5 g, 526 mmol) was added to a roundbottom flask equipped with a mechanical stirrer and temperature probe. 3-chlorotyrosine was dissolved in a solution of dioxane:water 2:1 (500 mL). Sodium carbonate (55.8 g, 526 mmol) was added, and the solution cooled to 0° C. in an ice bath. Fmoc-OSu (177.5 g, 526 mmol) was dissolved in dioxane (300 mL) and added in one portion to the solution at 0° C. The reaction was stirred for 5 hours at 0° C. The reaction was allowed to warm to room temperature overnight. The reaction was concentrated until a volume of 100 mL was achieved. 0.5 M potassium hydrogensulfate was added until the pH was 3. The pH was determined using pH paper (0-14) that was placed directly into the mixture. The pH was determined by comparison with the chart included with the pH paper. The solution was extracted with ethyl acetate (3×500 mL). The organic layers were combined and washed with water (500 mL) and brine (500 mL). The organic layer was then washed over sodium sulfate and concentrated to a constant eight (under vacuum) to give Fmoc-3-chlorotyrosine as a light beige solid. (204 g, 95% purity by area)

*3-chlorotyrosine from Lancaster (#7675) has been used to synthesize Fmoc-3-chlorotyrosine as well.

I. Cleavage, Cyclization and Purification Procedures i. Cleavage

After the elongation of the peptide on the resin was complete, the resin was washed with DCM (3×250 mL). The resin was dried under reduced pressure at 22-25° C. for 18 hours. The weight of the dry peptide-resin (57.08 g) was determined. Approximately 15 mL/g (840 mL) of the following cleavage cocktail was added: 80% trifluoroacetic acid, 5% triisopropylsilane, 5% dodecanethiol, 5% dichloromethane, and 5% water. The peptide-resin was shaken for 1.25 hours at room temperature on an orbital shaker (250 rpm), and then filtered and washed with trifluoroacetic acid (2×100 mL). The filtrates were combined and poured into ether* (4 L) at 0° C. over 5 minutes to form a precipitate. The precipitate was filtered, washed with ether* (1 L), washed with acetonitrile (1 L), and dried under vacuum. 24.87 g. (73.3% purity by area, Analytical Method 2, 41.4% potency) (40% yield based on potency)

*Isopropyl ether has been substituted for diethyl ether successfully on a 2 mmol scale.

ii. Cyclization

The crude linear peptide (24.87 g) was dissolved in 15% DMSO/10% acetonitrile/75% water solution (2250 mL). The reaction was stirred at room temperature for 3 days, or until the reaction was complete. (73.9% purity, 44.8% potency, Analytical Method 2.) The reaction mixture was diluted with water (2250 mL) in order to prepare for HPLC purification.

iii. Purification

The peptide was purified by prep HPLC by direct injection of 500 mL of the solution from the cyclization procedure.

| Column: | Kromasil C18 100 Å 10 µm 2" × 250 mm |
|---|---|
| Flow Rate: | 100 mL/min |
| Wavelength: | 220 nm |
| Mobile Phase: | A: 0.1% Trifluoroacetic acid in water |
| | B: 0.1% Trifluoroacetic acid in acetonitrile |
| Gradient: | % B | Time |

| % B | Time |
|---|---|
| 5 | 0 |
| 5 | 2 |
| 20 | 7 |
| 35 | 32 |
| 95 | 35 |
| 95 | 45 |
| 5 | 47 |
| 5 | 53 |

The solution was injected onto the column. The method's starting conditions were initiated and held for approximately 5 minutes until all the DMSO eluted. The gradient was then started. 25 mL fractions of the peak centered at ~16 mins were collected. Nine injections were completed in this manner. The impure fractions were combined and repurified in one 500 mL injection. All pure fractions were combined, concentrated and lyophilized to give Compound 24. (20.04 g, 95.8% purity by area, Analytical Method 2, 65.2% potency)

iv. Analytical Methods

Method 1. The samples were analyzed using the following method:

| Column: | Vydac C4, 300 Å, 10 µm, 4.6 × 150 mm |
|---|---|
| Column Temp: | Room Temp |
| Flow Rate: | 1.0 mL/min |
| Buffer A: | 0.1% Trifluoroacetic acid in water |
| Buffer B: | 0.1% Trifluoroacetic acid in Acetonitrile |
| Gradient: | Time | % B |

| Time | % B |
|---|---|
| 0 | 5 |
| 12 | 60 |
| 16 | 100 |
| 17 | 5 |
| 20 | 5 |

Method 2. Samples were analyzed by the following 40 minute method.

| Column: | Kromasil C18 3.5 µm, 100 Å, 4.6 × 150 mm |
|---|---|
| Column Temp: | 37° C. |
| Flow Rate: | 1.0 mL/min |
| Buffer A: | 0.1% Trifluoroacetic acid in water |
| Buffer B: | 0.1% Trifluoroacetic acid in Acetonitrile |

-continued

| Gradient: | Time | % B |
|---|---|---|
| | 0 | 10 |
| | 10 | 25 |
| | 23 | 27 |
| | 25 | 30 |
| | 30 | 65 |
| | 34 | 95 |
| | 35 | 10 |
| | 40 | 10 |

Quantitative Ninhydrin Test

The yield of each amino acid coupling was determined using a quantitative ninhydrin test. A small amount of resin was placed into a 2 mL fritted filter funnel. The resin was washed with DMF 3× and DCM 4×, and then dried under vacuum. The resin was weighed in a scintillation vial. One scintillation vial without any resin was used as a blank. The following reagents were added to each vial:

| 76% W/V Phenol/EtOH: | 75 μL |
|---|---|
| 0.0002M KCN/Pyridine: | 100 μL |
| 0.28M Ninhydrin/EtOH: | 75 μL |

The vials were heated at 100° C. for 5 minutes on a heating block. The vials were then immediately removed from the heat and diluted with 4.8 mL of 60% ethanol. A spectrophotometer was zeroed with 60% ethanol at 570 nm. The absorbance of each sample at 570 nm was measured, including the blank. The substitution was calculated by using the following formula:

$$\mu mol/g \text{ of amine} = \frac{[\text{Abs sample} - \text{Abs blank}] * 5 \text{ mL} * 10^6}{15000 * \text{sample weight (mg)}}$$

The percent coupled was calculated using the following formula:

$$\% \text{ coupled} = \left\{ 1 - \frac{\text{amine } (\mu mol/g)}{10^3 * \text{substitution (mmol/g)}} \right\} * 100$$

The amino acid was recoupled if the percent coupled was less than 99%.

Example 7

Conversion of Protected Carboxylic Acid Ester Organic Chelating Ligands and Protected Carboxylic Acid Ester Chelating Ligand Precursors to Metal Chelates Referring to FIG. 6:

Scheme A: Conversion of tetra(t-Butyl)ester 3 to Gd chelate 4.

A suitable reaction vessel was charged with 15 mL of 1:1 DMF:H$_2$O. One ml of a 10 mM solution of compound 3 (1:1 DMF:H$_2$O) was added and 41 microliters of a 244.7 mM solution of gadolinium chloride hexahydrate in water was added. The solution was heated to 70° C. and the reaction was allowed to proceed for 24 hrs. The resultant gadolinium complex, 4, was isolated by precipitation after addition of 5 mL of di-isopropyl ether (42% yield).

Scheme B

A suitable reaction vessel was charged with 15 mL of 1:1 DMF:H$_2$O. One ml of a 10 mM solution of compound 2 (1:1 DMF:H$_2$O) was added and 41 microliters of a 244.7 mM solution of gadolinium chloride hexahydrate in water was added. The solution was heated to 70° C. and the reaction allowed to proceed for 24 hrs. The pH was raised to 11 by addition of sodium hydroxide and the reaction allowed to proceed for an additional hour at 70° C. After cooling to room temperature, the resultant gadolinium complex, 4, was isolated by precipitation after addition of 5 mL of di-isopropyl ether (19% yield).

This procedure has also been performed with the pentabenzyl ester analog of that shown in Scheme B. In some embodiments, DTPA esters can also be used.

Scheme C: Conversion of Organic Ligand Precursor to Metal Chelate

The synthesis of EP-2104-15 starting from EP-2104-07 was performed. A suitable reaction vessel was charged with a solution of 264 mg of 1 in 2 ml of 1:1 acetonitrile/water; 12 ml of 1:1 acetonitrile/water was added. The pH was brought to 11.44 by addition of 1 N NaOH. One equivalent of GdCl$_3$.6H$_2$O (211.3 mg) was added with stirring (pH 6.9 and pH raised to 10.63 with 1 N NaOH). Four equivalents of bromoacetic acid (261.3 mg) were dissolved in 2 mL of water and added dropwise over 15 minutes. The pH was maintained at 10 using a pH stat with 1 N NaOH. The reaction was then heated to 50° C. and allowed to proceed overnight. The reaction mixture was cooled to room temperature and the gadolinium complex 4 was identified by LC/MS.

As one of skill in the art will recognize, other paramagnetic metal ions may be substituted for the Gd(III) shown above.

Example 8

Characterization of Chelating Ligands and Metal Chelates

A. Relaxivity Measurements

Relaxivity measurements can be carried out by means known in the art. Relaxivities can be determined in the presence and absence of target molecules. Relaxivity can be measured at varying magnetic fields (e.g., from 0.5 T to 3 T, using spectrometers of the appropriate field strength) and varying temperatures (e.g., from about 10 to about 90° C.).

For example, relaxivity at about 37° C. can be measured with a Bruker NMS-120 Minispec NMR spectrometer operating at 0.47 Tesla (20 MHz H-1 Larmor frequency) and 37° C. or a Konig-Brown relaxometer (20 MHz, H-1 Larmor frequency) operating at 35° C. The T1 of water protons is determined by an inversion recovery pulse sequence using the instrument's software. Relaxivity is determined by measuring the T1 of multiple solutions of the target (for example, solutions of 4.5% HSA) containing zero, 20, 30, and 40 μM Gd(III), respectively. The samples are incubated at 37° C. for at least 15 minutes to ensure temperature equilibration before the T1 measurement is performed. The Gd(III) content of the samples is determined by inductively coupled plasma-mass spectrometry (ICP-MS). The relaxivity (per Gd(III) ion) is determined by plotting the relaxation rate (1/T1) in s$^{-1}$ versus the Gd(III) concentration in mM. The slope of a linear fit to the data gives the relaxivity. The relaxivity of the compounds in the absence of target is also determined in an analogous manner.

B. $^{17}O$ NMR $^{17}O$ NMR measurements at variable temperatures can be used to determine the mean residence time of water molecules in the first coordination sphere of a test metal chelate. The mean water residency time ($\tau_m$) of water coordinated to a test metal chelate, which is simply the inverse of the water exchange rate ($k_{ex}=1/\tau_m$), is determined by measuring the transverse relaxation rate of $H_2^{17}O$. The $^{17}O$ relaxation rates of water ($1/T_2$) are determined for a PBS solution in the presence and absence of 10 mM test metal chelate as a function of temperature (0-90° C.) on a Varian Unity 300 NMR operating at 40.6 MHz using a CPMG pulse sequence. The reduced relaxation rate, $1/T_{2r}$, is calculated, Eq 1, from the difference of relaxation rates between the test sample containing and the reference sample (PBS alone) and then dividing this result by $P_m$, the mole fraction of water bound to the Gd(III) ion in the test compound ($P_m=q[Gd]/[H_2O]$, where q is # of coordinated waters). The mean residency time at 37° C. (310 K) is obtained by fitting a plot of the reduced relaxation rates ($1/T_{2r}$) as a function of temperature (T) (Eqs 1-5). Here, $g_L$ is the Landé g factor for Gd, $\mu_B$ is the Bohr magneton, S is the spin quantum number of Gd, $A/\hbar$ is the hyperfine coupling constant ($-3.8\times10^6$ rad/s), R is the gas constant, h is Planck's constant, and $k_B$ is Boltzmann's constant. The data are fit to 4 parameters: $T_{1e}^{310}$ (the electronic relaxation time at 310 K), $E_{T1e}$ (the activation energy for electronic relaxation), $\Delta S\ddagger$ (the entropy of activation for water exchange), and $\Delta H\ddagger$ (the enthalpy of activation for water exchange). Once these four parameters are determined, the mean residency time at 37° C. (310 K) can be calculated using Eq. 4.

$$\frac{1}{T_{2r}} = \frac{1}{P_m}\left[\frac{1}{T_2} - \frac{1}{T_{2ref}}\right] = \frac{1}{\tau_m}\left(\frac{T_{2m}^{-1}(\tau_m^{-1}+T_{2m}^{-1})+\Delta\omega_m^2}{(T_{2m}^{-1}+\tau_m^{-1})^2+\Delta\omega_m^2}\right) \quad (1)$$

$$\Delta\omega_m = \frac{g_L\mu_B S(S+1)}{3k_B T}\frac{A}{\hbar} \quad (2)$$

$$\frac{1}{T_{2m}} = \frac{S(S+1)}{3}\left(\frac{A}{\hbar}\right)^2\left(\frac{1}{\tau_m}+\frac{1}{T_{1e}}\right) \quad (3)$$

$$\frac{1}{\tau_m} = k_{ex} = \frac{k_B T}{h}\exp\left[\frac{\Delta S^\ddagger}{R} - \frac{\Delta H^\ddagger}{RT}\right] \quad (4)$$

$$\frac{1}{T_{1e}} = \frac{1}{T_{1e}^{310}}\exp\left[\frac{E_{T1e}}{R}\left(\frac{1}{T} - \frac{1}{310.15}\right)\right] \quad (5)$$

C. Luminescence Lifetime Measurements

The number of coordinated water molecules can be extracted from luminescence lifetime measurements. Typically, europium(III) or terbium(III) chelates are used. In one method, two 50 μM solutions of a test Eu(III) complex are prepared in PBS: one in $H_2O$ and the other in $D_2O$. Eu(III) excitation spectra of the $^7F_0 \rightarrow ^5D_0$ transition (578-581 nm) and excited $^5D_0$ state lifetimes are obtained using a tunable Continuum TDL-50 dye laser pumped by a YG-581C Q-switched Nd:YAG laser (10 Hz, 40-70 mJ/pulse). The $^5D_0 \rightarrow ^7F_2$ emissive transition at 614 nm is monitored for lifetime determination. The determination of Eu(III) excited state lifetime is achieved by fitting Eu(III) luminescence decay data to a monoexponential decay function. The number of bound waters, q, is determined using the following equation:

$$q = 1.11\left(\frac{1}{\tau^{H_2O}} - \frac{1}{\tau^{D_2O}} - 0.30\right)$$

where $\tau^{H_2O}$ and $\tau^{D_2O}$ are the excited state lifetimes in water and deuterium oxide solution, respectively.

Example 9

Synthesis of EP-2104-15-PFP. An Activated Ester of a Metal Chelate

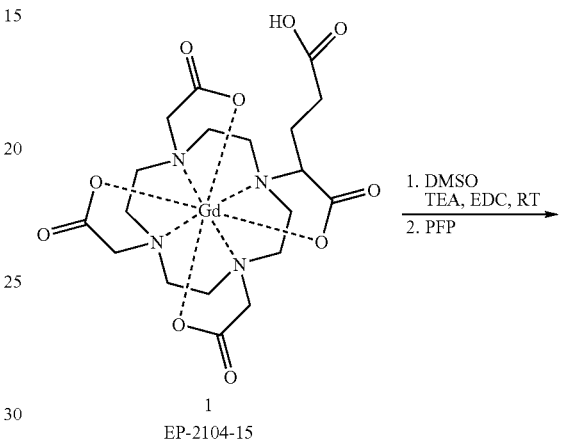

1
EP-2104-15

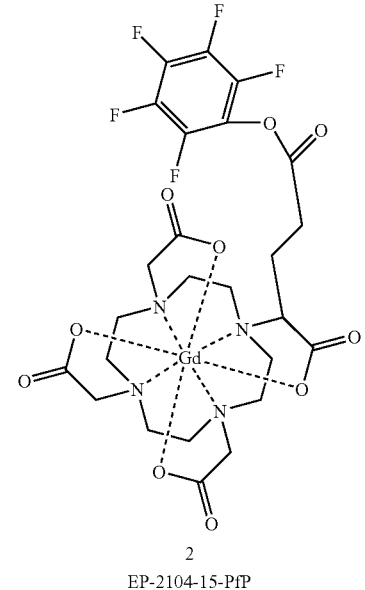

2
EP-2104-15-PfP

EP-2104-15 (1) (50 mg, 0.079 mmol) in DMSO (1 mL) was treated with EDC (8 mg, 0.0418 mmol). TEA was added until the pH was ~7. The solution was stirred for 10 minutes at RT. The mixture was treated with pentafluorophenol (PFP) (10.2 mg, 0.0554 mmol) and stirred for 4 hours at RT. The mixture was charged with acetone (5 mL) and the resulting precipitate was collected by suction filtration to give 68 mg of white solid.

Example 10
Synthesis of Compound 30
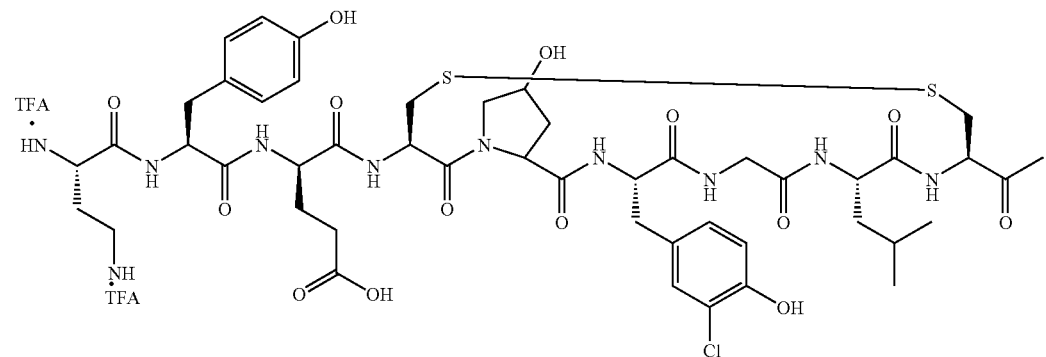
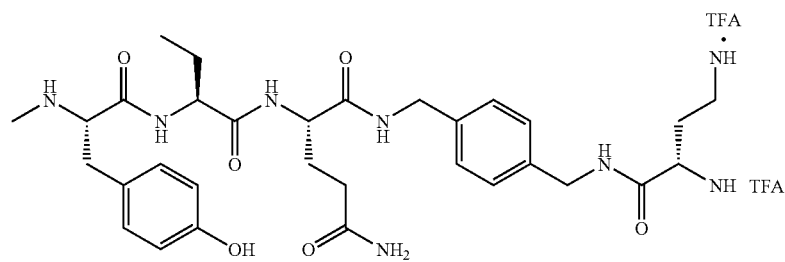
EP2104-24 -TFA
EP-2104-15-PFP
EDC
DMSO
TEA
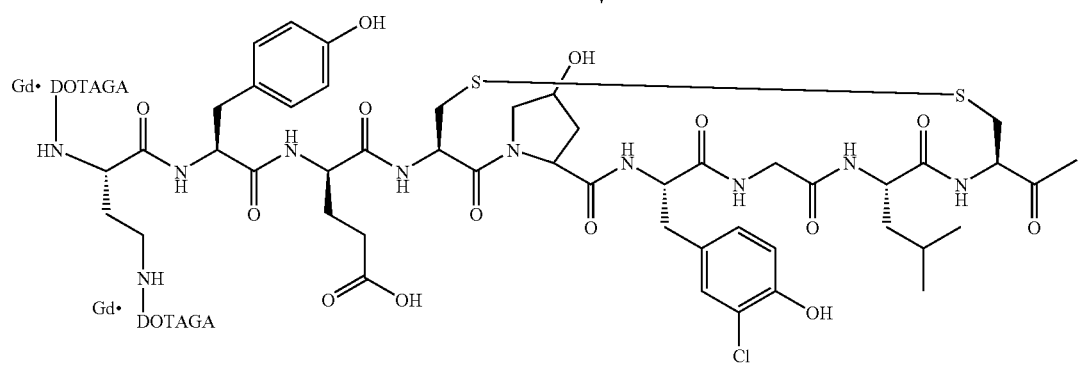
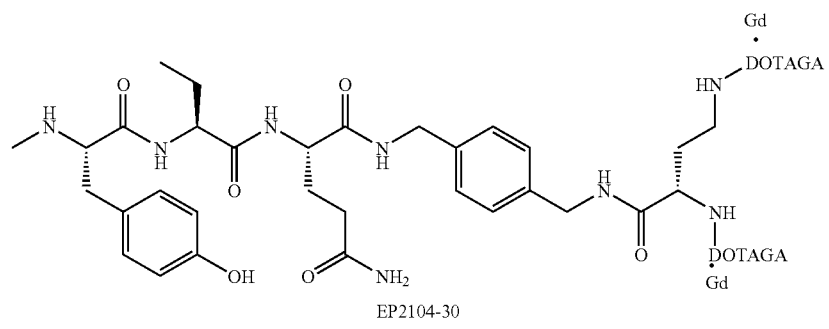
EP2104-30

Compound 24-TFA (7.0 mg) was dissolved in 2.5 mL of DMSO. The solution was treated with TEA (2 μL) to pH 9 to yield the free base, Compound 24. 49.0 mg of EP-2104-15-PFP, an activated ester metal chelate, was added to the solution and stirred at room temperature under nitrogen for 24 hours. Additional TEA (1 μL) was added to bring the pH of the solution to ~7.5. Additional EP-2104-15-PFP (5 mg) was added to the solution and stirred for 2 hours under nitrogen at room temperature. The solution was charged with diethyl ether and the resulting solid was isolated by suction filtration to give Compound 30 (70% purity).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a metal chelate having a structure:

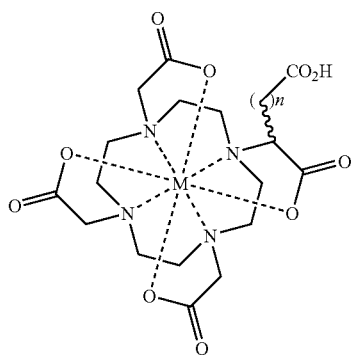

said composition having an enantiomeric excess of greater than 50% of an (R) isomer of said chelate at the 2 position, wherein n can range from 1 to 4, and wherein M can be selected from the group consisting of Gd(III), Fe(III), Mn(II), Mn(III), Cr(III), Cu(II), Dy(III), Ho(III), Er(III), Eu(III), Tb(II), Tb(III), Ce(III), Pr(III), Yb(III), Tm(III), Nd(III), and Tb(IV); and wherein said chelate is conjugated optionally through a linker to one or more TBMs, wherein said TBM is a peptide.

2. A composition comprising a metal chelate having a structure:

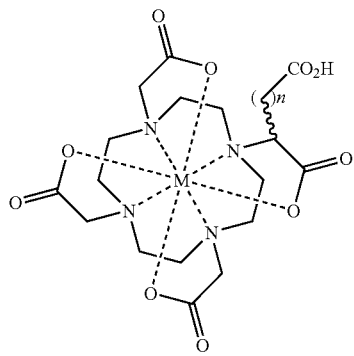

said composition having an enantiomeric excess of greater than 50% of an (S) isomer of said chelate at the 2 position, wherein n can range from 1 to 4, and wherein M can be selected from the group consisting of Gd(III), Fe(III), Mn(II), Mn(III), Cr(III), Cu(II), Dy(III), Ho(III), Er(III), Eu(III), Tb(II), Tb(III), Ce(III), Pr(III), Yb(III), Tm(III), Nd(III), and Tb(IV); and wherein said chelate is conjugated optionally through a linker to one or more TBMs, wherein said TBM is a peptide.

3. The composition of claim 1, wherein said composition has an enantiomeric excess of greater than 85% of the (R) isomer at the 2 position.

4. The composition of claim 2, wherein said composition has an enantiomeric excess of greater than 85% of the (S) isomer at the 2 position.

5. The composition of claim 1, wherein said composition has an enantiomeric excess of about 97% or more of the (R) isomer at the 2 position.

6. The composition of claim 2, wherein said composition has an enantiomeric excess of about 97% or more of the (S) isomer at the 2 position.

7. The composition of any one of claim 1 or 2, wherein said TBM is linked by a linker to the metal chelate.

8. The composition of claim 1 or 2, wherein a ratio of TBM to metal chelate in said composition can be from about 1:8 to about 8:1.

9. The composition of claim 8, wherein said ratio of TBM to metal chelate is about 1:4.

10. The composition of claim 8, wherein said ratio of TBM to metal chelate is about 2:2.

11. The composition of claim 1 or 2, wherein said peptide is about 10 to about 15 amino acids in length.

12. The composition of claim 1 or 2, wherein said peptide has an affinity for fibrin.

13. The composition of claim 12, wherein said peptide comprises one or more non-natural amino acids.

14. The composition of claim 13, wherein said peptide is selected from:

```
                                       (SEQ ID NO: 14)
W-dE-C-P(4-OH)-Y(3-Cl)-G-L-C-W-I-Q;

(SEQ ID NO: 15)
Y-dE-C-P(4-OH)-Y(3-Cl)-G-L-C-Y-I-Q;

(SEQ ID NO: 16)
Y-dE-C-P(4-OH)-Y(3-Cl)-G-L-C-W-I-Q;

(SEQ ID NO: 17)
W-dE-C-P(4-OH)-Y(3-Cl)-G-L-C-Y-I-Q;

(SEQ ID NO: 18)
W-dE-C-P(4-OH)-Y(3-Cl)-D-L-C-W-I-Q;

(SEQ ID NO: 19)
Y-dE-C-P(4-OH)-Y(3-Cl)-D-L-C-Y-I-Q;

(SEQ ID NO: 20)
Y-dE-C-P(4-OH)-Y(3-Cl)-D-L-C-W-I-Q;

(SEQ ID NO: 21)
W-dE-C-P(4-OH)-Y(3-Cl)-D-L-C-Y-I-Q;

(SEQ ID NO: 22)
F(4-OMe)-H-C-P(4-OH)-Y(3-Cl)-D-L-C-H-I-L;

(SEQ ID NO: 23)
Y-H-C-P(4-OH)-Y(3-Cl)-G-L-C-W-I-Q;

(SEQ ID NO: 24)
W-dE-C-P-Y(3-Cl)-G-L-C-W-I-Q;

(SEQ ID NO: 25)
W-dE-C-P(4-OH)-Y-G-L-C-W-I-Q;
and (SEQ ID NO: 26)
F-H-C-P(4-OH)-Y(3-Cl)-D-L-C-H-I-L.
```

15. The composition of claim 1 or 2, wherein said peptide has a binding affinity for hyaluronic acid.

16. The composition of claim 15, wherein said peptide is selected from:

```
G-A-H-W-Q-F-N-A-L-T-V-R;       (SEQ ID. NO: 1)

T-S-Y-G-R-P-A-L-L-P-A-A;       (SEQ ID. NO: 2)

M-D-H-L-A-P-T-R-F-R-P-A-I;     (SEQ ID. NO: 3)

T-L-R-A-I-W-P-M-W-M-S-S;       (SEQ ID. NO: 4)

I-P-L-T-A-N-Y-Q-G-D-F-T.       (SEQ ID. NO: 5)
```

17. The composition of claim 1 or 2, wherein said peptide has an affinity for collagen.

18. The composition of claim 17, wherein said collagen is a component of myocardium.

19. The composition of claim 17, wherein said peptide has the following general formula:

$$X_1\text{-}X_2\text{-}X_3\text{-}X_4\text{-}X_5\text{-}X_6\text{-}X_7\text{-}X_8\text{-}X_9\text{-}X_{10}, \quad \text{(SEQ ID. NO: 8)}$$

wherein:
$X_1$ is W, C, or A;
$X_2$ is R, C, or A;
$X_3$ is E, C, A, K, or T;
$X_4$ is P, C, or A;
$X_5$ is D, G, S, C, or A;
$X_6$ is F, R, C, or A;
$X_7$ is C, M, or A;
$X_8$ is A, E, or C;
$X_9$ is L, M, R, C, or A; and
$X_{10}$ is S, N, G, L, C, or A;
wherein, no more than 3 of $X_1$-$X_{10}$ are C or A, independently; and wherein the total number of C and A residues in $X_1$-$X_{10}$ is a maximum of 4.

20. The composition of claim 19, wherein said peptide is selected from:

```
W-R-E-P-S-F-C-A-L-S;       (SEQ ID. NO: 9)

W-R-E-P-S-F-M-A-L-S;       (SEQ ID. NO: 10)
and

W-R-E-P-G-F-C-A-L-S.       (SEQ ID. NO: 11)
```

21. The composition of claim 17, wherein said peptide has the following general formula:

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}, \quad \text{(SEQ ID. NO: 12)}$$

wherein:
$X_1$ is W, C, or A;
$X_2$ is R, C, or A;
$X_3$ is E, C, A, K, or T;
$X_4$ is P, C, or A;
$X_5$ is D, G, S, C, or A;

$X_6$ is F, R, C, or A;
$X_7$ is C, M, or A;
$X_8$ is A, E, or C;
$X_9$ is L, M, R, C, or A;
$X_{10}$ is S, N, G, L, C, or A;
$X_{11}$ is C, M, or A;
$X_{12}$ is P, A, or C; and
$X_{13}$ is K, Q, P, H, G, C, or A;
wherein no more than 4 of $X_1$-$X_{13}$ are C or A, independently; and wherein the total number of C and A residues in $X_1$-$X_{13}$ is a maximum of 5.

22. The composition of claim 17, wherein said peptide has the following general formula:

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15},$$ (SEQ ID. NO: 13)

wherein:
$X_1$ is V, I, or C;
$X_2$ is A, C, R, or D;
$X_3$ is W, C, or A;
$X_4$ is R, C, or A;
$X_5$ is E, C, A, K, or T;
$X_6$ is P, C, or A;
$X_7$ is D, G, S, C, or A;
$X_8$ is F, R, C, or A;
$X_9$ is C, M, or A;
$X_{10}$ is E, A, or C;
$X_{11}$ is L, C, A, M, or R;
$X_{12}$ is S, C, A, N, G, or L;
$X_{13}$ is C, M, or A;
$X_{14}$ is P, A, or C; and
$X_{15}$ is K, Q, P, H, G, C, or A;
wherein no more than 4 of $X_1$-$X_{15}$ are C or A, independently; and wherein the total number of C and A residues in $X_1$-$X_{15}$ is a maximum of 6.

23. The composition of claim 7, wherein said linker comprises a linear, branched, or cyclic peptide sequence.

24. The composition of claim 23, wherein said peptide sequence comprises a linear dipeptide.

25. The composition of claim 24, wherein said linear dipeptide is G-G.

26. The composition of claim 7, wherein said linker comprises an amide, sulfonamide, urea, thiourea, or carbamate moiety.

27. The composition of claim 26, wherein said linker is an amide, sulfonamide, urea, thiourea, or carbamate moiety.

28. The composition of claim 7, wherein said linker comprises a linear, branched, or cyclic alkane, alkene, or alkyne, or a phosphodiester moiety.

29. The composition of claim 28, wherein said linker is a linear, branched, or cyclic alkane, alkene, or alkyne, or a phosphodiester moiety.

30. The composition of claim 29, wherein said linker is substituted with one or more the following moieties: ketone, ester, amide, ether, carbonate, sulfonamide, or carbamate.

31. The composition of claim 7, wherein said linker is selected from:

—NH—CO—NH—;
—CO—(CH$_2$)$_n$—NH—;
dpr;
dab;
—NH-Ph-;
—NH—(CH$_2$)$_n$—;
—CO—NH—;
—(CH$_2$)$_n$—NH—;

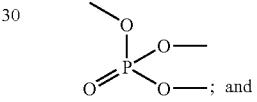; and

—CS—NH—;
wherein n is 1 to 10.

32. A composition comprising a contrast agent, or a pharmaceutically acceptable salt thereof, having a structure:

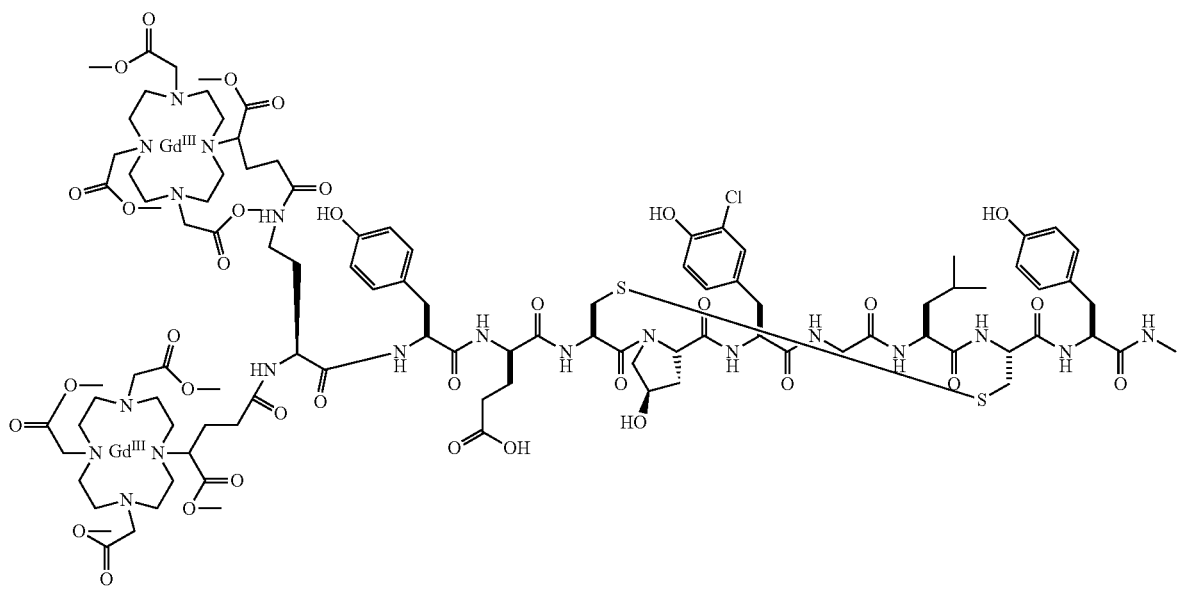

-continued
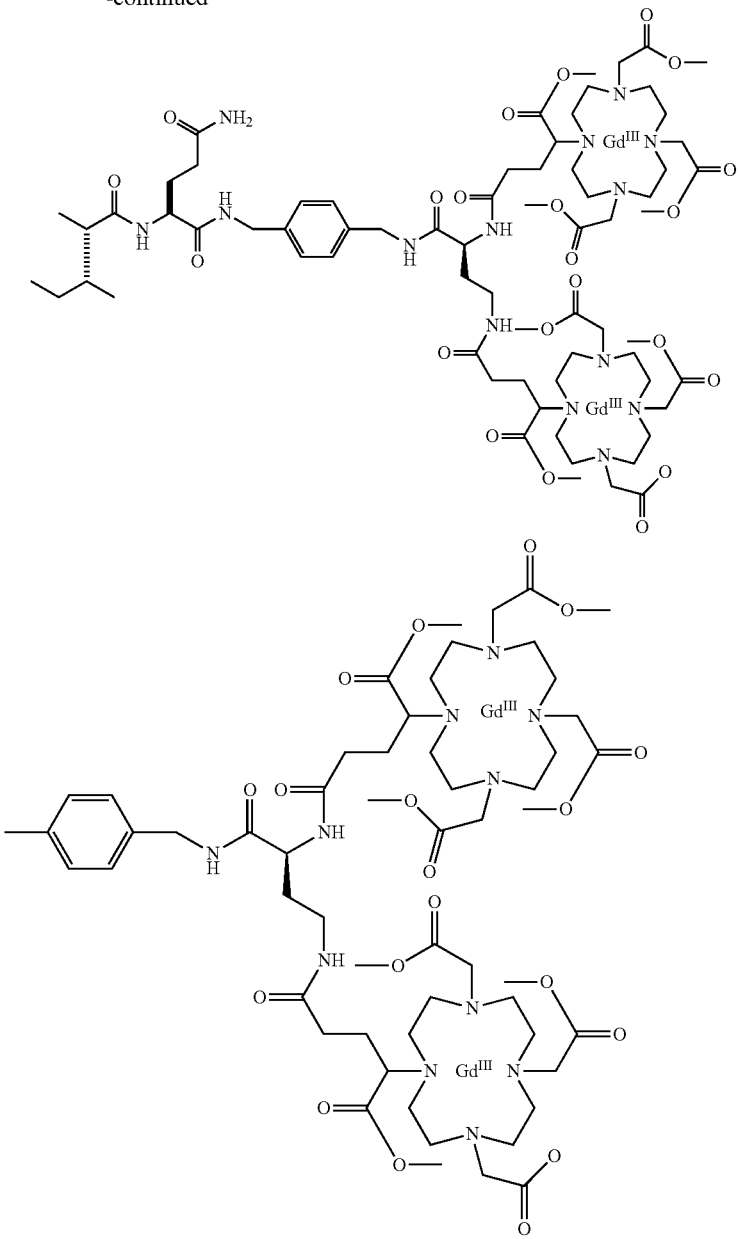
wherein said composition has an enantiomeric excess of greater than 85% of the (R) isomer at the 2 position of the metal chelate.
33. The composition of claim 32, wherein said composition has an enantiomeric excess of about 97% or more of the (R) isomer at the 2 position of the metal chelate.
* * * * *

UNITED STATES PATENT AND TRADEMARK OFFICE
CERTIFICATE OF CORRECTION

| | | |
|---|---|---|
| PATENT NO. | : 8,048,906 B2 | Page 1 of 3 |
| APPLICATION NO. | : 11/542883 | |
| DATED | : November 1, 2011 | |
| INVENTOR(S) | : John C. Amedio | |

It is certified that error appears in the above-identified patent and that said Letters Patent is hereby corrected as shown below:

First Page, Column 1 (Other Publications), Line 2, please delete "Diastereoisomeric" and insert -- Diastereomeric --, therefor;

First Page, Column 2 (Other Publications), Line 31, please delete "Didepsipeptides" and insert -- Depsipeptides --, therefor;

First Page, Column 2 (Other Publications), Line 38, please delete "αΔ-" and insert -- α"- --, therefor;

Column 1, Line 9, please delete "May 5, 2004" and insert -- May 20, 2004 --, therefor;

Columns 85-86, Line 2 (Claim 32), please delete

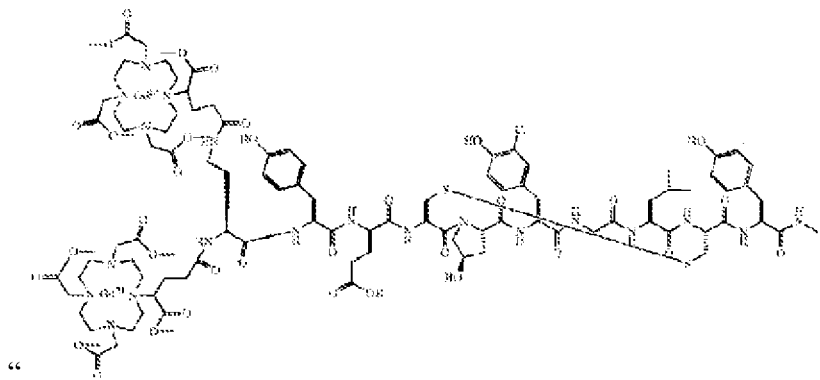

Signed and Sealed this
Eighth Day of May, 2012

David J. Kappos
*Director of the United States Patent and Trademark Office*

CERTIFICATE OF CORRECTION (continued)
U.S. Pat. No. 8,048,906 B2

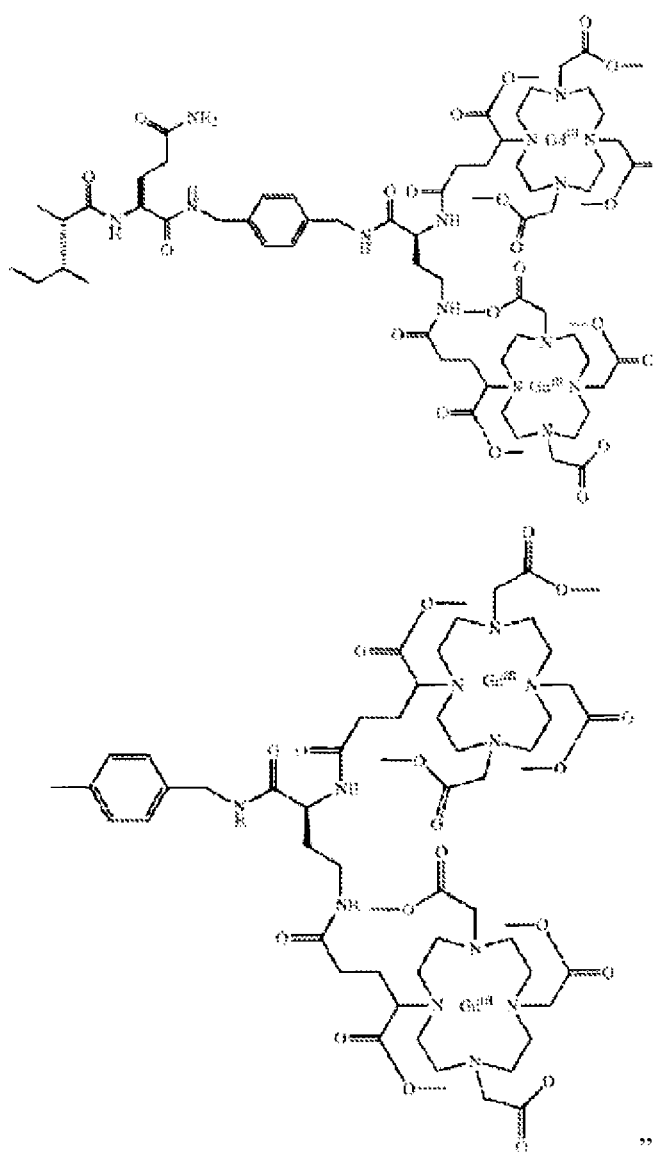

and insert
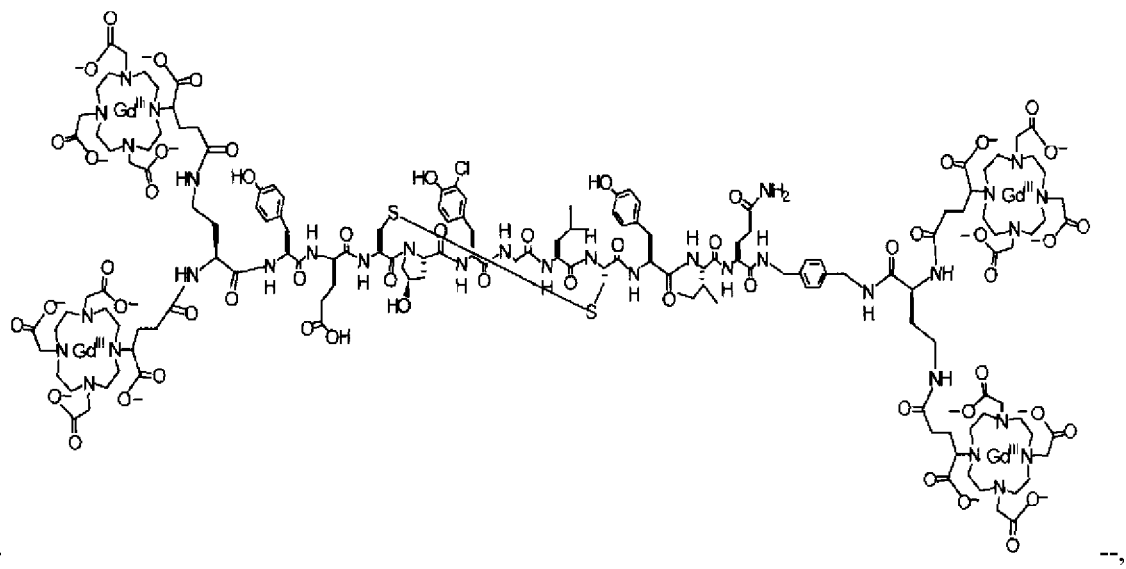
--
therefor.

```
                       SEQUENCE LISTING

<160> NUMBER OF SEQ ID NOS: 26

<210> SEQ ID NO 1
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 1

Gly Ala His Trp Gln Phe Asn Ala Leu Thr Val Arg
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 2

Thr Ser Tyr Gly Arg Pro Ala Leu Leu Pro Ala Ala
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 3

Met Asp His Leu Ala Pro Thr Arg Phe Arg Pro Ala Ile
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 4

Thr Leu Arg Ala Ile Trp Pro Met Trp Met Ser Ser
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 5
```

```
Ile Pro Leu Thr Ala Asn Tyr Gln Gly Asp Phe Thr
 1               5                  10
```

<210> SEQ ID NO 6
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 6

```
Ala Cys Gln Trp His Arg Val Ser Val Arg Trp Gly
 1               5                  10
```

<210> SEQ ID NO 7
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 7

```
Cys Arg Pro Lys Ala Lys Ala Lys Ala Lys Ala Lys Asp Gln Thr Lys
 1               5                  10                  15
```

<210> SEQ ID NO 8
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Trp, Cys, or Ala
<220> FEATURE:
<221> NAME/KEY: VARIANT
<222> LOCATION: 2
<223> OTHER INFORMATION: Xaa = Arg, Cys, or Ala
<220> FEATURE:
<221> NAME/KEY: VARIANT
<222> LOCATION: 3
<223> OTHER INFORMATION: Xaa= Glu, Cys, Ala, Lys, or Thr
<220> FEATURE:
<221> NAME/KEY: VARIANT
<222> LOCATION: 4
<223> OTHER INFORMATION: Xaa= Pro, Cys, or Ala
<220> FEATURE:
<221> NAME/KEY: VARIANT
<222> LOCATION: 5
<223> OTHER INFORMATION: Xaa= Asp, Gly, Ser, Cys, or Ala
<220> FEATURE:
<221> NAME/KEY: VARIANT
<222> LOCATION: 6
<223> OTHER INFORMATION: Xaa= Phe, Arg, Cys, or Ala
<220> FEATURE:
<221> NAME/KEY: VARIANT
<222> LOCATION: 7
<223> OTHER INFORMATION: Xaa= Cys, Met, or Ala
<220> FEATURE:
<221> NAME/KEY: VARIANT
<222> LOCATION: 8
<223> OTHER INFORMATION: Xaa= Ala, Glu, or Cys
<220> FEATURE:
<221> NAME/KEY: VARIANT
<222> LOCATION: 9
<223> OTHER INFORMATION: Xaa = Leu, Met, Arg, Cys, or Ala
<220> FEATURE:
<221> NAME/KEY: VARIANT
<222> LOCATION: 10
<223> OTHER INFORMATION: Xaa = Ser, Asn, Gly, Leu, Cys, or Ala

<400> SEQUENCE: 8

```
Xaa Xaa Xaa Xaa Xaa Xaa Xaa Xaa Xaa Xaa
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 9

Trp Arg Glu Pro Ser Phe Cys Ala Leu Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 10

Trp Arg Glu Pro Ser Phe Met Ala Leu Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 11

Trp Arg Glu Pro Gly Phe Cys Ala Leu Ser
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa= Trp, Cys, or Ala
<220> FEATURE:
<221> NAME/KEY: VARIANT
<222> LOCATION: 2
<223> OTHER INFORMATION: Xaa= Arg, Cys, or Ala
<220> FEATURE:
<221> NAME/KEY: VARIANT
<222> LOCATION: 3
<223> OTHER INFORMATION: Xaa= Glu, Cys, Ala, Lys, or Thr
<220> FEATURE:
<221> NAME/KEY: VARIANT
<222> LOCATION: 4
<223> OTHER INFORMATION: Xaa= Pro, Cys, or Ala
<220> FEATURE:
<221> NAME/KEY: VARIANT
<222> LOCATION: 5
<223> OTHER INFORMATION: Xaa= Asp, Gly, Ser, Cys, or Ala
<220> FEATURE:
<221> NAME/KEY: VARIANT
<222> LOCATION: 6
<223> OTHER INFORMATION: Xaa= Phe, Arg, Cys, or Ala
<220> FEATURE:
<221> NAME/KEY: VARIANT
<222> LOCATION: 7
<223> OTHER INFORMATION: Xaa= Cys, Met, or Ala
<220> FEATURE:
<221> NAME/KEY: VARIANT
<222> LOCATION: 8
```

-continued

```
<223> OTHER INFORMATION: Xaa= Ala, Glu, or Cys
<220> FEATURE:
<221> NAME/KEY: VARIANT
<222> LOCATION: 9
<223> OTHER INFORMATION: Xaa= Leu, Met, Arg, Cys, or Ala
<220> FEATURE:
<221> NAME/KEY: VARIANT
<222> LOCATION: 10
<223> OTHER INFORMATION: Xaa= Ser, Asn, Gly, Leu, Cys, or Ala
<220> FEATURE:
<221> NAME/KEY: VARIANT
<222> LOCATION: 11
<223> OTHER INFORMATION: Xaa= Cys, Met, or Ala
<220> FEATURE:
<221> NAME/KEY: VARIANT
<222> LOCATION: 12
<223> OTHER INFORMATION: Xaa= Pro, Ala, or Cys
<220> FEATURE:
<221> NAME/KEY: VARIANT
<222> LOCATION: 13
<223> OTHER INFORMATION: Xaa= Lys, Gln, Pro, His, Gly, Cys, or Ala

<400> SEQUENCE: 12

Xaa Xaa Xaa Xaa Xaa Xaa Xaa Xaa Xaa Xaa Xaa Xaa Xaa
 1               5                  10

<210> SEQ ID NO 13
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa= Val, Ile, Cys, or Ala
<220> FEATURE:
<221> NAME/KEY: VARIANT
<222> LOCATION: 2
<223> OTHER INFORMATION: Xaa= Ala, Gly, Arg, Asp, or Cys
<220> FEATURE:
<221> NAME/KEY: VARIANT
<222> LOCATION: 3
<223> OTHER INFORMATION: Xaa= Trp, Cys, or Ala
<220> FEATURE:
<221> NAME/KEY: VARIANT
<222> LOCATION: 4
<223> OTHER INFORMATION: Xaa= Arg, Cys, or Ala
<220> FEATURE:
<221> NAME/KEY: VARIANT
<222> LOCATION: 5
<223> OTHER INFORMATION: Xaa= Glu, Cys, Ala, Lys, or Thr
<220> FEATURE:
<221> NAME/KEY: VARIANT
<222> LOCATION: 6
<223> OTHER INFORMATION: Xaa= Pro, Cys, or Ala
<220> FEATURE:
<221> NAME/KEY: VARIANT
<222> LOCATION: 7
<223> OTHER INFORMATION: Xaa= Asp, Gly, Ser, Cys, or Ala
<220> FEATURE:
<221> NAME/KEY: VARIANT
<222> LOCATION: 8
<223> OTHER INFORMATION: Xaa= Phe, Arg, Cys, or Ala
<220> FEATURE:
<221> NAME/KEY: VARIANT
<222> LOCATION: 9
<223> OTHER INFORMATION: Xaa= Cys, Met, or Ala
<220> FEATURE:
<221> NAME/KEY: VARIANT
<222> LOCATION: 10
<223> OTHER INFORMATION: Xaa= Glu, Ala, or Cys
<220> FEATURE:
<221> NAME/KEY: VARIANT
<222> LOCATION: 11
<223> OTHER INFORMATION: Xaa= Leu, Cys, Ala, Met, or Arg
<220> FEATURE:
<221> NAME/KEY: VARIANT
```

```
<222> LOCATION: 12
<223> OTHER INFORMATION: Xaa= Ser, Cys, Ala, Asn, Gly, or Leu
<220> FEATURE:
<221> NAME/KEY: VARIANT
<222> LOCATION: 13
<223> OTHER INFORMATION: Xaa= Cys, Met, or Ala
<220> FEATURE:
<221> NAME/KEY: VARIANT
<222> LOCATION: 14
<223> OTHER INFORMATION: Xaa= Pro, Ala, or Cys
<220> FEATURE:
<221> NAME/KEY: VARIANT
<222> LOCATION: 15
<223> OTHER INFORMATION: Xaa= Lys, Gln, Pro, His, Gly, Cys, or Ala

<400> SEQUENCE: 13

Xaa Xaa Xaa Xaa Xaa Xaa Xaa Xaa Xaa Xaa Xaa Xaa Xaa Xaa Xaa
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 14

Trp Glu Cys Pro Tyr Glu Leu Cys Trp Ile Gln
1               5                   10

<210> SEQ ID NO 15
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 15

Tyr Glu Cys Pro Tyr Gly Leu Cys Tyr Ile Gln
1               5                   10

<210> SEQ ID NO 16
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 16
```

Tyr Glu Cys Pro Tyr Gly Leu Cys Trp Ile Gln
1               5                   10

<210> SEQ ID NO 17
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 17

Trp Glu Cys Pro Tyr Gly Leu Cys Tyr Ile Gln
1               5                   10

<210> SEQ ID NO 18
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 18

Trp Glu Cys Pro Tyr Asp Leu Cys Trp Ile Gln
1               5                   10

<210> SEQ ID NO 19
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 19

Tyr Glu Cys Pro Tyr Asp Leu Cys Tyr Ile Gln
1               5                   10

<210> SEQ ID NO 20
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5

<223> OTHER INFORMATION: / meta-chlorotyrosine

<400> SEQUENCE: 20

Tyr Glu Cys Pro Tyr Asp Leu Cys Trp Ile Gln
1               5                   10

<210> SEQ ID NO 21
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 21

Trp Glu Cys Pro Tyr Asp Leu Cys Tyr Ile Gln
1               5                   10

<210> SEQ ID NO 22
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 1
<223> OTHER INFORMATION: / 4-methoxyphenylalanine
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 22

Phe His Cys Pro Tyr Asp Leu Cys His Ile Leu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 23

Tyr His Cys Pro Tyr Gly Leu Cys Trp Ile Gln
1               5                   10

<210> SEQ ID NO 24
<211> LENGTH: 11
<212> TYPE: PRT
<213> ORGANISM: Artificial Sequence
<220> FEATURE:

```
<223> OTHER INFORMATION: synthetically generated peptide
<220> FEATURE:
<221> NAME/KEY: MOD_RES
<222> LOCATION: 5
<223> OTHER INFORMATION: / meta-chlorotyrosine

<400> SEQUENCE: 24

Trp Glu Cys Pro Tyr Gly Leu Cys Trp Ile Gln
1               5                   10

<210> SEQ ID NO 25
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline

<400> SEQUENCE: 25

Trp Glu Cys Pro Tyr Gly Leu Cys Trp Ile Gln
1               5                   10

<210> SEQ ID NO 26
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: / 4-hydroxyproline
<220> FEATURE:
<221> NAME/KEY: MOD_RES
<222> LOCATION: 5
<223> OTHER INFORMATION: / meta-chlorotyrosine

<400> SEQUENCE: 26

Phe His Cys Pro Tyr Asp Leu Cys His Ile Leu
1               5                   10
```